US008785496B2

(12) United States Patent
Baxter et al.

(10) Patent No.: US 8,785,496 B2
(45) Date of Patent: *Jul. 22, 2014

(54) METHOD OF USING BETA-HYDROXY-BETA-METHYLBUTYRATE FOR TREATING DISEASE-ASSOCIATED WASTING

(75) Inventors: Jeffrey H. Baxter, Westerville, OH (US); Anne C. Voss, Columbus, OH (US); Pradip Mukerji, Gahanna, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/348,024

(22) Filed: Jan. 11, 2012

(65) Prior Publication Data
US 2012/0189716 A1    Jul. 26, 2012

Related U.S. Application Data

(60) Division of application No. 11/025,466, filed on Dec. 29, 2004, now Pat. No. 8,217,077, which is a continuation-in-part of application No. 10/810,762, filed on Mar. 26, 2004, now abandoned.

(51) Int. Cl.
*A61K 31/19* (2006.01)
*A61K 31/205* (2006.01)

(52) U.S. Cl.
USPC .......................................... 514/557; 514/554

(58) Field of Classification Search
USPC ................................. 514/557, 554
See application file for complete search history.

(56) References Cited

U.S. PATENT DOCUMENTS

| | | |
|---|---|---|
| 3,408,210 A | 10/1968 | Heyman |
| 3,542,560 A | 11/1970 | Tomarelli et al. |
| 4,104,290 A | 8/1978 | Koslowsky |
| 4,259,358 A | 3/1981 | Duthie |
| 4,742,081 A | 5/1988 | Stracher et al. |
| 4,866,040 A | 9/1989 | Stracher et al. |
| 4,992,470 A | 2/1991 | Nissen |
| 5,000,975 A | 3/1991 | Tomarelli |
| 5,028,440 A | 7/1991 | Nissen |
| 5,087,472 A | 2/1992 | Nissen |
| 5,167,957 A | 12/1992 | Webb, Jr. et al. |
| 5,171,442 A | 12/1992 | Nakshbendi |
| 5,223,285 A | 6/1993 | DeMichele et al. |
| 5,348,979 A | 9/1994 | Nissen et al. |
| 5,360,613 A | 11/1994 | Nissen |
| 5,431,928 A | 7/1995 | Saito et al. |
| 5,444,054 A | 8/1995 | Garleb et al. |
| 5,447,732 A | 9/1995 | Tanimoto et al. |
| 5,457,130 A | 10/1995 | Tisdale et al. |
| 5,601,860 A | 2/1997 | Lien et al. |
| 5,641,531 A | 6/1997 | Liebrecht et al. |
| 5,726,146 A | 3/1998 | Almada et al. |
| 5,780,451 A | 7/1998 | DeMichele et al. |
| 5,834,427 A | 11/1998 | Han et al. |
| 5,976,550 A | 11/1999 | Engel et al. |
| 6,031,000 A | 2/2000 | Nissen et al. |
| 6,060,446 A | 5/2000 | Zaloga et al. |
| 6,080,788 A | 6/2000 | Sole et al. |
| 6,103,764 A | 8/2000 | Nissen |
| 6,248,909 B1 | 6/2001 | Akimoto et al. |
| 6,291,525 B1 | 9/2001 | Nissen |
| 6,294,206 B1 | 9/2001 | Barrett-Reis et al. |
| 6,340,491 B1 | 1/2002 | Cain et al. |
| 6,420,342 B1 | 7/2002 | Hageman et al. |
| 6,468,987 B1 | 10/2002 | Demichele et al. |
| 6,475,539 B1 | 11/2002 | Dewille et al. |
| 6,521,591 B1 | 2/2003 | Smeets et al. |
| 6,596,767 B2 | 7/2003 | Masor et al. |
| 6,620,427 B2 | 9/2003 | Lasekan et al. |
| 6,660,258 B1 | 12/2003 | Tovey |
| 6,749,881 B2 | 6/2004 | Kataoka et al. |
| 7,332,178 B2 | 2/2008 | Byard et al. |
| 7,419,596 B2 | 9/2008 | Dueppen et al. |
| 7,435,442 B2 | 10/2008 | Servotte |
| 7,445,807 B2 | 11/2008 | Lockwood |
| 7,498,026 B2 | 3/2009 | Dahlqvist et al. |
| 7,517,850 B2 | 4/2009 | Holt |
| 7,696,241 B2 | 4/2010 | Li et al. |
| 7,795,204 B2 | 9/2010 | Gardiner et al. |
| 7,825,084 B2 | 11/2010 | Harris et al. |
| 8,217,077 B2 * | 7/2012 | Baxter et al. .................. 514/557 |
| 8,609,725 B2 | 12/2013 | Baxter et al. |

(Continued)

FOREIGN PATENT DOCUMENTS

AU    2006331950 A1    7/2007
CA       2632262 A1    7/2007

(Continued)

OTHER PUBLICATIONS

Aggarwal et al., "Suppression of the Nuclear Factor κB Activation Pathway by Spice-Derived Phytochemicals: Reasoning for Seasoning", Annals of the New York Academy of Science, vol. 1030, pp. 434-441 (2004).

(Continued)

*Primary Examiner* — Kevin E Weddington
(74) *Attorney, Agent, or Firm* — Calfee, Halter & Griswold LLP

(57) ABSTRACT

The present invention relates to methods for the prevention and treatment of chronic inflammatory diseases, cancer, and involuntary weight loss. In the practice of the present invention patients are enterally administered HMB alone or alternatively in combination with eicosapentaenoic (20:5 ω-3), FOS, carnitine and mixtures thereof. HMB may be added to food products comprising a source of amino-nitrogen enriched with large neutral amino acids such as leucine, isoleucine, valine, tyrosine, threonine and phenylalanine and substantially lacking in free amino acids.

20 Claims, 14 Drawing Sheets

(56) References Cited

U.S. PATENT DOCUMENTS

| | | |
|---|---|---|
| 2001/0008641 A1 | 7/2001 | Krotzer |
| 2002/0035965 A1 | 3/2002 | Uni et al. |
| 2003/0092609 A1 | 5/2003 | Larsen et al. |
| 2003/0165604 A1 | 9/2003 | Tsubaki et al. |
| 2003/0176514 A1 | 9/2003 | Fuhrmann et al. |
| 2003/0203070 A1 | 10/2003 | Lin et al. |
| 2004/0013787 A1 | 1/2004 | Theuer |
| 2004/0048925 A1 | 3/2004 | Wiley et al. |
| 2004/0071825 A1 | 4/2004 | Lockwood |
| 2004/0106678 A1 | 6/2004 | Dobbins et al. |
| 2004/0122210 A1 | 6/2004 | Thim et al. |
| 2004/0202770 A1 | 10/2004 | Cain et al. |
| 2004/0237466 A1 | 12/2004 | Grossmann et al. |
| 2004/0248771 A1 | 12/2004 | Raggi |
| 2005/0075280 A1 | 4/2005 | Larsen et al. |
| 2005/0106219 A1 | 5/2005 | Bortlik et al. |
| 2005/0215640 A1 | 9/2005 | Baxter et al. |
| 2005/0249650 A1 | 11/2005 | Damhuis et al. |
| 2006/0193961 A1 | 8/2006 | Shastri et al. |
| 2006/0204632 A1 | 9/2006 | Barrett-Reis et al. |
| 2006/0286210 A1 | 12/2006 | Rangavajla et al. |
| 2006/0293220 A1 | 12/2006 | Holt |
| 2007/0093553 A1 | 4/2007 | Baxter et al. |
| 2007/0125785 A1 | 6/2007 | Robinson et al. |
| 2007/0142469 A1 | 6/2007 | Thomas et al. |
| 2008/0031860 A1 | 2/2008 | Hageman |
| 2008/0058415 A1 | 3/2008 | Shulman et al. |
| 2008/0119552 A1 | 5/2008 | Navarro |
| 2008/0193624 A1 | 8/2008 | Shulman et al. |
| 2008/0194407 A1 | 8/2008 | Ashmead et al. |
| 2008/0254153 A1 | 10/2008 | Wang et al. |
| 2008/0260923 A1 | 10/2008 | Kratky et al. |
| 2008/0274230 A1 | 11/2008 | Johns et al. |
| 2008/0305531 A1 | 12/2008 | Lam et al. |
| 2008/0317886 A1 | 12/2008 | Sparkman |
| 2009/0087540 A1 | 4/2009 | Haschke et al. |
| 2009/0110674 A1 | 4/2009 | Loizou |
| 2009/0220637 A1 | 9/2009 | Roessle |
| 2009/0263367 A1 | 10/2009 | Foley |
| 2010/0179112 A1 | 7/2010 | Rathmacher et al. |
| 2011/0218244 A1 | 9/2011 | Kneller |
| 2011/0256301 A1 | 10/2011 | Kensler et al. |
| 2012/0141448 A1 | 6/2012 | De Ferra et al. |
| 2012/0177744 A1 | 7/2012 | Thomas |
| 2012/0177752 A1 | 7/2012 | Baxter |
| 2012/0178811 A1 | 7/2012 | Thomas |
| 2012/0189709 A1 | 7/2012 | Thomas |
| 2012/0189714 A1 | 7/2012 | Baxter |
| 2012/0189715 A1 | 7/2012 | Baxter |
| 2012/0189717 A1 | 7/2012 | Baxter |
| 2012/0196829 A1 | 8/2012 | Baxter |
| 2013/0011498 A1 | 1/2013 | Baxter |

FOREIGN PATENT DOCUMENTS

| | | |
|---|---|---|
| CN | 101785566 | 7/2010 |
| DE | 29707308 | 6/1997 |
| DE | 29709313 U1 | 9/1997 |
| DE | 10145818 C1 | 10/2002 |
| EP | 0036663 | 9/1981 |
| EP | 0367724 A1 | 9/1990 |
| EP | 0385859 A1 | 9/1990 |
| EP | 0756827 A2 | 2/1997 |
| EP | 698078 | 8/1997 |
| EP | 9739749 A2 | 10/1997 |
| EP | 0637239 B1 | 8/1999 |
| EP | 1968564 A2 | 9/2008 |
| EP | 2082738 A1 | 7/2009 |
| JP | 05503508 A | 6/1993 |
| JP | 7507569 T | 8/1995 |
| JP | 9121809 A | 5/1997 |
| JP | 11508282 T | 7/1999 |
| JP | 2001288107 A | 10/2001 |
| JP | 2002518440 A1 | 6/2002 |
| JP | 2002521428 A | 7/2002 |
| JP | 2003137790 A | 5/2003 |
| JP | 2009155336 | 7/2009 |
| JP | 5145033 | 11/2012 |
| JP | 5227182 B2 | 7/2013 |
| WO | 9011073 | 10/1990 |
| WO | 9406417 A1 | 3/1994 |
| WO | 9414429 A1 | 7/1994 |
| WO | 9804253 A1 | 2/1998 |
| WO | 9966917 A2 | 12/1999 |
| WO | 0006134 A2 | 2/2000 |
| WO | 01/77271 A2 | 10/2001 |
| WO | 03053456 | 7/2003 |
| WO | 03091214 | 11/2003 |
| WO | 2004064715 A2 | 8/2004 |
| WO | 2005000315 | 1/2005 |
| WO | 2005102301 A2 | 11/2005 |
| WO | 2006/062424 A2 | 6/2006 |
| WO | 2007066232 | 6/2007 |
| WO | 2007075605 A2 | 7/2007 |
| WO | 2009/143097 A1 | 11/2009 |
| WO | 2010068696 | 6/2010 |
| WO | 2011074995 | 6/2011 |
| WO | 2011156238 | 12/2011 |
| WO | 2012092035 | 7/2012 |
| WO | 2012097061 | 7/2012 |
| WO | 2013056048 | 4/2013 |
| WO | 2013170189 | 11/2013 |
| WO | 2013188258 | 12/2013 |

OTHER PUBLICATIONS

Barber et al., "The effect of an oral nutritional supplement enriched with fish oil on weight-loss in patients with pancreatic cancer," British Journal of Cancer, 1999, pp. 80-86, vol. 81, No. 1.

Barnes et al., "NF-kappa B: a pivotal role in asthma and a new target for therapy", Trends in Pharmacological Sciences, 1997, pp. 46-50, vol. 18.

Beck et al., "Anticachectic and Antitumor Effect of Eicosapentaenoic Acid and Its Effect on Protein Turnover," Cancer Research, vol. 51, pp. 6089-6093 (1991).

Brennan et al., "Nitrogen Metabolism in Cancer Patients," Cancer Treatment Reports, vol. 65, Supplemental 5, pp. 67-78 (1981).

Evans et al., "Expression and activation of protein kinase C in eosinophils after allergen challenge," Am J Physiol Lung Cell Mole Physiol, vol. 277, pp. 233-239 (1999).

Examination Report for Malaysian App. PI20082097 dated Jul. 29, 2011.

Examination Report from NZ Patent Application No. 568611, dated Apr. 13, 2010.

Flakoll et al., "Effect of b-hydroxy-b-methylbutyrate, arginine and lysine supplementation on strength, functionality, body composition, and protein metabolism in elderly women," Nutrition, vol. 20, pp. 445-451 (2004).

Fuller et al., "Decreasing male broiler mortality by feeding the leucine catabolite b-hydroxy-b-methylbutyrate," Poult. Sci., vol. 73, Supplemental 1, p. 93 (1994).

Gallagher et al., "B-hydroxy-b-methylbutyrate ingestion, Part 1: Effects on strength and fat free mass," Med. Sci. Sports Exerc, vol. 32, No. 12, pp. 2109-2115 (2000).

Gallagher et al., "b-hydroxy-b-methylbutyrate ingestion, Part II: effects on hematology, hepatic and renal function," Med. Sci. Sports Exerc., vol. 32, No. 12, pp. 2116-2119 (2000).

HMB, www.interactivenutrition.com, last visited Dec. 29, 2004.

International Search Report and Written Opinion for PCT/US2005/007951, dated Aug. 24, 2006.

International Search Report and Written Opinion for PCT/US2006/048303, dated May 6, 2008.

Jowko et al., "Creatine and b-hydroxy-b-methylbutyrate (HMB) additively increase lean body mass and muscle strength during a weight-training program", Nutrition, vol. 17, pp. 558-566 (2001).

Juven product information, http://abbottnutrition.com/Products/Juven, 5 pages, dated 2010.

Kaizen HMB, www.bodybuilding.com, last visited Dec. 29, 2004.

(56) References Cited

OTHER PUBLICATIONS

Kisner, "The Nutrition of the Cancer Patient," Cancer Treatment Reports, vol. 65, Supplemental 5, pp. 1-2 (1981).
Knitter et al., "Effects of b-hydroxy-b-methylbutyrate on muscle damage after a prolonged run," J. Appl. Physiol., vol. 89, pp. 1340-1344 (2000).
Lentsch et al., "Activation and Regulation of NFκB during Acute Inflammation," Clin. Chem. Lab. Med., vol. 37, No. 3, pp. 205-208 (1999).
Levenhangen et al., "Arginine, Lysine, and b-hydroxymethylbutyrate (HMB) Supplementation Enhances the Efficiency of Protein Synthesis in Elderly Females," Nutrition Week Abstracts, vol. 75, pp. 411S-412S (2002).
Macchi et al., "Influence of co-ingestion of glucose on b-hydroxy-b-methylbutyrate (HMB) metabolism in humans," FASEB J., p. A909 (1999).
Miller et al., "The effect of intensive training and b-hydroxy-b-methylbutyrate (HMB) on the physiological response to exercise in horses." FASEB J., p. A290 (1997).
Milne et al., "Do Routine Oral Protein and Energy Supplements Improve Survival and Reduce Length of Hospital Stay for Elderly People," Nutrition Week Abstracts, p. 412S (2002).
Moschini et al., "Effect of feeding b-hydroxy-b-methylbutyrate (HMB) on leucine and fat metabolism in mammary gland," FASEB J., p. A70 (1993).
Nissen et al., "b-hydroxy-b-methylbutyrate (HMB) supplementation in humans is safe and may decrease cardiovascular risk factors," J. Nutr., vol. 130, pp. 1937-1945 (2000).
Nissen et al., "Colostral milk fat percentage and pig performance are enhanced by feeding the leucine metabolite b-hydroxy-b-methylbutyrate to sows," J. Anim. Sci., vol. 72, pp. 2331-2337 (1994).
Nissen et al., "Effect of b-hydroxy-b-methylbutyrate (HMB) supplementation of strength and body composition of trained and untrained males undergoing intense resistance training," FASEB J., p. A287 (1996).
Nissen et al., "Effect of dietary supplements on lean mass and strength gains with resistance exercise: A meta analysis," J. Appl. Physiol., vol. 94, pp. 651-659 (2003).
Nissen et al., "Effect of feeding b-hydroxy-b-methylbutyrate (HMB) on body composition and strength of women," FASEB J., p. A150 (1997).
Nissen et al., "Effect of leucine metabolite b-hydroxy-b-methylbutyrate on muscle metabolism during resistance-exercise training," J. Appl. Physiol., vol. 81, No. 5, pp. 2095-2104 (1996).
Nissen et al., "Nutritional role of the leucine metabolite b-hydroxy-b-methylbutyrate (HMB)," J. Nutr. Biochem., vol. 8, pp. 300-311 (1997).
Nissen et al., "The effect of b-hydroxy-b-methylbutyrate on growth, mortality and cacass qualitiies of broiler chickens," Poultry Science, vol. 71, pp. 137-155 (1994).
Nissen et al., "The effects of the leucine catabolite, b-hydroxy-b-methylbutyrate (HMB), on the growth and health of growing lambs," J. Anim. Sci., p. 243 (1994).
Nonnecke et al., "Leucine and its Catabolites After Mitogen-Stimulated DNA Synthesis by Bovine Lymphocytes," J. Nutr., vol. 121, pp. 1665-1672 (1991).
Office Action for U.S. Appl. No. 11/025,466, dated Oct. 4, 2010.
Office Action for U.S. Appl. No. 11/025,466, dated Dec. 5, 2008.
Office Action for U.S. Appl. No. 11/025,466, dated Apr. 14, 2010.
Office Action for U.S. Appl. No. 11/025,466, dated Apr. 6, 2011.
Office Action for U.S. Appl. No. 11/025,466, dated May 5, 2008.
Office Action for U.S. Appl. No. 11/025,466, dated Jun. 25, 2009.
Office Action for U.S. Appl. No. 11/025,466, dated Aug. 17, 2007.
Office Action for U.S. Appl. No. 11/025,466, dated Sep. 8, 2011.
Office Action for U.S. Appl. No. 11/641,978, dated Oct. 20, 2009.
Office Action for U.S. Appl. No. 11/641,978, dated Feb. 26, 2008.
Office Action for U.S. Appl. No. 11/641,978, dated Mar. 3, 2009.
Office Action for U.S. Appl. No. 11/641,978, dated Jun. 7, 2010.

Office Action from Chinese Patent Application No. 200680047936.3, dated Feb. 24, 2011.
Office Action from Chinese Patent Application No. 200680047936.3, dated May 25, 2010.
Office action issued in Chinese App. No. 200580009569.0, dated Jun. 28, 2010.
Office action issued in Taiwan App. No. 094109357, dated Dec. 2, 2010.
Oliver et al., "Airway Smooth Muscle and Asthma," Allergology International, vol. 55, pp. 215-223 (2006).
Ostaszewski et al., "3-Hydroxy-3-Methylbutyrate (HMB) Fed in the Water Enhance Immune Response in Young Broilers," Abstract 96, . 25.
Ostaszewski et al., "The immunomodulating activity of dietary 3-hydroxy-3-methylbutyrate (HMB) in weaning pigs, "J. Anim. Sci., vol. 81, Supplemental 1, p. 136 (1998).
Ostaszewski et al., "The leucine metabolite 3-hydroxy-3-methylbutyrate (HMB) modifies protein turnover in muscles of laboratory rates and domestic chickens in vitro," J. Anim. Physiol. A. Anim. Nutr. 84, pp. 1-8 (2000).
Ostaszewski et al., "The effect of the leucine metabolite 3-hydroxy 3-methylbutyrate (HMB) on muscle protein synthesis and protein breakdown in chick and rat muscle," Journal of Animal Science, vol. 74, Supplemental 1, p. 138 (1996).
Ostaszewski et al., "Dietary supplementation of 3-hydroxy-3-methylbutyrate improved catch-up growth in underfed lambs," Ann. Zootech , vol. 43, p. 308 (1994).
Panton et al., "Effect of b-hydroxy-b-methylbutyrate and resistance training on strength and functional ability in the elderly," Medicine & Science in Sports & Exercise, p. S194 (1998).
Panton et al., "Nutritional supplementation of the leucine metabolite b-hydroxy-b-methylbutyrate (HMB) during resistance training," Nutrition, vol. 16, pp. 734-739 (2000).
Papet et al., "The effect of a high dose of 3-hydroxy-3-methylbutyrate on protein metabolism in growing lambs," Br. J. Nutr., vol. 77, pp. 885-896 (1997).
Abbott, "HMB (Beta-hydroxy-beta-methylbutyrate): A Scientific Review," Apr. 2010, pp. 1-34, XP002670332, available at http://abbottnutrition.com/downloads/resourcecenter/hmb-a-scientific-review.pdf (last accessed Apr. 9, 2012).
"Lite Protein Drinks," Database GNPD (Online) Mintel, Mar. 2000, XP002670334, available at www.gnpd.com.
"Lite Protein Drink Mixes with GlycerLEAN," Database GNPD (Online) Mintel, Feb. 2002, XP002670335, available at www.gnpd.com.
"Lean DynamX," XP 002670342, available at http://www.fitpage.de/produicte/pd-1330122620.htm?categoryId=181 (last accessed Feb. 24, 2012) (5 pages total).
International Search Report and Written Opinion for International Application No. PCT/US2011/066096, dated Mar. 14, 2012.
Meletis et al., "Natural Supports for Gaining and Maintaining Muscle Mass," Alternative and Complementary Therapies, pp. 257-263 (2005).
Zhang et al., "Occurrence of beta-hydroxy-beta-methylbutyrate in foods and feeds," Faseb Journal, vol. 8(4-5), p. A464 (Abstract 2685) (1994).
English translation of Notice of Rejection in Japanese Application No. 2000-555603, dated Mar. 6, 2012.
Non-final Office Action for U.S. Appl. No. 13/016,059, dated Mar. 23, 2012.
English translation of Office Action for Taiwan Patent Application No. 095147808, dated Mar. 21, 2012.
European Search Report for Application No. 11187274.3-1216, dated Feb. 15, 2012.
Kritchevsky, "An international symposium on cancer cachexia, cytokines, and EPA: Introduction," Nutrition, Elsevier Inc., U.S., vol. 12(1), p. S1 (1996).
Notice of Preliminary Rejection for Korean Application No. 10-2006-7022383, dated Feb. 13, 2012.
First Hearing Notice in Indian Application No. 1372/MUMNP/2008, dated Nov. 4, 2011.
Second Hearing Notice in Indian Application No. 1372/MUMNP/2008, dated Mar. 10, 2012.

(56) References Cited

OTHER PUBLICATIONS

Tisdale et al., "Inhibition of lipolysis and muscle protein degradation by epa in cancer cachexia," Nutrition, Elsevier Inc., U.S., vol. 12(1), pp. S31-S33 (1996).
Zuljdgeest-Van Leeuwen et al, "Inhibition of lipolysis by eicosapentaenoic acid in weight-losing cancer patients and healthy volunteers," Clinical Nutrition, Churchill Livingstone, London, G.B., vol. 17, p. 13 (1998).
Office Action issued in U.S. Appl. No. 13/016,005, dated Jun. 1, 2012.
Examiner's First Report in Australian Patent Application No. 2006331950, dated Apr. 19, 2012.
Anonymous, "Reload Dietary Supplements," Database GNPD (Online) Mintel, May 2010, XP002676291, available at www.gnpd.com.
Charbonneau, "Recent case histories of food product-metal container interactions using scanning electron microscopy-x-ray microanalysis," Scanning, vol. 19(7), pp. 512-518 (1997).
International Search Report and Written Opinion for International Application No. PCT/US2012/024817, dated Jun. 6, 2012.
International Search Report and Written Opinion for International Application No. PCT/US2012/023767, dated Jun. 6, 2012.
Montanari et al., "Quality of Organic Coatings for Food Cans: Evaluation Techniques and Prospects of Improvement," Progress in Organic Coatings, vol. 29(1-4), pp. 159-165 (1996).
Final Office Action for U.S. Appl. No. 13/016,041, dated Jun. 8, 2012.
English translation of Office Action issued in Chinese Patent Application No. 201110084963, dated Mar. 30, 2012.
De Maat et al., "Inflammation, Thrombosis and Atherosclerosis: Results of the Glostrup Study," Journal of Thrombosis and Haemostasis, 2003, vol. 1, No. 5, p. 950-957.
Choi et al., "Hematein inhibits atherosclerosis by inhibition of reactive oxygen generation and NF-kappaB-dependent inflammatory mediators in hyperlipidemic mice," Journal of Cardiovascular Pharmacology, 2003, vol. 42, No. 2, p. 287-295.
May, Patricia Eubanks, "Reversal of cancer-related wasting using oral supplementation with a combination of beta-hydroxy-beta-beta-methylbutyrate, arginine, and glutamine," American Journal of Surgery, vol. 183, No. 4, 2002, p. 471-479.
Sult, "Th1/Th2 Balance: A Natural Therapeutic Approach to Th2 Polarization in Allergy," Applied Nutritional Science Reports, 2003, p. 1-8.
AIDS Alert, 1999, vol. 14, No. 4, p. 41-43.
Clark et al., "Nutritional treatment for acquired immunodeficiency virus-associated wasting using beta-hydroxy beta-methylbutyrate, glutamine, and arginine: a randomized, double-blind, placebo-controlled study," Journal of Parenteral and Enteral Nutrition, May 2000, vol. 24, No. 3, p. 133-139.
Ostaszewski et al., "3-hydroxy-3-methylbuyric acid (HMB) in immunological reactions generated by nutritional allergy in guinea pigs," Veterinary Medicine, vol. 51, No. 2, 1995 (translation).
European Search Report and Opinion for Application No. 10186645.7-1216, dated Feb. 14, 2011.
Office Action from Indian Patent Application No. 1372/MUMNP/2008, dated Sep. 23, 2010.
Office Action issued in Taiwan Application No. 094109357, dated Jun. 24, 2011.
Office Action issued in Japanese Application No. 2007-504991, dated Jun. 21, 2011.
Office Action issued in Russian Application No. 2008129605, dated Jul. 5, 2011.
Examiner's First Report issued for New Zealand Patent Application No. 593182, dated Jun. 3, 2011.
Smith et al., "Attenuation of Proteasome-Induced Proteolysis in Skeletal Muscle by B-hydroxy-B-methylbutyrate in Cancer-Induced Muscle Loss," Cancer Research, 2005, vol. 65(1), p. 277-283.
Siu et al., "Id2 and p53 participate in apoptosis during unloading-induced muscle atrophy," Am. J. Physiol. Cell. Physiol., vol. 288, C1058-C1073 (2005).
Ferrando et al., "Prolonged bed rest decreases skeletal muscle and whole body protein synthesis," Am. J. Physiol. vol. 270, pp. E627-E633 (1996).
Kortebein et al., "Effect of 10 days of Bed Rest on Skeletal Muscle in Healthy Older Adults," JAMA, vol. 297, pp. 1772-1774 (2007).
Zarzhevsky et al., "Recovery of muscles of old rats after hindlimb immobilisation by external fixation is impaired compared with those of young rats," Exp. Gerontol., vol. 36, pp. 125-140 (2001).
Hanson et al., "Seven days of muscle re-loading and voluntary wheel running following hindlimb suspension in mice restores running performance, muscle morphology and metrics of fatigue but not muscle strength," Muscle Res. Cell Motil., vol. 31, pp. 141-153 (2010).
Ballard et al., "Effect of I-glutamine supplementation on impaired glucose regulation during intravenous lipid administration," Nutrition, vol. 12(5), pp. 349-354 (1996).
Clinical Infectious Diseases, vol. 25(2), p. 457 (1997).
Elam et al., "Effects of arginine and ornithine on strength, lean body mass and urinary hydroxyproline in adult males," The Journal of Sports Medicine and Physical Fitness, vol. 29(1), pp. 52-56 (1989).
Fligger et al., "Arginine Supplementation Increases Weight Gain, Depresses Antibody Production, and Alters Circulating Leukocyte Profiles in Preruminant Calves Without Affecting Plasma Growth Hormone Concentrations," J. Anim. Sci., vol. 75, pp. 3019-3025 (1997).
Jarowski et al., "Utility of Fasting Essential Amino Acid Plasma Levels in Formulation of Nutritionally Adequate Diets III: Lowering of Rat Serum Cholesterol Levels by Lysine Supplementation," Journal of Pharmaceutical Sciences, vol. 64(4), pp. 690-691 (1975).
Office Action issued in Chinese Application No. 200580009596.0, dated Jun. 9, 2011.
Office Action issued in Japanese Application No. 2000-555603, dated Jan. 12, 2010.
Office Action issued in Japanese Application No. 2000-555603, dated Feb. 15, 2011.
Office Action issued in Japanese Application No. 2000-555603, dated Oct. 25, 2011.
Office Action issued in Philippines Application No. 12006501893, dated Oct. 11, 2011.
Campbell, et al., "Allergic humans are hyporesponsive to a CXCR3 ligand-mediated Th1 immunity-promoting loop," The FASEB Journal, vol. 18, pp. 329-331 (2004).
Hauber, et al., "Expression of interleukin-4, interleukin-9 and interleukin-13 in peripheral blood mononuclear cells of cystic fibrosis patients with and without allergy," EXCLI Journal, vol. 5, pp. 209-216 (2006).
Office Action issued in Canadian Patent Application No. 2,560,042, dated Nov. 14, 2011.
Office Action issued in Russian Application No. 2008129605, dated Aug. 12, 2011.
Office Action issued in U.S. Appl. No. 11/025,466, dated Feb. 10, 2012.
Office Action issued in U.S. Appl. No. 13/016,005, dated Jan. 27, 2012.
Office Action issued in U.S. Appl. No. 13/016,041, dated Feb. 3, 2012.
Rham et al., "Role of Ionic Environment in Insolubilization of Whey Protein During Heat Treatment of Whey Products," Journal of Dairy Science, vol. 67(5), pp. 939-949 (1984).
Non-final Office Action for U.S. Appl. No. 13/151,911, dated Apr. 19, 2012.
Office Action issued in Philippines Patent Application No. 1-2008-501331, dated Apr. 4, 2012.
Office action issued in Chinese Patent Application No. 200580009596, dated Mar. 1, 2012.
Second Office Action issued in Japanese Patent Application No. 2007-504991, dated Mar. 13, 2012.
Examination Report issued in New Zealand Patent Application No. 599371, dated Apr. 20, 2012.
International Preliminary Report on Patentability for International Application No. PCT/US2011/022938, dated Jan. 25, 2012.
International Preliminary Report on Patentability for International Application No. PCT/US2011/022947, dated Feb. 15, 2012.

(56) References Cited

OTHER PUBLICATIONS

Tanaka et al., "Effects of the novel Foxo 1 inhibitor AS1708727 on plasma glucose and triglyceride levels in diabetic db/db mice," European J. of Pharmacology (2010) vol. 645, pp. 185-191.
Wang et al., "Effect of Curcumin on Airway Inflammation and the Expression of Nuclear Factor kappa-B in Rats with Asthma", Chinese Journal of Clinical Rehabilitation, vol. 9, No. 11, p. 104 Mar. 21, 2005.
Wang et al., "Effect of Curcumin on Aiway Collagen Deposition and the Expression of Transformation Growth Factor beta-1 in Rats with Asthma", Journal of Clinical Pediatrics, vol. 23, No. 9, p. 659 (abstract).
Zdychova et al., "Emerging role of Akt Kinase/Protein Kinase B signaling in pathophysiology of diabetes and its complications," Physiol. Res. vol. 54(1), pp. 1-16 (2005).
De Los Reyes, et al., "Overview of resistance training diet, hormone replacement and nutritional supplements on age-related sarcopenia—a mini review", Research Communications in Molecular Pathology and Pharmacology, vol. 113-114, pp. 159-170 (2003).
Moschini, et al. "Effect of feeding b-hydroxy-b-methylbutyrate (HMB) on leucine and fat metabolism in mammary gland." FASEB J. 7 (1993), Abstract 407. Office Action from U.S. Appl. No. 13/347,877 dated Apr. 5, 2013.
Elias, et al., "New insights into the pathogenesis of asthma", Journal of Clinical Investigation, vol. 111, No. 3 (Feb. 2003) pp. 291-297.
Office Action from U.S. Appl. No. 13/347,877 dated Apr. 5, 2013.
Office Action in U.S. Appl. No. 13/347,750 dated Feb. 25, 2013.
Office Action in U.S. Appl. No. 13/347,757 dated Jul. 30, 2012.
Response to Restriction/Election Requirement from U.S. Appl. No. 13/347,757 dated Aug. 30, 2012.
Restriction Requirement in U.S. Appl. No. 10/810,762 dated Nov. 24, 2006.
Response to Restriction Requirement in U.S. Appl. No. 10/810,762 dated Dec. 18, 2006.
Office Action in U.S. Appl. No. 10/810,762 dated Mar. 22, 2007.
Response under 37 CFR 1.111 for U.S. Appl. No. 10/810,762 dated Sep. 24, 2007.
Office Action in U.S. Appl. No. 10/810,762 dated Mar. 18, 2008.
Examiner Initiated Interview Summary and Notice of Abandonment for U.S. Appl. No. 10/810,762 dated Sep. 29, 2008.
Restriction Requirement for U.S. Appl. No. 11/025,466 dated Apr. 9, 2007.
Response to Restriction Requirement for U.S. Appl. No. 11/025,466 dated Apr. 19, 2007.
Response to Office Action for U.S. Appl. No. 11/025,466 dated Jun. 17, 2011.
Response under CFR1.111 for U.S. Appl. No. 11/025,466 dated Jan. 17, 2008.
Response under CFR1.111 for U.S. Appl. No. 11/025,466 dated Sep. 5, 2008.
Response Under 37 CFR 1.111 for U.S. Appl. No. 11/025,466 dated Jun. 2, 2009.
Response under 37 CFR 1.111 for U.S. Appl. No. 11/025,466 dated Dec. 18, 2009.
Response after RCE for U.S. Appl. No. 11/025,466 dated Aug. 6, 2010.
Response to Office Action from U.S. Appl. No. 11/025,466 dated Feb. 3, 2011.
Amendment and Response After RCE for U.S. Appl. No. 11/025,466 dated Dec. 8, 2011.
Amendment and Response to Ex Parte Quayle Action in U.S. Appl. No. 11/025,466 dated Feb. 14, 2012.
Notice of Allowance for U.S. Appl. No. 11/025,466 dated Mar. 22, 2012.
Response to Restriction Requirement in U.S. Appl. No. 11/641,978 dated Jan. 15, 2008.
Response to office action for U.S. Appl. No. 11/641,978 dated Jun. 26, 2008.
Response to Office Action for U.S. Appl. No. 11/641,978 dated Nov. 5, 2008.
Amendment filed with RCE for U.S. Appl. No. 11/641,978 dated Aug. 31, 2009.
Response to Office Action for U.S. Appl. No. 11/641,978 dated Jan. 19, 2010.
Interview Summary for U.S. Appl. No. 11/641,978 dated Mar. 26, 2010.
Response after Rce for U.S. Appl. No. 11/641,978 dated Sep. 13, 2010.
Office action for U.S. Appl. No. 11/641,978 dated Sep. 14, 2012.
Response in U.S. Appl. No. 11/641,978 dated Feb. 14, 2013.
Restriction Requrement in U.S. Appl. No. 13/347,750 dated Nov. 6, 2012.
Response to Restriction/Election Requirement from U.S. Appl. No. 13/347,750 dated Dec. 6, 2012.
Response to Office Action from U.S. Appl. No. 13/347,757 dated Feb. 28, 2013.
Office Action for U.S. Appl. No. 13/347,774 dated Oct. 4, 2012.
Response to Office Action from U.S. Appl. No. 13/347,774 dated Feb. 4, 2013.
Office Action for U.S. Appl. No. 11/641,978 dated Oct. 20, 2009.
Exam Report issued in Philippines Application No. 12006501893 dated Mar. 22, 2013.
Office Action from U.S. Appl. No. 13/348,026 dated Nov. 23, 2013.
Notice of Allowance for Canadian Application No. 2,560,042 dated Sep. 24, 2012.
Office action from Canadian Application No. 2,632,262 dated Nov. 26, 2012.
English translation of relevant portion of Third Office Action from Chinese Application No. 200680047936.3 dated May 30, 2012.
Notification to Grant Patent for Chinese Application No. 200680047936.3 dated Mar. 4, 2013.
English translation of Second Office action for Chinese Application No. 201110084963 dated Dec. 21, 2012.
English summary of First Expert Report in EC Appl. No. SP-06-6873 dated May 7, 2012.
Communication in EP Application No. 11187274.3 dated Aug. 6, 2012.
Office Action in EP Application No. 10186645.7-1216 dated Nov. 7, 2012.
Extended European Search Report for EP 12382138.1 dated Oct. 16, 2012 (13 pages).
English translation of relevant portions of Israeli Office Action for Application No. 178039 dated Aug. 6, 2012.
Notice of Allowance from Japanese Application No. 2008-547409 dated Feb. 26, 2013, granting 13 claims (English Translation of Granted Claims attached.
Berger, "Science Commentary: Th1 and Th2 responses: what are they?" BMJ (Aug. 12, 2000), vol. 321, p. 424.
Office Action from U.S. Appl. No. 13/347,956 dated Apr. 18, 2013.
Office Action in Japanese Application No. 2008-547409 dated Jun. 5, 2012.
Examiner's Decision of Rejection from Japanese Application No. 2008-547409 dated Sep. 25, 2012.
Notice of Allowance from Japanese Application No. 2008-547409 dated Feb. 26, 2013, granting 13 claims (English Translation of Granted Claims attached).
English translation of Notice of Final Rejection for Korean Application No. 10-2006-7022383 dated Nov. 7, 2012.
First Office Action from Mexican Appl. No. PA/a/2006/010922 dated Aug. 31, 2011.
Second Office Action from Mexican Appl. No. PA/a/2006/010922 dated Apr. 17, 2012.
Office Action from Mexican Appl. No. PA/a/2006/010922 dated Oct. 24, 2012.
Office Action in Mexican Appl. No. MX/a/2010/012154 dated Apr. 30, 2012.
Office Action in Mexican Appl. No. MX/a/2010/012154 dated Oct. 5, 2012.
Office Action in Mexican Appl. No. MX/a/2010/012154 dated Mar. 12, 2013.
Examination Report issued in New Zealand Application No. 599371 dated Dec. 5, 2012.

(56) References Cited

OTHER PUBLICATIONS

English translation of Office Action rejecting Taiwan patent application No. 095147808 dated Nov. 8, 2012.
Allergy Online Clinic "Clinical Aspect in Th1 and Th2 Balance," http://allergyclinic.wordpress.com/2012/04/01/clinical-aspect-in-th1-and-th2-balance/; posted on Apr. 1, 2012, accessed on Dec. 21, 2012, 14 pages.
Alon et al., "Supplementing with beta-hydroxy-beta-methylbuturate (HMB) to build and maintain muscle mass: a review", Research Communications in Molecular Pathology and Pharmacology (2002) vol. 111, No. 1-4, pp. 139-151.
Barnes et al., "The cytokine network in asthma and chronic obstructive pulmonary disease", Journal of Clinical Investigation, vol. 118, No. 11 Nov. 2008, pp. 3546-3556 (7952).
Barnes, "Pathophysiology of Allergic Inflammation," Immunological Reviews (2011), vol. 242, pp. 31-50.
Biocompare "Th1 and Th2 Balance, Regulation and Involvement in Disease," http://www.biocompare.com/Application Notes/43518-Th1-and-Th2-Balance-Regulation-and-Involvement-in-Disease/ posted on Apr. 24, 2006, accessed on Feb. 5, 2013 8 pages.
Burke, R., "Inhibition of mitogen-activated protein kinase and stimulation of Akt kinase signaling pathways: Two approaches with therapeutic potential in the treatment of neurodegenerative disease," Pharm. and Therap., vol. 114 (3), pp. 261-277 (2007) (10372).
Cousins, et al., "Therapeutic approaches for control of transcription factors in allergic disease," J Allergy Clin Immunol, (Apr. 2008), vol. 21, No. 4 pp. 803-809.
Damjanac et al., "Dissociation of Akt/PKB and ribosomal S6 kinase signaling markers in a transgenic mouse model of Alzheimer's disease," Neurobiology of Disease, vol. 29(2), pp. 354-367 (2008).
Fisher, et al. "Effects of Oxandrolone and L-Glutamine on Body Weight, Body Cell Mass, and Body Fat in Patients with HIV Infection—Preliminary Analysis." Nutrition (1997), vol. 13, No. 3, Abstract P-12, p. 279.
Hawkley, et al., "Stress and the aging immune system," Brain, Behavior and Immunity 18 (2004), pp. 114-119.
Hooper, "Overview of NFκB Signaling" http://www.abcam.com/index.html? Pageconfig+respirce&rid=112255&pid=10629; accessed on Dec. 21, 2012 4 pages.
Kaslow, "Immune Restoration," http://www.drkaslow.com/html/immune_restoration.html; accessed on Dec. 21, 2012 9 pages.
Komasio et al., "Beta hydroxy-beta-methylbutyrate (HMB) Stimulates myogenic cell proliferation, differentiation and survival via the MAPK/ERK and P13K/Akt pathways," Biochemica et Biophysica Acta (2009), vol. 1793, No. 5, pp. 755-763.
Lucey et al., "Type 1 and Type 2 Cytokine Dysregulation in Human Infectious, Neoplastic, and Inflammatory Diseases", Clinical Microbiology Reviews, Oct. 1996, pp. 532-562.
MacDonald et al., "Understanding and Managing Cancer Cachexia,", Journal of the American College of Surgeons, vol. 197(1), 2003, pp. 143-161.
Merck Manual, "Starving and Wasting," 16th Ed., pp. 919-920 (1995)—submitted in Japanese and English explanation.
Nawa et al., "A novel Akt/PKB-interacting protein promotes cell adhesion and inhibits familial amyotrophic lateral sclerosis-linked mutant SOD 1-induced neuronal death via inhibition of PP2A mediated desphophorylaton of Akt/PKB," Cellular Signaling (2008) vol. 20, pp. 493-5057.
Nevala, et al., "Evidence of Systemic Th2-Driven Chronic Inflammation in Patients with Metastatic Melanoma," Clin Can Res (2009) vol. 15, pp. 1931-1939.
Orange Juice Facts, downloaded from www.orangejuicefacts.com/nutrition.html downloaded on Nov. 28, 2012 pp. 1-3 of 3.
Ostasweski et al., "Kwas 3-hydroksy-3-metylomastlowy (HMB) w reakcjach immunoloiogicznych alergii pokarmowej u swinek morskich", medycyna waterynaryjna, 1995 (2), pp. 100-102 [English abstract provided].
Portal, et al., "Effect of HMB supplementation on body composition, fitness, hormonal profile and muscle damage indices," J. of Pediatric Endocrinology & Metabolism (Jul. 7, 2010) vol. 23, No. 7, pp. 641-650.
Office Action for U.S. Appl. No. 13/347,757 dated Dec. 6, 2012.
Office Action from U.S. Appl. No. 13/347,985 dated Feb. 14, 2013.
Perkins et al., "Good cop, bad cop: the different faces of NF-kB," Cell Death and Differentiation, vol. 13, pp. 759-772 (2006).
Peterson et al., "Enhancement of cellular and humoral immunity in young broilers by the dietary supplementation of b-hydroxy-b-methylbutyrate," Immunopharmacology and Immunotoxicity, vol. 21, No. 2, pp. 307-330 (1999).
Peterson et al., "In Vitro Exposure with B-Hydroxy-B-Methylbutyrate Enhances Chicken Macrophage Growth and Function," Vetrinary Immunology and Immunopathology, vol. 67, pp. 67-78 (1999).
Porter et al., "Sustained NFAT Signaling Promotes a Th1-like Pattern of Gene Expression in Primary Murine CD4+ T Cells," Journal of Immunology, vol. 168, pp. 4936-4945 (2002).
Rathbacher et al., "Safety of a nutritional mixture of b-hydroxy-b-methylbutyrate (HMB), glutamine and arginine in healthy young adults and patients with AIDS," JPEN 23(1): S10 (1999).
Rathmacher et al., "The effect of the leucine metabolite b-hydroxy-b-methylbutyrate on lean body mass and muscle strength during prolonged bedrest," FASEB J., p. A909, (2001).
Rothmacher et al., "Supplementation with a combination of beta-hydroxy-beta-methylbutyrate (HMB), arginine, and glutamine is safe and could improve hematological parameters," Journal of Parenteral and Enternal Nutrition, vol. 28, No. 2, p. 6575 (2004).
Sandberg et al., "Effect of b-hydroxy-b-methylbutyrate on the physiological response to exercise and conditioning in horses," Journal of Animal Science, p. 198 (1997).
Sandberg et al., "The Effect of Intensive Training and b-hydroxy-b-methylbutyrate (HMB) on Muscle Glycogen concentration in the Horse," Journal of Animal Science, vol. 76, Supplemental 1, p. 175 (1998).
Siwicki et al., "Immunomodulating effect of 3-hydroxy-3-methylbutyrate (HMB) on the nonspecific cellular and humaoral defense mechanisms in rainbow trout (*Oncorhynchus nykiss*)," Journal of Animal Science, vol. 76, Supplemental 1, p. 137, (1998).
Siwicki et al., "In Vitro Effects of 3-Hydroxy-3-methylbutyrate (HMB) on measures of immune function and immunocompetence in fish," Journal of Animal Science, vol. 76, Supplemental 1, p. 136 (1998).
Siwicki et al., "Influence of 3-hydroxy-3-methylbutyrate on specific cellular immune response after in vitro and in vivo immunization with *Yersinia ruckeri* antifen," Journal of Animal Science, vol. 76, Supplemental 1, p. 136 (1998).
Smith et al., "Mechanisms of the attentuation of proteolysis-inducing factor stimulated protein degradation in muscle by beta-hydroxy-beta-methylbutyrate." Cancer Research, pp. 8731-8735 (2004).
Talleyrand et al., "Effect of feeding b-hydroxy-b-methylbutyrate on immune function in stressed calves," FASEB J, p. A951 (1994).
Talleyrand et al., "Uptake and output of the leucine metabolite b-hydroxy-b-methylbutyrate (HMB) across the legs of pigs," FASEB J., p. A71 (1993).
Tisdale et al., "Inhibition of Weight Loss by w-3 Fatty Acids in an Experimental Cachexia Model," Cancer Research, vol. 50, pp. 5002-5026 (1990).
Van Koevering et al., "Effect of b-hydroxy-b-methylbutyrate on the health and performance of shipping-stressed calves," The Oklahoma State Animal Science Research Report, pp. 312-316 (1993).
Van Koevering et al., "Oxidation of leucine and a-ketoisocaproate to b-hydroxy-b-methylbutyrate in vivo," American Journal of Physiology, pp. E27-E31 (1992).
Vukovich et al., "Body composition of 70-year-old adults responds to dietary beta-hydroxy beta-methylbutyrate similarly to that of young adults," Journal of Nutrition, vol. 131, No. 7, pp. 2049-2052 (2001).
Vukovich et al., "Effect of beta-hydroxy beta-methylbutyrate on the onset of blood lactate accumulation and VO2 peak in endurance-trained cyclists," J. Strength & Conditioning Res., vol. 15, No. 4, pp. 491-497 (2001).

(56) References Cited

OTHER PUBLICATIONS

Vukovich et al., "The effect of dietary b-hydroxy-b-methylbutyrate (HMB) on strength gains and body composition in older adults," FASEB J., p. A376 (1997).

Williams et al., "Effect of a specialized amino acid mixture on human collagen deposition," Annals of Surgery, vol. 236, No. 3, pp. 369-375 (2002).

Witte et al., "Nutritional abnormalities contributing to cachexia in chronic illness," International Journal of Cardiology, vol. 85, pp. 23-31 (2002).

Zachwieja et al., "Effect of the Leucine Metabolite b-hydroxy-b-rnethylbutyrate on muscle protein synthesis during prolonged bedrest," FASEB Abstracts, p. A1025 (1999).

Zhang et al., "Change in plasma b-hydroxy-b-methylbutyrate (HMB) by feeding leucine, a-ketiusicaoriate and isovaleric acid to pigs," FASEB J., p. A392 (1993).

Examination Report for Vietnam Application No. 1-2006-01765, issued Aug. 18, 2011.

Andela, et al., "NFkappaB: a pivotal transcription factor in prostate cancer metastasis to bone," Clinical Orthopaedics and Related Research, vol. 415S, pp. S75-S85 (2003).

Andrews, et al. "A rapid micropreparation technique for extraction of DNA-binding proteins from limiting numbers of mammalian cells," Nucleic Acids Res., vol. 19, No. 9, p. 2499 (1991).

Battaini, "Protein kinase C isoforms as therapeutic targets in nervous systemdisease states," Pharmacological Research, vol. 44, No. 5, pp. 353-361 (2001).

Bibby et al., "Characterization of a transplantable adenocarcinoma of the mouse colon producing cachexia in recipient animals," J. Natl. Cancer Inst., vol. 78, No. 3, pp. 539-546 (1987).

Carter, "Protein Kinase C as a drug target: Implications for drug or diet prevention and treatment of cancer," Current Drug Targets, vol. 12 , No. 2, pp. 163-183 (2000).

Coffman et al. "Syntheses by Free-radical Reactions. V. A New Synthesis of Carboxylic Acids", J. Am. Chem. Soc., vol. 80, pp. 2282-2887 (1958).

Delfino, "Hormonal Regulation of the NF-kappaB signaling pathway," Molecular and Cellular Endocrinology, vol. 157, Nos. 1-2, pp. 1-9 (1999).

Dentener et al., "Systemic anti-inflammatory mediators in COPD: increase in soluble interleukin 1 receptor II during treatment of exacerbations," Thorax, vol. 56, No. 9, pp. 721-726 (2001).

Examiner's 2nd Report issued in New Zealand Application No. 568611, dated Jun. 3, 2011.

Fenteany et al., "Lactacystin, proteasome function and cell fate," J. Biol. Chem., vol. 273, No. 15, pp. 8545-8548 (1998).

Frank, "Potential new medical therapies for diabetic retinopathy: protein kinase C inhibitors," American Journal of Opthamology, vol. 133, No. 5, pp. 693-698 (2002).

Goekijan, "Protein kinase C in the treatment of disease: Signal transduction pathways, inhibitors, and agents in development," Current Medical Chemistry, vol. 6, No. 9, pp. 877-903 (1999).

Gomes-Marcondes et al., "Development of an in-vitro model system to investigate the mechanism of muscle protein catabolism induced by proteolysis-inducing factor," British Journal of Cancer, vol. 86, No. 10, pp. 1628-1633 (2002).

Jagoe, "What do we really know about the ubiquitin-proteasome pathway in muscle atrophy?" Current Opinion in Clinical Nutrition and Metabolic Care, vol. 4, No. 3, pp. 183-190 (2001).

Meier, "Protein kinase C activation and its pharmacological inhibition in vascular disease," Vascular Medicine, vol. 5, No. 3, pp. 173-185 (2000).

Moscat, "NF-kappaB activation by protein kinase C isoforms and B-cell function," Embo Reports, vol. 4, No. 1, pp. 31-36 (2003).

O'Brianne et al., "The tumor promoter receptor protein kinase C: A novel target for chemoprevention and therapy of human colon cancer," Prog. Clin. Bio. Res., vol. 391, pp. 117-120 (1995).

Orino et al., "ATP-dependent reversible association of proteasomes with muttiple protein components to form 26S complexes that degrade ubiquitinated proteins in human HL-60 cells," FEBS Letters, vol. 284, No. 2, pp. 206-210 (1991).

Ostaszewski et al., "3-hydroxy-3-methylbutyrate and 2-oxoisocaproate effect body composition and cholestreol concentration in rabbits." Journal of Animal Physiology and Animal Nutrition, vol. 79, pp. 135-145 (1998).

Schols, "Evidence for a relation between metabolic derangements and increased levels of inflammatory mediators in a subgroup of patients with chronic obstructive pulmonary disease," Thorax, vol. 51, No. 8, pp. 819-824 (1996).

Schols, "Pulmonary cachexia," International Journal of Cardiology, vol. 85, No. 1, pp. 101-110 (2002).

Smart et al, "Polyclonal and allergen-induced cytokine responses in adults . . . " Journal of Allergy and Clinical Immunology, vol. 110, pp. 45-46 (2002).

Smith et al., "Effect of a cancer cachectic factor on protein synthesis/degradation in murine C2C12 myoblasts: modulation by eicosapentaenoic acid," Cancer Research, vol. 59, No. 21, pp. 5507-5513 (1999).

Smith et al., "Signal transduction pathways involved in proteolysis-inducing factor induced proteasome expression in murine myotubes," British Journal of Cancer, vol. 89, No. 9, pp. 1783-1788 (2003).

Takabatake et al., "Circulating leptin in patients with chronic obstructive pulmonary disease," American Journal of Respiratory and Critical Care Medicine, vol. 159, pp. 1215-1219 (1999).

Teixeira et al., "The role of interferon-c on immune and allergic responses . . . ," Mem. Inst. Oswaldo Cruz, vol. 100, pp. 137-144 (2005).

Todorov et al., "Characterization of a cancer cachectic factor," Nature, vol. 379, No. 6567, pp. 739-742 (1996).

Todorov et al., "Induction of muscle protein degradation and weight loss by a tumor product," Cancer Research, vol. 56, No. 6, pp. 1256-1261 (1996).

Toker, "Signaling through protein kinase C," Frontiers in Bioscience, vol. 3, pp. 1134-1147 (1998).

Van Koevering et al., "Effects of b-hydroxy-b-methylbutyrate on performance and carcass quality of feedlot steers." Journal of Animal Science, vol. 72, pp. 1927-1935 (1994).

Waalkes, "A fluorometric method for the estimation of tyrosine in plasma and tissues," Journal of Laboratory and Clinical Medicine, vol. 50, No. 5, pp. 733-736 (1957).

Watchorn et al., "Proteolysis-inducing factor regulates hepatic gene expression via the transcriptionfactor NF-kappaB and STST3," FASEB Journal, vol. 15, No. 3, pp. 562-564 (2001).

Whitehouse et al., "Induction of protein catabolism in myotubes by 15(S)-hydroxyeicosatetraenoic acid through increased expression of the ubiquitin-proteasome pathway," British Journal of Cancer, vol. 89, No. 4, pp. 737-745 (2003).

Whitehouse et al., "Increased expression of the ubiquilin-proteosome pathway in murine myotubes by proteolysis-inducing factor (PIF) is associated with activation of the transcription factor NF-kappaB," British Journal of Cancer, vol. 89, No. 6, pp. 1116-1122 (2003).

Wolf et al., "The mitogen-activated protein kinase signaling cascade: from bench to bedside," IMAJ, vol. 4, No. 8, pp. 641-647 (2002).

Haumann, "Structured Lipids Allow Fat Tailoring," International News on Fats, Oils, and Related Materials, vol. 8(10), pp. 1004-1011 (1997).

Ho et al., "Antioxidants, NFkappaB activation and diabetogenesis," Proceedings of the Society for Experimental Biology and Medicine, vol. 222, No. 3, pp. 205-213 (1999).

Kutsuzawa et al., "Muscle energy metabolism and nutritional status in patients with chronic obstructive pulmonary disease," American Journal of Respiratory and Critical Care Medicine, vol. 152, No. 2, pp. 647-652 (1995).

Lorite et al., "Activation of a TP-ubiquita-dependent proteolysis in skeletal muscle in vivo and murine myoblasts in vitro by a proteolysis-inducing factor (PIF)," British Journal of Cancer, vol. 85, No. 2, pp. 297-302 (2001).

Merck Index No. 1862, 2003.

Merck Index No. 5198, 2003.

Merck Index No. 7355, 2003.

Merck Index No. 9908, 2003.

(56) References Cited

OTHER PUBLICATIONS

Merck Index No. 9975, 2003.
International Search Report and Written Opinion for PCT/US2011/039170, dated Aug. 3, 2011.
European Search Report for App. 10186645.7-1216, dated Feb. 14, 2011.
Golubitskii et al., "Stability of Ascorbic Acid in Aqueous and Aqueous-Organic Solutions for Quantitative Determination," J. Anal Chem., vol. 62, No. 8, pp. 742-747 (2007).
Puspitasari et al., "Calcium Fortification of Cottage Cheese with Hydrocolloid Control of Bitter Flavor Defects," J. Dairy Sci., vol. 74, pp. 1-7 (1991).
Toelstede et al., "Sensomics Mapping and Identification of the Key Bitter Metabolites in Gouda Cheese," J Agric Food Chem, vol. 56, pp. 2795-2804 (2008).
Toelstede et al., "Quantitative Studies and Taste Re-Engineering Experiments Toward the Decoding of the Nonvolatile Sensometabolome of Gouda Cheese," J Agric Food Chem, vol. 56, pp. 5299-5307 (2008).
Tordoff et al., "Vegetable Bitterness is Related to Calcium Content," Appitite, vol. 52, pp. 498-504 (2009).
Engel et al., "Evolution of the Composition of a Selected Bitter Camembert Cheese During Ripening: Release and Migration of Taste-Active Compounds," J. Agric Food Chem, vol. 49, pp. 2940-2947 (2001).
Engel et al., "Evolution of the Taste of a Bitter Camembert Cheese During Ripening: Characterization of a Matrix Effect," J. Agric Food Chem., vol. 49, pp. 2930-2939 (2001).
Gacs et al., "Significance of Ca-Soap Formation for Calcium Absorption in the Rat," Gut, vol. 18, pp. 64-68 (1977).
Technical Information: HEC-3000 10-Step Water Purification System, Home Environment, (2001).
Case Study: Water Purification Plant Installed at New UK Power Station, Filtration & Separation (Dec. 2004).
Kreider et al., "Effect of Calcium Beta-Hydroxy-Beta-Methylbutyrate (HMB) Supplementation During Resistance-Training on Markers of Catabolism, Body Composition and Strength," International Journal of Sports Medicine, vol. 20, No. 8, pp. 503-509 (Nov. 1, 1999).
International Search Report and Written Opinion for PCT/US2011/022928 (May 23, 2011).
International Search Report and Written Opinion for PCT/US2011/022932 (May 23, 2011).
International Search Report and Written Opinion for PCT/US2011/022938 (May 23, 2011).
International Search Report and Written Opinion for PCT/US2011/022947 (May 23, 2011).
International Search Report and Written Opinion for PCT/US2011/022935 (May 23, 2011).
Office Action in U.S. Appl. No. 13/990,726 dated Feb. 4, 2014.
Baier et al., "Year-long Changes in Protein Metabolism in Elderly Men and Women Supplemented with a Nutrition Cocktail of beta-hydroxy-beta-methylbutyrate (HMB), L-Arignine, and L-Lysine," JPEN (2009), vol. 33, No. 1, pp. 71-82 (Absract Only).
Hudson et al., "Review—Maintaining muscle mass during extended disuse: aestivating frogs as a model species," The Journal of Experimental Biology, 205, 2297-2303 (2002).
Wilson et al., "Review—Effects of beta-hydroxy-beta-methylbutyrate (HMB) on exercise performance and body composition across varying levels of age, sex and training experience: A Review," Nutrition and Metalbolism, 2008 5:1, Jan. 2008 (17 pages).
Office Action for U.S. Appl. No. 11/641,978 dated May 21, 2013.
Response to Office Action with Declaration and Exhibits for U.S. Appl. No. 13/347,750 dated May 24, 2013.
Final Office Action for U.S. Appl. No. 13/347,757 dated Jun. 10, 2013.
Amendment for U.S. Appl. No. 13/347,757 dated Aug. 12, 2013.
Office Action for U.S. Appl. No. 13/347,774 dated Apr. 25, 2013.
Response after Final Action for U.S. Appl. No. 13/347,774 dated Jun. 25, 2013.
RCE for U.S. Appl. No. 13/347,774 dated Aug. 12, 2013.
Advisory Action for U.S. Appl. No. 13/347,774 dated Aug. 12, 2013.
Restriction Requirement for U.S. Appl. No. 13/347,978 dated May 10, 2013.
Response to Restriction Requirement for U.S. Appl. No. 13/347,978 dated Jun. 10, 2013.
Request for Reconsideration with Terminal Disclaimer for U.S. Appl. No. 13/348,026 dated May 23, 2013.
Notice of Allowance for U.S. Appl. No. 13/348,026 dated Aug. 2, 2013.
Office Action for U.S. Appl. No. 13/348,035 dated Jun. 6, 2013.
Amendment for U.S. Appl. No. 13/347,877 dated Aug. 5, 2013.
Response to Office Action for U.S. Appl. No. 13/347,956 dated Jul. 17, 2013.
Office Action for Canadian Application No. 2,807,787 dated Apr. 15, 2013.
Decision on Rejection for CN Application No. 201110084963 dated Jul. 11, 2013.
English summary of Second Expert Report for EC Appl. No. SP-06-6873 dated Mar. 27, 2013.
Invitation Pursuant to Art. 94(3) and Rule 71(1) EPC for EP Application No. 06845745.6 dated Jul. 30, 2013.
Invitation Pursuant to Art. 94(3) and Rule 71(1) EPC for EP Application No. 09156851.9 dated Jul. 30, 2013.
Letter Reporting Further Office Action for Mexican Appl. No. PA/a/2006/010922 dated Jul. 30, 2013.
English translation of Office Action for TW patent application No. 095147808 dated Jul. 16, 2013.
First Office Action for Vietnam Application No. 1-2006-01765 dated Apr. 11, 2013.
Grammatikos, Alexander, "The genetic and environmental basis of atopic diseases", Annals of Medicine, 2008 (40) pp. 482-495.
Medical News Today, "All About Asthma", downloaded from http://www.medicalnewstoday.com/info/asthma/types-of-asthma.php on May 10, 2013 3 pages.
Advisory Action for U.S. Appl. No. 13/347,757 dated Aug. 28, 2013.
Reexamination Notice for CN Application No. 200580009596.0 dated Jul. 9, 2013.
Office Action for U.S. Appl. No. 13/347,978 dated Aug. 22, 2013.
Amendment for U.S. Appl. No. 13/348,035 dated Sep. 5, 2013.
International Search Report and Written Opinion for PCT/US2011/0666258 dated Feb. 10, 2012.
International Preliminary Report on Patentability for PCT/US2011/0066258 dated Jul. 2, 2013.
International Search Report and Written Opinion for PCT/US2013/040608 dated Jun. 19, 2013.
International Search Report and Written Opinion for PCT/US2013/044899 dated Aug. 1, 2013.
Amendment for U.S. Appl. No. 11/641,978 dated Aug. 21, 2013.
Notice of Allowance for U.S. Appl. No. 11/641,978 dated Dec. 16, 2013.
Office action in U.S. Appl. No. 13/347,750 dated Sep. 10, 2013.
Amendment in U.S. Appl. No. 13/347,750 dated Dec. 10, 2013.
Notice of Abandonment for U.S. Appl. No. 13/347,757 dated Dec. 17, 2013.
Notice of Abandonment for U.S. Appl. No. 13/347,985 dated Sep. 12, 2013.
Final Office Action for U.S. Appl. No. 13/348,035 dated Oct. 18, 2013.
Office Action for U.S. Appl. No. 13/347,877 dated Oct. 9, 2013.
Final Office Action for U.S. Appl. No. 13/347,956 dated Sep. 17, 2013.
Response to Office Action for U.S. Appl. No. 13/347,956 dated Nov. 18, 2013.
Notice of Allowance in U.S. Appl. No. 13/347,956 dated Dec. 2, 2013.
Office Action from Canadian Application No. 2,632,262 dated Nov. 29, 2013.
Office action from Canadian Application No. 2,807,787 dated Aug. 22, 2013.
Response to Office Action in U.S. Appl. No. 13/347,877 dated Jan. 9, 2014.

(56) References Cited

OTHER PUBLICATIONS

Rule 161/162 Communication in EP Application No. 11808092.8 dated Aug. 2, 2013.
Translation of Notice of Rejection/Office Action in Japanese Application No. 2012-139422 date Oct. 22, 2013.
Subsequent exam report issued in Philippines Application No. 12006501893 mailed Sep. 4, 2013.
Office Action (Paper No. 8) issued in Philippines Application No. 1-2008-501331 dated Nov. 20, 2013.
Search Report and Written Opinion in Singapore Application No. 201009417-5 dated Sep. 3, 2013.
Hao, Yanlei et al., "Effects of Beta-Hydroxy-Beta-Methylbutyrate on Markers of Muscle Hypertrophy and Apoptotic Signaling During Reloading in Aged Rats Following Disuse," Medicine & Science in Sports & Exercise, vol. 42, No. 5, Suppl. 1, May 2010, p. 2, XP009156085.
Hao, Yanlei et al., "Beta-Hydroxy-Beta-Methylbutyrate Reduces Myonuclear Reduces Myonuclear Apoptosis During Recovery From Hind Limb Suspension-Induced Muscle Fiber Atrophy in Aged Rats," American Journal of Physiology—Regulatory Integrative and Comparitive Physiology, vol. 301, No. 3, Sep. 2011, pp. R701-R715, XP009156087.
Jank et al., "Effect of 3-hydroxy-3-methylbutyrate (HMB) on muscle cathepsins and calpain activities during the post-dexamethasone recovery period in young rats," Polish Journal of Veterninary Sciences, vol. 3, No. 4, pp. 213-218 (2000).
Lynch G.S., "Therapies for Improving Muscle Function in Neuromuscular Disorders," Exercise and Sport Sciences Reviews, Journal Pub Affiliates, vol. 29, No. 4, Oct. 1, 2001, pp. 141-148, XP008063778.
Payne et al., "Nutritional Therapy Improves Function and Complements Corticosteroid Intervention in mdx Mice," Muscle & Nerve, 33, pp. 66-77 (2006).
Pimentel et al., "β-hydroxy-β-methylbutyrate (HMB) supplementation stimulates skeletal muscle hypertrophy in rats via the mTOR pathway," Nutrition and Metabolism, 8:11 (2011).
Rieu, et al., "Glucocorticoid excess induces a prolonged leucine resistance on muscle protein synthesis in old rats," Exp. Gerontol., 39(9), pp. 1315-1321 (2004).
Scheller, Eric S., et al., "The Effects of B-Hydroxy B-Methylbutyrate on Apoptotic Signaling and Recovery Following Disuse in Aged Rat Extensor Digitorum Longus Muscle," Medicine & Science in Sports & Exercise, vol. 42, No. 5, Suppl. 1, May 2010, p. 827, XP009156140.
Shah, et al., "Glucocorticoids oppose translational control by leucine in skeletal muscle," Am. J. Physiol. Endocrinol. Metab., 279: E1185-E1190 (2000).
Soares, JMC et al., "The Effects of Beta-Hydroxy-Beta-Methylbutyrate (HMB) on Muscle Atrophy Induced by Immobilization," Medicine and Science in Sports and Exercise, vol. 33, No. 5 Supl., May 2001, p. S140, XP009156086.
Tisdale, MJ, "The ubiquitin-proteosome pathway as a therapeutic target for muscle wasting," J. Support Oncol., 3(3), pp. 209-217 (2005).
Response with RCE to Office Action in U.S. Appl. No. 13/348,035 dated Jan. 21, 2014.
International Search Report and Written Opinion for PCT/US2013/061014 dated Feb. 6, 2014.
Notice of Allowance including Examiner Initiated Interview Summary in U.S. Appl. No. 11/641,978 dated Mar. 17, 2014.
Final Office Action in U.S. Appl. No. 13/347,750 dated Mar. 18, 2014.
Notice of Allowance in U.S. Appl. No. 13/348,035 dated Mar. 31, 2014.
Notice of Allowance in U.S. Appl. No. 13/347,877 dated Mar. 17, 2014.
Notice of Allowance in U.S. Appl. No. 13/347,956 dated Apr. 4, 2014.
Second Reexamination Notice in Chinese Application No. 200580009596.0 dated Feb. 27, 2014.
Communication in EP Application No. 11187274.3 dated Mar. 13, 2014.
English translation of Office Action in Japanese Application No. 2012-139422 dated Feb. 25, 2014 (received Apr. 21, 2014).
English translation of Office Action in Japanese Application No. 2013-10874 dated Mar. 18, 2014.
Office Action (Paper No. 10) in Philippines Application No. 1-2008-501331 dated Feb. 26, 2014 (received Mar. 16, 2014).
Second Office Action in Vietnam Application No. 1-2006-01765 dated Feb. 27, 2014.
Medicine Net, "Cancer", 2008, downloaded Apr. 7, 2008 from http://www.medterms.com, 2 pages.
Wang et al., "Effect of Curcumin on Airway Collagen Deposition and the Expression of Transformation Growth Factor beta-1 in Rats with Asthma", Journal of Clinical Pediatrics, vol. 23, No. 9, p. 659 (2005) (abstract) [English summary provided] (crossed out by examiner because no date was provided).
Ostaszewski, P. et al., "3-Hydroxy-3 Methylbutyrate (HMB) Fed in the Water Enhance Immune Response in Young Broilers", Poultry Science 77 (Suppl. 1), p. 26, Abstract 96 (1998) (crossed out by examiner because no date was provided).
Amendment after Final Office Action in U.S. Appl. No. 13/347,750 dated May 5, 2014.

\* cited by examiner

90kDa —  A B C D E F G H I J K L

90kDa —  A B C D E F G H I J K L

METHOD OF USING BETA-HYDROXY-BETA-METHYLBUTYRATE FOR TREATING DISEASE-ASSOCIATED WASTING

This application is a divisional of prior U.S. application Ser. No. 11/025,466 filed Dec. 29, 2004, which is a continuation-in-part of prior U.S. application Ser. No. 10/810,762 filed Mar. 26, 2004, the entire disclosures of which are incorporated herein by reference.

The present invention relates to methods for the prevention and treatment of chronic inflammatory diseases, cancer, and involuntary weight loss. In the practice of the present invention patients are enterally administered HMB alone or alternatively in combination with eicosapentaenoic (20:5 ω-3), FOS, carnitine and mixtures thereof. HMB may be added to food products comprising a source of amino-nitrogen enriched with large neutral amino acids such as leucine, isoleucine, valine, tyrosine, threonine and phenylalanine and substantially lacking in free amino acids.

BACKGROUND

Undesired weight loss, particularly lean mass loss is a relatively common occurrence in critical illness, and has a significant impact on morbidity and mortality. This is particularly true in cancer patients, where such mass losses can become treatment-limiting, and thus impact overall prognosis.

Cachexia is a syndrome characterized by anorexia, weight loss, premature satiety, asthenia, loss of lean body mass, and multiple organ dysfunction. It is a common consequence of chronic illnesses (both malignant and non-malignant) and is associated with a poorer prognosis in chronic obstructive pulmonary disease (COPD), chronic heart failure (CHF), renal failure, AIDS, dementia, chronic liver disease and cancer. It is often independent of other indicators of disease severity. (Witte, K. K. A. and Clark, A. L.: Nutritional abnormalities contributing to cachexia in chronic illness, International Journal of Cardiology 85:23-31, 2002)

Pulmonary disease is often associated with cachexia, and substantial numbers of patients suffering from COPD, particularly emphysema, become emaciated during the course of the disease. Weight loss is an independent risk factor for prognosis, and is often associated with increased oxygen consumption. COPD is also associated with a general elevated systemic inflammatory response, reflected by elevated concentrations of pro-inflammatory cytokines and acute phase proteins in the peripheral blood. Such changes are often associated with muscle wasting syndromes.

Studies with incubated muscles and muscle extracts suggest that the ATP-dependent ubiquitin-proteosome pathway is responsible for most of the increased proteolysis which ultimately results in muscle wasting. In particular, increased levels of ubiquitin-conjugated proteins, and increases in mRNA levels for polyubiquitin, certain proteosome subunits and the ubiquitin-conjugating enzyme $E2_{14K}$ are features found in most atrophying muscles.

The majority of patients with cancer whose disease progresses to metastatic disease develop cachexia during their treatment program and the cachexia contributes to their deaths. The frequency of weight loss in cancer patients ranges from 40% for patients with breast cancer, acute myelocytic leukemia, and sarcoma to more than 80% in patients with carcinoma of the pancreas and stomach. About 60% of patients with carcinomas of the lung, colon or prostate have experienced weight loss prior to beginning chemotherapy.

Although the relationship between pretreatment malnutrition (weight loss) and adverse outcome is established, no consistent relationship has been demonstrated between the development of cachexia and tumor size, disease stage, and type or duration of the malignancy.

Cancer cachexia is not simply a local effect of the tumor. Alterations in protein, fat, and carbohydrate metabolism occur commonly. For example, abnormalities in carbohydrate metabolism include increased rates of total glucose turnover, increased hepatic gluconeogenesis, glucose intolerance and elevated glucose levels. Increased lipolysis, increased free fatty acid and glycerol turnover, hyperlipidemia, and reduced lipoprotein lipase activity are frequently noted. The weight loss associated with cancer cachexia is caused not only by a reduction in body fat stores but also by a reduction in total body protein mass, with extensive skeletal muscle wasting. Increased protein turnover and poorly regulated amino acid oxidation may also be important. The presence of host-derived factors produced in response to the cancer have been implicated as causative agents of cachexia, e.g., tumor necrosis factor-α (TNF) or cachectin, interleukin-1 (IL-1), IL-6, gamma-interferon (IFN), and prostaglandins (PGs) (e.g., $PGE_2$).

Weight loss is common in patients with carcinomas of the lung and gastrointestinal tract, resulting in a massive loss of both body fat and muscle protein, while non-muscle protein remains unaffected. While loss of body fat is important in terms of energy reserves, it is loss of skeletal muscle protein that results in immobility, and eventually impairment of respiratory muscle function, leading to death from hypostatic pneumonia. Although cachexia is frequently accompanied by anorexia, nutritional supplementation alone is unable to maintain stable body weight and any weight that is gained is due to an increase in adipose tissue and water rather than lean body mass. The same is true for appetite stimulants, such as megestrol acetate and medroxyprogesterone acetate, suggesting that loss of lean body mass is due to factors other than energy insufficiency.

Skeletal muscle mass is a balance between the rate of protein synthesis and the rate of degradation. Patients with cancer cachexia show a depression of protein synthesis in skeletal muscle and an increase in protein degradation, which is reflected in an increased expression of the ubiquitin-proteasome proteolytic pathway, the major determinant of protein degradation. Thus skeletal muscle from cachectic cancer patients shows increased expression of mRNA for both ubiquitin and proteasome subunits, while proteasome proteolytic activity increased in parallel with ubiquitin expression. The inability of anabolic stimuli to increase lean body mass in cachectic patients suggests that protein degradation must be attenuated before muscle mass can increase. Eicosapentaenoic acid (EPA), downregulates the increased expression of the ubiquitin-proteasome proteolytic pathway in the skeletal muscle of cachectic mice, and has been shown to stabilize body weight in cachectic patients with pancreatic cancer. When patients consumed an energy-dense supplement containing 32 g protein and 2 g EPA body weight increased and this was attributed solely to an increase in lean body mass (Barber, M. D., Ross, J. A., Voss, A. C., Tisdale, M. J., Fearon, K. C. H. *The effect of an oral nutritional supplement enriched with fish oil on weight-loss in patients with pancreatic cancer*. Br. J. Cancer, 81: 80-86, 1999).

A recent study by May et al (May, P. E., Barber, A., D'Olimpio, J. T., Hourihane, A. and Abumrad, N. N. *Reversal of cancer-related wasting using oral supplementation with a combination of β-hydroxy-β-methylbutyrate, arginine and glutamine*. Am. J. Surg., 183: 471-479, 2002) showed a mixture of HMB, arginine and glutamine to be effective in increasing body weight in weight losing patients with advanced (stage IV) cancer. Moreover, the increase in body weight was attributed to an increase in fat-free mass, as observed with EPA.

The use of the polyunsaturated fatty acid eicosapentaenoic acid is suggested for the treatment of cachexia by inhibiting lipolytic activity of lipolytic agents in body fluids and the activity of the enzyme guanidino-benzoatase. See Tisdale, M. J., and Beck, A., U.S. Pat. No. 5,457,130, issued Oct. 10, 1995; and Tisdale, et al. *Cancer Research* 50: 5022-5026 (August 1990). However, the product taught by Tisdale was in a solid dosage form, requiring an already ill patient to swallow 12-16 capsules per day. This method had serious drawbacks, including difficulty in swallowing, belching, and bad odor.

HMB has been found to be useful within the context of a variety of applications. Specifically, in U.S. Pat. No. 6,031,000 to Nissen et al. describes a composition comprising HMB, free L-arginine, and free L-glutamine. This patent also provides a method for the treatment of disease-associated wasting of an animal and other methods comprising administering to the animal a composition comprising HMB and at least one free amino acid.

U.S. Pat. No. 5,348,979 to Nissen et al. describes the use of HMB in the nitrogen retention in human subjects. The amount of HMB administered is effective to conserve protein as determined by reduction in urinary nitrogen. The method can be used with patients having a negative nitrogen balance due to disease conditions, and also with normal elderly persons who are subject to protein loss.

U.S. Pat. No. 5,028,440 to Nissen describes a method for raising meat producing domestic animals to increase lean tissue development. HMB is fed within the range of from 0.5 to 100 mg.

U.S. Pat. No. 4,992,470 to Nissen describes the use of HMB to be markedly more effective for activating the immune function of T lymphocytes of mammals than .alpha.-ketoisocaproate (KIC). For activation of the T lymphocytes, HMB or an edible water-soluble salt thereof is administered to the mammal by a route through which the HMB enters the blood of the mammal. The amount administered is sufficient for effective enhancement of the blastogenesis of their T lymphocytes.

Some bodybuilding advertising claims make the bare assertion that HMB promotes protein synthesis, (see, e.g. websites:

http://www.bodybuilding.com/store/kzn/hmb.html;
    http://www.interactivenutrition.com/products/hmb.php; and
    http://www.interactivenutrition.com/learningzone/hmb.php )

but these lack any scientific documentation and amount to mere "puffery" that appears to misstate the established inhibitory effect of HMB protein degradation, which also leads to gain in muscle mass but is not "synthesis". The only scientific study making this suggestion is a 1996 abstract by Ostaszewski, et al (J. Anim. Sci 1996; 74(Supppl. 1)) which claims their data in rats and chicks indicates that "HMB stimulates [protein synthesis] slightly (avg. 6%) and markedly decreased [protein breakdown] (avg. −18%)". A later paper by 4 of the same authors using the same model in rats and chicks failed to repeat the synthesis effect and concludes that "HMB had no significant effect on protein synthesis" (Ostaszewski, et al (J. Anim. Physiol. a. Anim. Nutr. 84 (2000), 1-8). This leaves doubt and uncertainty about whether HMB stimulates protein synthesis or not, but in any event, each of these authors reports on normal subjects; not one addresses the effect of HMB in individuals whose muscle status is compromised by a disease-associated wasting condition. In such conditions, protein synthesis is significantly depressed.

German patent DE 29707308 to Kunz describes the use of branched chain amino acids in combination with HMB to promote muscle generation in the weight training population. Kunz teaches that a supplement of 3 gm taken daily with a protein consumption of 200 gm per day enhances the value of nutritional protein and significantly increases the protein efficiency. Kunz also teaches that better effects can be achieved when HMB is combined with protein hydrolysates and/or free amino acid mixtures rather than with intact (pure) proteins.

U.S. Pat. No. 5,976,550 to Engel et al. describes a dietary food supplement for weight reduction formed of a mixture of a sugar based confectionery containing therapeutic amounts of chitosan, kava and a fat burning nutriceutical which may include choline/inusital, chromium picolinate, HMB, carnitine and pyruvate. The nutriceutical ingredient mixed with the chitosan and kava functions to burn whatever fat the body has consumed, i.e. to metabolize better any fat that is ingested and not attracted to the chitosan.

Commercial products designed for the weight lifting population that contain HMB include Lean DynamX by EAS Inc. of Golden, Colo. Lean DynamX provides a blend of ingredients that support fat loss without the use of strong stimulants. The ingredients include HMB, chromium picolinate, conjugated linoleic acid, mate leaves and stems and carnitine tartrate. The powder composition is mixed with water and taken 2-3 servings daily, with one serving taken 30 minutes before workouts.

Additional commercial products include Mega HMB Fuel® from Twinlab Corporation in Hauppauge, N.Y. Mega HMB Fuel® contains 750 mg of HMB in one capsule. The suggested daily dosage is 4 capsules to support damage to muscle cells which can occur subsequent to intense resistance exercise.

Also of interest is U.S. Pat. No. 5,444,054 to Garleb, et al. and related U.S. Pat. Nos. 5,780,451 and 6,468,987. These documents describe compositions and methods useful in the treatment of ulcerative colitis. Such compositions include a protein source that can be intact or hydrolyzed proteins of high biological value (col. 21); an indigestible oligosaccharide such as fructooligosaccharide; and a lipid blend containing a relatively high proportion of eicosapentaenoic acid, which contributes to a relatively high ω-3 to ω-6 fatty acid ratio.

Long chain fatty acid bio-pathways and physiological actions are discussed in U.S. Pat. No. 5,223,285 to DeMichele, et al., the entirety of which is incorporated herein by reference.

The prevention and/or treatment of cachexia remain a frustrating problem. Both animal and human studies suggest that nutritional support is largely ineffective in repleting lean body mass in the cancer-bearing host. Randomized trials exploring the usefulness of total parenteral nutrition (TPN) support as an adjunct to cytotoxic antineoplastic therapy have demonstrated little improvement in treatment results. See for example Brennan, M. F., and Burt, M. E., 1981, *Cancer Treatment Reports* 65 (Suppl. 5): 67-68. This, along with a clear demonstration that TPN can stimulate tumor growth in animals suggests the routine use of TPN in cancer treatment is not justified. Kisner, D. L., 1981, *Cancer Treatment Reports* 65 (Suppl. 5): 1-2.

SUMMARY OF THE INVENTION

In a first embodiment, the present invention relates to methods for the prevention and treatment of chronic inflammatory diseases, cancer, and/or involuntary weight loss. In the practice of the present invention patients are enterally administered HMB alone or alternatively in combination with one or more of eicosapentaenoic acid (EPA) (20:5 ω-3), FOS, large neutral amino acids (LNAA), carnitine and mixtures thereof.

In another embodiment, the present invention provides a method for the treatment of the disease-associated wasting of a patient. The method comprises administering to the patient the above-described composition, which comprises HMB in amounts sufficient to treat the disease-associated wasting, wherein, upon administration of the composition to the patient, the disease-associated wasting is treated. This effect is produced in part by the known inhibition of protein breakdown, and in part by the surprising finding that protein synthesis is significantly stimulated by HMB in wasting patients.

In another embodiment, the present invention provides a method for reducing tumor growth rate in a patient. The method comprises administering to the patient the above-described composition, which comprises HMB in amounts sufficient to reduce tumor growth rate, wherein, upon administration of the composition to the patient, the tumor growth rate is reduced.

In another embodiment, the present invention provides a method for the prevention or treatment of diseases in patients by down regulating the expression and/or activity of protein kinase C, nuclear factor kappa-B, ubiquitin-conjugating enzymes, and components of 26S proteasome. These methods comprise administering to the patient HMB, its salts, metabolites or derivatives thereof.

In yet another embodiment, the present invention relates to compositions, for example nutritional compositions, containing HMB alone or alternatively in combination with one or more of eicosapentaenoic acid (20:5 ω-3), FOS, large neutral amino acids (LNAA), carnitine and mixtures thereof. HMB may be added to food products comprising a source of amino-nitrogen enriched with large neutral amino acids such as leucine, isoleucine, valine, tyrosine, threonine and phenylalanine and substantially lacking in free amino acids.

DETAILED DESCRIPTION OF THE INVENTION

Definitions

Figure 1:
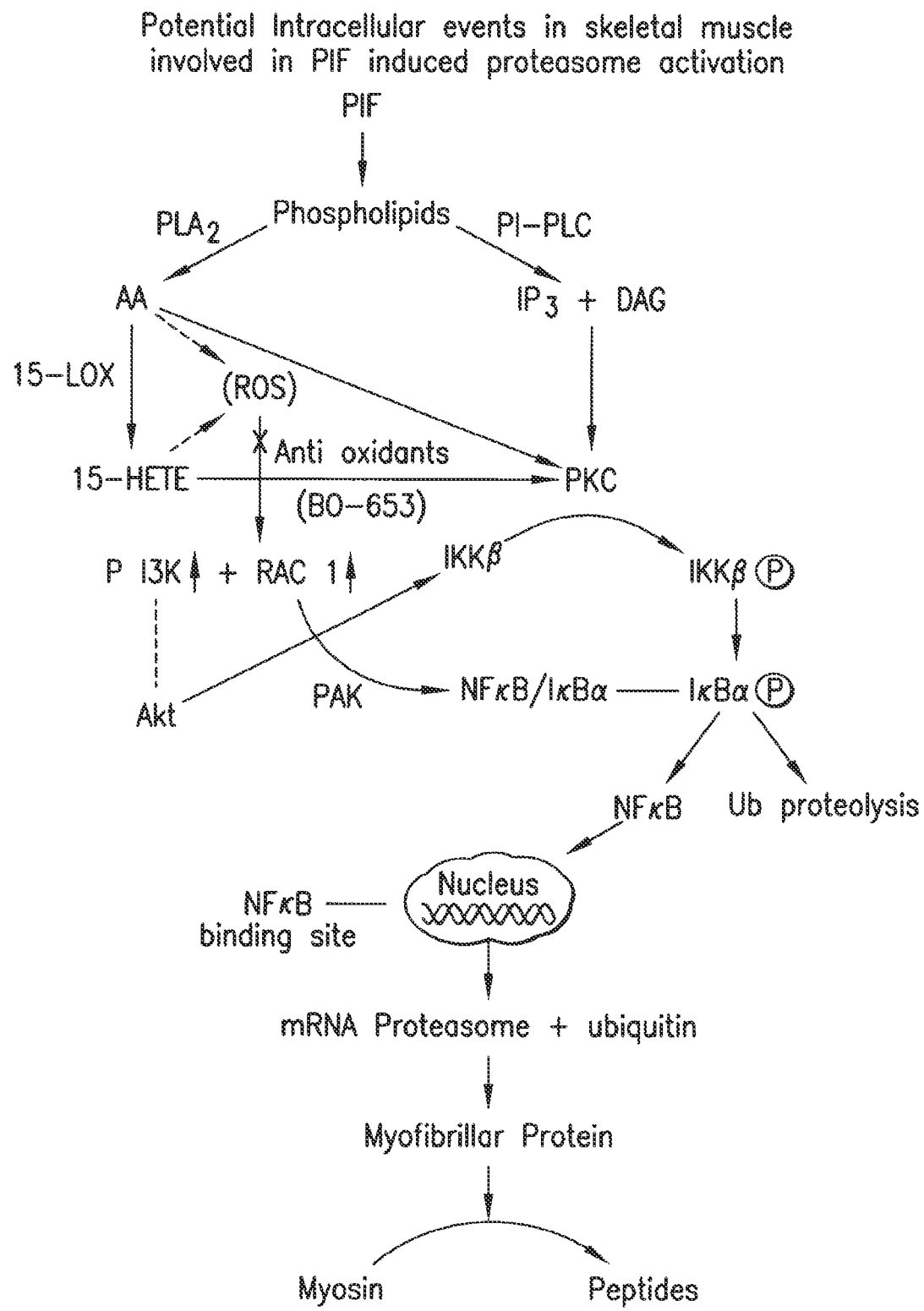
FIG. 1 presents a scheme describing the potential intracellular events in skeletal muscle involved in PIF induced proteasome activation.

The term HMB, which is also referred to as beta-hydroxy-beta-methylbutyric acid, or beta-hydroxy-isovaleric acid, can be represented in its free acid form as $(CH_3)_2(OH)CCH_2COOH$. HMB is a metabolite of leucine formed by transamination to alpha-ketoisocaproate (KIC) in muscle followed by oxidation of the KIC in the cytosol of the liver to give HMB. While any suitable form of HMB can be used within the context of the present invention, preferably, HMB is selected from the group consisting of a free acid, a salt, an ester, and a lactone; more preferably, HMB is in the form of a non-toxic, edible salt. Preferably, the HMB salt is water-soluble or becomes water-soluble in the stomach or intestines of a patient. More preferably, the HMB salt is selected from the group consisting of a sodium salt, a potassium salt, a magnesium salt, a chromium salt, and a calcium salt. However, other non-toxic salts, such as other alkali metal or alkaline earth metal salts, can be used.

Similarly, any pharmaceutically acceptable ester can be used in the context of the present invention. Desirably, the HMB ester is rapidly converted to HMB in its free acid form. Preferably, the HMB ester is a methyl ester or ethyl ester. HMB methyl ester and HMB ethyl ester are rapidly converted to the free acid form of HMB. Likewise, any pharmaceutically acceptable lactone can be used in the context of the present invention. Desirably, the HMB lactone is rapidly converted to HMB in its free acid form. Preferably, the HMB lactone is an isovalaryl lactone or a similar lactone. Such lactones are rapidly converted to the free acid form of HMB.

Methods for producing HMB and its derivatives are well known in the art. For example, HMB can be synthesized by oxidation of diacetone alcohol. One suitable procedure is described by Coffman et al., J. Am. Chem. Soc. 80: 2882-2887 (1958). As described therein, HMB is synthesized by an alkaline sodium hypochlorite oxidation of diacetone alcohol. The product is recovered in free acid form, which can be converted to the desired salt. For example, 3-hydroxy-3-methylbutyric acid (HMBA) can be synthesized from diacetone alcohol (4-hydroxy-4-methylpentan-2-one) via oxidation using cold, aqueous hypochlorite (bleach). After acidifying the reaction mixture using HCl, the HMBA product is recovered by extraction using ethyl acetate, and separating and retaining the organic layer from the extraction mixture. The ethyl acetate is removed by evaporation and the residue dissolved in ethanol. After addition of Ca(OH)2 and cooling, crystalline CaHMB can be recovered by filtration, the crystals washed with ethanol and then dried. Alternatively, the calcium salt of HMB is commercially available from Technical Sourcing International (TSI) of Salt Lake City, Utah.

The term "eicosapentaenoic acid" or "EPA" refers to the long chain, polyunsaturated fatty acid designated in the art as (20:5 ω-3), described further herein.

The term "large neutral amino acids" refers to leucine, isoleucine, valine, tyrosine, threonine and phenylalanine. Amino acids are the building blocks of proteins. They are characterized by the presence of a carboxyl group (COOH) and an amino group (NH2) attached to the same carbon at the end of the compound.

The term "substantially lacking in free amino acids" refers to compositions which contain less than 0.4 grams of total free amino acid content in a daily dose of the composition. For example, if the product is designed to be fed at the rate of 1 can per day, then the one can of product contains less than a total of 0.4 grams of free amino acids. The amino acids in question are those naturally occurring L-isomers, consisting of one or more of the following compounds: L-alanine, L-arginine, L-asparagine, L-aspartic acid, L-cysteine (or L-cystine), L-glutamic acid, L-glutamine, glycine, L-histidine, L-Isoleucine, L-leucine, L-lysine, L-methionine, L-phenylalanine, L-proline, L-serine, L-threonine, L-tryptophan, L-tyrosine and L-valine, or their food- or pharmaceutically-acceptable salts, esters, salts or derivatives (such as methyl or ethyl esters).

The term "cachexia" refers to a state of general ill health and malnutrition. It is often associated with and induced by malignant cancer, and is characterized by loss of appetite, loss of body mass, especially lean body mass, and muscle wasting.

The term "fatty acids" refer to a family of carboxylic acids having a hydrocarbon chain, generally from about 12 to 24 carbons long. When unsaturated (having a double bond) at least one point in the hydrocarbon chain, such fatty acids are designated by the position of the first double bond. ω-3 fatty acids have a first double bond at the third carbon from the methyl end of the chain; and include, but are not limited to, α-linolenic acid, stearidonic acid, eicosapentaenoic acid ("EPA"), docosapentaenoic acid and docosahexaenoic acid ("DHA") and the like. ω-6 fatty acids have a first double bond at the sixth carbon from the methyl end of the chain; and include, but are not limited to, linoleic acid, γ-linolenic acid, arachidonic acid ("AA"), and the like.

The term "food products" as used herein refer to delivery vehicles that contain one or more of fats, amino nitrogen and carbohydrates and provides some or all of the nutritional support for a patient in the recommended daily amounts. Frequently a food product will contain vitamins, minerals, trace minerals and the like to provide balanced nutrition to meal replacements, medical foods, supplements. The food products may be in any typical form such as beverages, powders, bars, juices, carbonated beverages, bottled water.

The term "Reference Daily Intakes or RDI" refers to a set of dietary references based on the Recommended Dietary Allowances for essential vitamins and minerals. The Recommended Dietary Allowances are a set of estimated nutrient allowances established by the National Academy of Sciences, which are updated periodically to reflect current scientific knowledge.

The term "patient" refers to humans, dogs, cats, and any other non-ruminant animal.

Any reference to a numerical range in this application should be considered as being modified by the adjective "about". Further, any numerical range should be considered to provide support for a claim directed to a subset of that range. For example, a disclosure of a range of from 1 to 10 should be considered to provide support in the specification and claims to any subset in that range (i.e., ranges of 2-9, 3-6, 4-5, 2.2-3.6, 2.1-9.9, etc.).

Administration:

Nutritional support in the cancer patient can be categorized as (i) supportive, in which nutrition support is instituted to prevent nutrition deterioration in the adequately nourished patient or to rehabilitate the depleted patient before definitive therapy; (ii) adjunctive, in which nutrition support plays an integral role in the therapeutic plan; and (iii) definitive, in which aggressive nutrition support is required for the patient's existence. The routes for providing nutrition support include an oral diet, tube feeding and peripheral or total parenteral nutrition. The preferred embodiment for nutritional methods and compositions of the invention is by the oral route.

An alternate to oral feeding is tube feeding by means of nasogastric, nasoduodenal, esophagostomy, gastrostomy, or jejunostomy tubes.

The beneficial effects that HMB has on the lean body mass of a patient can be achieved in a number of ways. If desired, the HMB may be administered alone, without a carrier. The HMB may simply be dissolved in water and consumed by the patient. Alternatively, the HMB may be sprinkled on food, dissolved in coffee, etc. The total daily dose for the patient will vary widely, but typically a patient will benefit from consuming at least 2 gm/day of HMB. Alternatively, from 20 to 40 mg/kg/day.

In a further embodiment, the HMB may be incorporated into pills, capsules, rapidly dissolved tablets, lozenges, etc. The active dose can vary widely, but will typically range from 250 mg to 1 gm/dose with the patient consuming from 2 to 8 doses/day to achieve the target of 2 gm/day minimum. Methods for preparing such dosage forms are well known in the art. The reader's attention is directed to the most recent edition of Remingtons Pharmaceutical Sciences for guidance on how to prepare such dosage forms.

Nutritional Matrices:

While the HMB may be administered as a single entity, it will typically be incorporated into food products and consumed by the patient during their meals or snack. If desired, the patient may simply modify the recipe of foods they normally consume by sprinkling on food, dissolving in coffee, etc.

In a further embodiment, the HMB will be incorporated into beverages, bars, cookies, etc. that have been specifically designed to enhance the palatability of the HMB and increase the selection of alternative forms, thereby enhancing patient/consumer acceptance.

Typically, the HMB will be incorporated into meal replacement beverages such as Ensure®, Boost®, Glucerna®, Pediasure®, Pedialyte®, etc. The HMB may also be incorporated into meal replacement bars such as PowerBars®, Glucerna® bars, Choice DM® bars, Ensure® bars, and Boost® bars, etc. Alternatively, the HMB maybe incorporated into juices, carbonated beverages, bottled water, etc. Additionally, the HMB may be incorporated into medical nutritonals such as ProSure®, Promote®, Jevity® and Advera® designed to support specific disease states such as cancer, HIV/AIDS, COPD arthritis, etc. Methods for producing any of such food products are well known to those skilled in the art. The following discussion is intended to illustrate such food products and their preparation.

Most meal replacement products (i.e., bars or liquids) provide calories from fat, carbohydrates, and protein. These products also typically contain vitamins and minerals, because they are intended to be suitable for use as the sole source of nutrition. While these meal replacement products may serve as the sole source of nutrition, they typically don't. Individuals consume these products to replace one or two meals a day, or to provide a healthy snack. The nutritional products of this invention should be construed to include any of these embodiments.

The amount of these nutritional ingredients can vary widely depending upon the targeted patient population (i.e., cancer, HIV/AIDS, arthritis, organoleptic considerations, cultural preferences, use, etc.). As a general nonlimiting guideline however, the meal replacement products of this invention will contain the following relative amounts of protein, fat, and carbohydrate (based upon the relative percentage of total calories): a protein component, providing from 5 to 80% of the total caloric content, a carbohydrate component providing from 10 to 70% of the total caloric content, and a lipid component providing from 5 to 50% of the total caloric content.

The meal replacements will contain suitable carbohydrates, lipids and proteins as is known to those skilled in the art of making nutritional formulas. Suitable carbohydrates include, but are not limited to, hydrolyzed, intact, naturally and/or chemically modified starches sourced from corn, tapioca, rice or potato in waxy or non waxy forms; and sugars such as glucose, fructose, lactose, sucrose, maltose, high fructose corn syrup, corn syrup solids, fructooligosaccharides, and mixtures thereof.

Suitable lipids include, but are not limited to, coconut oil, soy oil, corn oil, olive oil, safflower oil, high oleic safflower oil, MCT oil (medium chain triglycerides), sunflower oil, high oleic sunflower oil, palm oil, palm olein, canola oil, cottonseed oil, fish oil, palm kernel oil, menhaden oil, soybean oil, lecithin, lipid sources of arachidonic acid and docosahexaenoic acid, and mixtures thereof. Lipid sources of arachidonic acid and docosahexaenoic acid include, but are not limited to, marine oil, egg yolk oil, and fungal or algal oil.

Numerous commercial sources for these fats are readily available and known to one practicing the art. For example, soy and canola oils are available from Archer Daniels Midland of Decatur, Ill. Corn, coconut, palm and palm kernel oils are available from Premier Edible Oils Corporation of Portland, Organ. Fractionated coconut oil is available from Henkel Corporation of LaGrange, Ill. High oleic safflower and high oleic sunflower oils are available from SVO Specialty Products of Eastlake, Ohio. Marine oil is available from Mochida International of Tokyo, Japan. Olive oil is available from Anglia Oils of North Humberside, United Kingdom. Sunflower and cottonseed oils are available from Cargil of Minneapolis, Minn. Safflower oil is available from California Oils Corporation of Richmond, Calif.

In addition to these food grade oils, structured lipids may be incorporated into the food product if desired. Structured lipids are known in the art. A concise description of structured lipids can be found in INFORM, Vol. 8, No. 10, page 1004; entitled Structured lipids allow fat tailoring (October 1997). Also see U.S. Pat. No. 4,871,768. Structured lipids are predominantly triacylglycerols containing mixtures of medium and long chain fatty acids on the same glycerol nucleus. Structured lipids and their use in enteral formula are also described in U.S. Pat. Nos. 6,194,379 and 6,160,007.

Optionally, ω-3 fatty acids may comprise up to approximately 30% of the oil blend, preferably the ω-3 fatty acids largely consist of the longer chain forms, eicosapentaenoic acid (EPA) and docosahexaenoic acid (DHA). Dietary oils used in the preparation of the nutritional composition generally contain ω-3 fatty acids in the triglyceride form and include, but are not limited to canola, medium chain triglycerides, fish, soybean, soy lecithin, corn, safflower, sunflower, high-oleic sunflower, high-oleic safflower, olive, borage, black currant, evening primrose and flaxseed oil. Optionally, the weight ratio of ω-6 fatty acids to ω-3 fatty acids in the lipid blend according to the invention is about 0.1 to 3.0. The daily delivery of ω-3 fatty acids should be at least 450 mg and may vary depending on body weight, sex, age and medical condition of the individual. As mentioned, higher levels are desired for adult human consumption: for example, from about 0.5 to 50 gm daily, more preferably from about 2.5 to 5 gm daily.

An unexpected advantage to combining ω-3 fatty acids and HMB is the improvement in taste of the meal replacement. The typical sources of ω-3 fatty acids are fish and algae oils. Each source brings objectionable flavors to the meal replacement product. The Inventors discovered that by adding HMB, the same or better clinical results related to the prevention of involuntary weight loss can be obtained even when using suboptimal or lower levels of ω-3 fatty acids in the product. Consequently, the Inventor's have discovered that there is an inverse relationship between the levels of ω-3 fatty acids and HMB. For example, if an effective does of ω-3 fatty acids is 3 gm delivered in 2 cans of a meal replacement, the same clinical results would be seen in product formulated to contain 2 gm of ω-3 fatty acids and 1 gm of HMB delivered in 2 cans or in product formulated to contain 1 gm of ω-3 fatty acids and 2 gm of HMB delivered in 2 cans. The product formulated to contain only 1 gm of ω-3 fatty acids will taste much better than the product formulated with 2 or 3 gm of ω-3 fatty acids while achieving the same clinical effectiveness. Further, since ω-3 fatty acids are known inhibitors of AA, a mediator of inflammation, a product containing ω-3 fatty acids and HMB could have broader benefits than those containing either of the ingredients alone.

Suitable protein sources include, but not limited to, milk, whey and whey fractions, soy, rice, meat (e.g., beef), animal and vegetable (e.g., pea, potato), egg (egg albumin), gelatin and fish. Suitable intact protein sources include, but are not limited to, soy based, milk based, casein protein, whey protein, rice protein, beef collagen, pea protein, potato protein, and mixtures thereof.

Optionally, the intact protein source is enriched in large neutral amino acids (LNAA) comprising valine, isoleucine, leucine, threonine, tyrosine and phenylalanine. Typically, about 40% of casein, whey and soy protein sources are large neutral amino acids. For example, caseinate contains about 38 wt/wt % LNAA, whey protein concentrate contains about 39 wt/wt % LNAA and soy protein isolate contains about 34 wt/wt % LNAA. Typically, the meal replacement is formulated with a protein source that will deliver about 1 to 25 gm of LNAA per day, preferably from about 1 to 20 gm of LNAA per day, more preferably from about 4 to 20 gm of LNAA per day. As an example, a meal replacement consumed 3 times a day that contains a protein comprising 4.8 gm LNAA will deliver 14.4 gm LNAA per day.

The meal replacements preferably also contain vitamins and minerals in an amount designed to supply or supplement the daily nutritional requirements of the person receiving the formula. Those skilled in the art recognize that nutritional formulas often include overages of certain vitamins and minerals to ensure that they meet targeted level over the shelf life of the product. These same individuals also recognize that certain micro ingredients may have potential benefits for people depending upon any underlying illness or disease that the patient is afflicted with. For example, cancer patients benefit from such antioxidants as beta-carotene, vitamin E, vitamin C and selenium. The food products preferably include, but are not limited to, the following vitamins and minerals: calcium, phosphorus, sodium, chloride, magnesium, manganese, iron, copper, zinc, selenium, iodine, chromium, molybdenum, conditionally essential nutrients m-inositol, carnitine and taurine, and Vitamins A, C, D, E, K and the B complex, and mixtures thereof.

The conditionally essential nutrient carnitine is a naturally occurring amino acid formed from methionine and lysine. Its major metabolic role is associated with the transport of long-chain fatty acids across the mitochondrial membranes, thus stimulating the oxidation of these fuel substances for metabolic energy. Carnitine supplementation is an important metabolic tool in conditions such as diseases of the liver and kidney, and major chronic illnesses or extensive injuries complicated by malnutrition. Optionally, the meal replacements may be supplemented with carnitine at levels sufficient to supply up to 4 gm/day of carnitine.

The meal replacements also may contain fiber and stabilizers. Suitable sources of fiber/and or stabilizers include, but are not limited to, xanthan gum, guar gum, gum arabic, gum ghatti, gum karaya, gum tracacanth, agar, furcellaran, gellan gum, locust bean gum, pectin, low and high methoxy pectin, oat and barley glucans, carrageenans, psyllium, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, FOS (fructooligosaccharides), and mixtures thereof. Numerous commercial sources of soluble dietary fibers are available. For example, gum arabic, hydrolyzed carboxymethylcellulose, guar gum, pectin and the low and high methoxy pectins are available from TIC Gums, Inc. of Belcamp, Md. The oat and barley glucans are available from Mountain Lake Specialty Ingredients, Inc. of Omaha, Nebr. Psyllium is available from the Meer Corporation of North Bergen, N.J. while the carrageenan is available from FMC Corporation of Philadelphia, Pa.

The fiber incorporated may also be an insoluble dietary fiber representative examples of which include oat hull fiber, pea hull fiber, soy hull fiber, soy cotyledon fiber, sugar beet fiber, cellulose and corn bran. Numerous sources for the insoluble dietary fibers are also available. For example, the corn bran is available from Quaker Oats of Chicago, Ill.; oat hull fiber from Canadian Harvest of Cambridge, Minn.; pea hull fiber from Woodstone Foods of Winnipeg, Canada; soy hull fiber and oat hull fiber from The Fibrad Group of LaVale, Md.; soy cotyledon fiber from Protein Technologies International of St. Louis, Mo.; sugar beet fiber from Delta Fiber Foods of Minneapolis, Minn. and cellulose from the James River Corp. of Saddle Brook, N.J.

A more detailed discussion of examples of fibers and their incorporation into food products may be found in U.S. Pat. No. 5,085,883 issued to Garleb et al.

The quantity of fiber utilized in the formulas can vary. The particular type of fiber that is utilized is not critical. Any fiber suitable for human consumption and that is stable in the matrix of a food product may be utilized.

In addition to fiber, the meal replacements may also contain oligosaccharides such as fructooligosaccharides (FOS) or glucooligosaccharides (GOS). Oligosaccharides are rapidly and extensively fermented to short chain fatty acids by anaerobic microorganisms that inhabit the large bowel. These oligosaccharides are preferential energy sources for most *Bifidobacterium* species, but are not utilized by potentially pathogenic organisms such as *Clostridium perfingens, C. difficile*, or *Eschericia coli*.

Typically, the FOS comprises from 0 to 5 gm/serving of the meal replacement, preferably from 1 to 5 gm/serving, more preferably from 2 to 4 gm/serving of the meal replacement.

The meal replacements may also contain a flavor to enhance its palatability. Artificial sweeteners may be added to complement the flavor and mask salty taste. Useful artificial sweeteners include saccharin, nutrasweet, sucralose, acesulfame-K (ace-K), etc.

Meal replacements can be manufactured using techniques well known to those skilled in the art. Various processing techniques exist. Typically these techniques include formation of a slurry from one or more solutions, which may contain water and one or more of the following: carbohydrates, proteins, lipids, stabilizers, vitamins and minerals. The HMB is typically added to the carbohydrate slurry prior to the other minerals. The slurry is emulsified, homogenized and cooled. Various other solutions may be added to the slurry before processing, after processing or at both times. The processed formula is then sterilized and may be diluted to be dried to a powder, utilized on a ready-to-feed basis or packaged in a concentrated liquid form. When the resulting formula is meant to be a ready-to-feed liquid or concentrated liquid, an appropriate amount of water would be added before sterilization.

Solid compositions such as bars, cookies, etc. may also be manufactured utilizing techniques known to those skilled in the art. For example, they may be manufactured using cold extrusion technology as is known in the art. To prepare such compositions, typically all of the powdered components will be dry blended together. Such constituents typically include the proteins, vitamin premixes, certain carbohydrates, etc. The fat-soluble components are then blended together and mixed with the powdered premix above. Finally any liquid components are then mixed into the composition, forming a plastic like composition or dough.

The process above is intended to give a plastic mass that can then be shaped, without further physical or chemical changes occurring, by the procedure known as cold forming or extrusion. In this process, the plastic mass is forced at relatively low pressure through a die, which confers the desired shape. The resultant exudate is then cut off at an appropriate position to give products of the desired weight. If desired the solid product is then coated, to enhance palatability, and packaged for distribution. Typically the package will provide directions for use by the end consumer (i.e., to be consumed by a cancer patient, to help prevent lean muscle loss, etc.)

The solid compositions of the instant invention may also be manufactured through a baked application or heated extrusion to produce cereals, cookies, and crackers. One knowledgeable in the arts would be able to select one of the many manufacturing processes available to produce the desired final product.

As noted above, the HMB may also be incorporated into juices, non-carbonated beverages, carbonated beverages, electrolyte solutions, flavored waters (hereinafter collectively "beverage"), etc. The HMB will typically comprise from 0.5 to 2 gm/serving of the beverages. Methods for producing such beverages are well known in the art. The reader's attention is directed to U.S. Pat. Nos. 6,176,980 and 5,792,502, the contents of each which are hereby incorporated by reference. For example, all of the ingredients, including the HMB are dissolved in an appropriate volume of water. Flavors, colors, vitamins, etc. are then optionally added. The mixture is then pasteurized, packaged and stored until shipment.

Methods of Using the Invention

It has now been surprisingly and unexpectedly discovered that HMB alone can reduce tumor growth rate and in combination with sub-optimal dose levels of EPA enhance the anticachectic effect. The combination of EPA and HMB preserve muscle mass by attenuating protein degradation through down regulation of the increased expression of key regulatory components of the ubiquitin-proteasome proteolytic pathway. While not intending the invention to be limited to any particular theory of operation, applicants describe below a probable mechanism.

In times of extreme need (e.g., starvation and the like), skeletal muscle is often used by the body as a reservoir of amino acids and energy. This is mediated by upregulation of the proteolysis and downregulation of protein synthesis in muscle. The net result of which is release of amino acids from muscle to the general circulation for use in maintenance of critical systems. When good health and adequate nutrient availability are restored, muscle is rebuilt. In the case of cachexia, this system is inappropriately activated, so even in the case of nutritional adequacy, muscle tissue proteins continue to be broken down.

One of the key proteolytic systems which are inappropriately activated is the ubiquitin proteosome system. When normally functioning, this system recognizes proteins which are either aged or in some other manner either damaged or no longer needed, and marks them for removal via conjugation with ubiquitin. Such ubiquitinylated proteins are recognized by the proteosome, and degraded, releasing free ubiquitin and peptides and free amino acids in an energy-consuming process. There are a number of signaling molecules which activate or upregulate this system, including proteolysis-inducing factor (PIF), which is a protein factor produced by certain cachexia-inducing tumors. Binding of PIF to the muscle cell causes the upregulation of phospholipase A (PLA). This in turn produces signaling factors which ultimately activate protein kinase C, resulting in the activation of genes (via nuclear factor kappa B, NFκB) for ubiquitin conjugation and for certain subunits of the proteosome. The net result of all of this signaling is the up regulation of the ubiquitin proteosome system, and inappropriate, sustained protein degradation in the muscle. FIG. 1 shows a detailed pathway of this activation sequence.

Protein Kinase C

Protein kinase C is a family of calcium- and lipid-activated serine-threonine kinases that play a key role in numerous intracellular signaling cascades. There are at least 12 different PKC isotypes, which are grouped into three classes based on their primary structure and biochemical properties (CA Carter: "Protein kinase C as a drug target: Implications for drug or diet prevention and treatment of cancer." Current Drug Targets 1:163-183 (2000). These are the conventional— (cPKCα, βI, βII and γ) which require diacylglycerol, phosphatidylserine and calcium for activation, novel (nPKCδ, ε, η, θ and μ) which require diacylglycerol and phosphatidylserine, but are calcium independent, and the atypical (aPKC λ, τ and ζ) which are calcium and diacylglycerol-independent.

PKC is synthesized as a membrane-bound proenzyme. Removal of the pro-sequence by proteolytic cleavage, and subsequent phosphorylation releases a competent enzyme from the membrane to the cytosol. Subsequent interaction with the peculiar sets of activators produces active enzyme. Thus, there are several levels of regulation possible, including control of expression, control of proteolytic processing, control of initial phosphorylation events and finally, regulation of the cytosolic levels of the various activators required for full activity.

Protein kinase C is involved in some of the signaling pathways leading to mitogenesis and proliferation of cells, apoptosis, platelet activation, remodelling of the actin cytoskeleton, modulation of ion channels and secretion. In addition, other observation that PKC is also the major receptor for tumor-promoting phorboly esters provided a key reagent for studying the mechanism of action of this enzyme. PKC regulates pathways relevant to inflammation, cardiovascular, peripheral microvascular, CNS, oncology, immune and infectious disease states, and are considered as serious and important targets for drug development.

NFκB

Nuclear Factor κB (NFκB) is a family of transcription factors found in a wide variety of mammalian cells. The mature molecule is a homo- or heterodimer, made from one or two of the following 5 gene products (RelA (p65), p50, RelB, c-Rel and p52)—the most common is a dimer of RelA and p50. Under non-activated conditions, NFκB is localized in the cytosol by association with an inhibitory protein IκBα. Upstream signaling involves an IκB kinase, and phosphorylation of the bound IκBα results in it's release from NFκB, allowing the later to translocate to the nucleus, and activate specific gene transcription. The phosphorylated IκBα is degraded by the ubiquitin-proteosome pathway.

NFκB is widely recognized as a key regulatory molecule associated with inflammation. Thus, it plays a key role in both acute and chronic inflammatory diseases (AB Lentsch and PA Ward: "Activation and regulation of NFκB during acute inflammation." Clin Chem Lab Med 37(3):205-208 (1999)). It also plays a role in certain aspects of other diseases, such as cancer metastasis (V B Andela, A H Gordon, G Zotalis, R N Rosier, J J Goater, G D Lewis, E M Schwarz, J E Puzas and R J O'Keefe: "NFκB: A pivotal transcription factor in prostate cancer metastasis to bone." Clinical Orthopaedics and Related Research 415S:S75-S85 (2003)). This transcription factor is involved in the development of the diabetic syndrome (E. Ho and T M Bray: "Antioxidants, NFκB activation and diabetogenesis." Proceedings of the Society for Experimental Biology and Medicine 222:205-213 (1999)) and in immune development and regulation (J Moscat, M T Diaz-Meco and P Rennet "NFκB activation by protein kinase C isoforms and B-cell function." EMBO Reports 4:31-36 (2003)). Finally, NFκB is associated with control of apoptosis and in growth and differentiation. Indeed, PIF (proteolysis inducing factor, which is released by tumors and is involved in cancer-induced lean mass losses) is thought to be a regulator of embryonic development, and triggers a signaling cascade ultimately through NFκB (F. Delfino and W H Walker: "Hormonal regulation of the NFκB signaling pathway." Molecular and Cellular Endocrinology 157:1-9 (1999); T M Watchorn, I Waddell, N Dowidar and J A Ross: "Proteolysis-inducing factor regulates hepatic gene expression via the transcription factor NFκB and STST3." FASEB J 15:562-564 (2001)).

It is also well known that EPA exerts it's beneficial effects on cachexia via inhibition of the signaling resulting from activation of PLA, in particular the release of arachidonic acid (AA). This prevents the subsequent upregulation and activation of the ubiquitin-proteosome pathway by removing the initial signaling event. HMB, while not preventing the activation of PLA or the release of AA, does prevent the upregulation of protein kinase C, preventing all subsequent activation in the signaling pathway, also ultimately preventing the activation of the ubiquitin-proteosome system.

Any disease with which wasting or inflammation is associated such as cardiovascular, peripheral microvascular, central nervous system, oncology, immune and infectious disease states can be treated in accordance with the present methods. Preferably, the disease is selected from the group consisting of cancer, cachexia, age-associated wasting, wasting associated with long-term hospital stay, HIV/AIDS, arthritis, trauma, liver disease, Crohn's disease or other inflammatory bowel diseases (IBD), renal insufficiency and COPD (chronic obstructive pulmonary disease). More preferably, the disease is cachexia.

The present invention provides, in another embodiment, a method for the treatment of the disease-associated wasting of a patient, such as a mammal, preferably a human. The method comprises administering to the patient the above-described composition, which comprises HMB in amounts sufficient to treat the disease-associated wasting, wherein, upon administration of the composition to the patient, the disease-associated wasting is treated.

The amount of HMB that is sufficient to treat disease-associated wasting in a given patient can be determined in accordance with methods well known in the art. When treating the disease-associated wasting of a patient, desirably, the composition comprising HMB is administered to a patient suffering from disease-associated wasting in such an amount, in such a manner, and over such a period of time that the patient's lean tissue mass will increase without a concomitant decrease in the patient's fat mass. An example, within the context of treating the cancer cachexia associated wasting of a human, when the composition is orally administered about twice a day for a minimum of two weeks; the dose is sufficient to provide at least about 2 gm HMB/day; for example between 1 and 10 grams per day for a typical 70 kg person, more ideally between about 2 and 5 grams per day. The dosing on a body weight basis may range from about 0.01 to about 0.10 grams per kg body weight, more ideally between 0.02 and 0.07 grams/kg body weight.

Dosing for ω-3 fatty acids and EPA in particular are given above.

The present invention provides, in another embodiment, a method for reducing tumor growth rate in a patient, such as a mammal, preferably a human. The method comprises administering to the patient the above-described composition, which comprises HMB in amounts sufficient to reduce tumor growth rate, wherein, upon administration of the composition to the patient, the tumor growth rate is reduced.

The amount of HMB that is sufficient to attenuate tumor growth in a given patient can be determined in accordance with methods well known in the art. When treating tumor growth in a patient, desirably, the composition comprising HMB is administered to a patient suffering from tumor growth in such an amount, in such a manner, and over such a period of time that the patient's tumor growth rate will decrease. An example, within the context of treating the tumor growth in an adult human, when the composition is orally administered about twice a day for a minimum of two weeks; the dose is sufficient to provide at least about 2 gm HMB/day.

The present invention provides, in another embodiment, a method for down regulating the expression and/or activity of protein kinase C. Examples I-IV show that both EPA and HMB attenuated PIF-induced activation of protein kinase C (PKC) and the subsequent degradation of IκBα and nuclear accumulation of nuclear factor-κB (NF-κB).

The present invention provides, in another embodiment, a method for down regulating the expression and/or activity of nuclear factor kappa-B. Examples I-IV show that both EPA and HMB attenuated PIF-induced activation of protein kinase C (PKC) and the subsequent degradation of IκBα and nuclear accumulation of nuclear factor-κB (NF-κB).

The present invention provides, in another embodiment, a method for down regulating the expression and/or activity of ubiquitin-conjugating enzymes. Examples I-IV show that this was accompanied by a reduction in the expression of $E2_{14k}$ ubiquitin-conjugating enzyme. The combination of EPA and HMB was at least as effective or more effective than either treatment alone. These results show that both EPA and HMB preserve muscle mass by attenuating protein degradation through down regulation of the increased expression of key regulatory components of the ubiquitin-proteasome proteolytic pathway.

The present invention provides, in another embodiment, a method for down regulating the expression and/or activity of components of 26S proteasome. Examples I-IV show that proteasome activity, determined by the 'chymotrypsin-like' enzyme activity, was attenuated by HMB. Protein expression of the 20S a or β-subunits was reduced by at least 50%, as were the ATPase subunits MSS1 and p42 of the 19S proteasome regulatory subunit.

In addition to the above-mentioned methods of inhibiting protein degradation, the present invention also provides, in another embodiment, a method for stimulating new protein synthesis in a patient having a disease-associated wasting condition, comprising administering an effective amount of HMB. In such patients, the level of protein synthesis is usually depressed from normal as an effect of the disease-associated conditions. In one aspect, protein synthesis in such patients is stimulated by at least 6%, 10%, 25%, 50% or more relative to the pre-administration depressed levels. The status of muscle is dynamic, a net effect of both protein synthesis and degradation. It is unexpectedly and surprisingly found that HMB affects both processes in opposite directions—while protein synthesis is stimulated, protein degradation is inhibited—such that the overall net gain in lean muscle mass is magnified in wasting patients. The ratio of synthesis to degradation can thus be magnified 10 fold, 14 fold, 20 fold, 30 fold, 40 fold or more. This is an ideal outcome for those suffering from disease-associated wasting conditions like cachexia, COPD and AIDS. In another aspect the stimulation is effected by an oral route of administration of the HMB. The HMB may be administered in combination with EPA; and may be administered with or without supporting protein, amino acids or other nutritional components.

Example I

Prevention of Weight Loss and Attenuation of Protein Degradation in Animals with Cancer Cachexia This study evaluates the effect of HMB, in comparison with EPA or combination, on weight loss induced by the MAC16 tumor and the mechanisms involved. Weight loss induced by the MAC16 tumor is primarily induced by PIF.

Pure strain male NMRI mice (average weight 25 g) were obtained from our own inbred colony and were transplanted with fragments of the MAC16 tumor s.c. into the flank by means of a trochar, selecting from donor animals with established weight loss as described in Bibby, M. C. et al. Characterization of a transplantable adenocarcinoma of the mouse colon producing cachexia in recipient animals. J. Natl. Cancer Inst., 78: 539-546, 1987. Transplanted animals were fed a rat and mouse breeding diet (Special Diet Services, Witham, United Kingdom) and water ad libitum, and weight loss was evident 10-12 days after tumor implantation. Animals just prior to the development of weight loss were randomized to receive daily either EPA (in olive oil), HMB (in PBS) or the combination as described in the figure legends administered p.o. by gavage, while control animals received either olive oil or PBS. EPA (98% as free acid) was purchased from Biomol Research Laboratories Inc., PA, USA. HMB (as the calcium salt) was obtained from Abbott Laboratories, Columbus, Ohio, USA. All groups contained a minimum of 6 mice. Tumor volume, body weight and food and water intake were monitored daily. Animals were terminated by cervical dislocation when the body weight loss reached 25%, and all studies were conducted according to the UKCCR Guidelines for the care and use of laboratory animals. The soleus muscles were quickly dissected out, together with intact tendons, and maintained in isotonic ice-cold saline before determination of protein degradation.

Freshly dissected soleus muscles were fixed via the tendons to aluminium wire supports, under tension, at approximately resting length to prevent muscle shortening and pre-incubated for 45 min in 3 ml of oxygenated (95% oxygen:5% carbon dioxide) Krebs-Henseleit bicarbonate buffer (pH 7.4) containing 5 mM glucose and 0.5 mM cycloheximide. Protein degradation was determined by the release of tyrosine over a 2 h period as described in Waalkes, T. P. et al. A fluorimetric method for the estimation of tyrosine in plasma and tissues. J. Lab. Clin. Med., 50: 733-736, 1957.

Functional proteasome activity was determined by measuring the 'chymotrypsin-like' enzyme activity, the predominant proteolytic activity of the β-subunits of the proteasome according to the method of Orino, E. et al. ATP-dependent reversible association of proteasomes with multiple protein components to form 26S complexes that degrade ubiquitinated proteins in human HL-60 cells. FEBS Lett., 284: 206-210, 1991. Muscles were rinsed with ice-cold PBS, minced and sonicated in 20 mM Tris. HCl, pH 7.5, 2 mM ATP, 5 mM $MgCl_2$ and 1 mM DTT. The sonicate was then centrifuged for 10 min at 18,000 g, at 4° C. and the supernatant was used to determine 'chymotrypsin-like' enzyme activity by the release of aminomethyl coumarin (AMC) from the fluorogenic substrate succinyl-LLVY-AMC. Activity was measured in the absence and presence of the specific proteasome inhibitor lactacystin (10 µM). Only lactacystin suppressible activity was considered to be proteasome specific.

For Western blotting samples of soleus muscle cytosolic protein (2 to 5 µg), obtained from the above assay, were resolved on 10% SDS-PAGE and transferred to 0.45 µm nitrocellulose membrane (Hybond™, Amersham Life Science Products, Bucks, United Kingdom), which had been blocked with 5% Marvel in PBS. The primary antibodies for MSS1 and p42 were used at a dilution of 1:5000, for 20S proteasome α-subunits at 1:1500 and for β-subunits at 1:1000, while the antibody for $E2_{14k}$ was used at a dilution of 1:500. The secondary antibodies were used at a dilution of 1:2000. Mouse monoclonal antibodies to 20S proteasome subunits a 1, 2, 3, 5, 6 and 7 (clone MCP 231), 20S proteasome subunit β3 (HC10), 19S regulator ATPase subunit Rpt 1 (S7, Mss1; clone MSS1-104) and 19S regulator ATPase subunit Rpt 4 (S106, p42; clone p42-23) were purchased from Affiniti Research Products, Exeter, United Kingdom. Rabbit polyclonal antisera to ubiquitin-conjugating enzyme E2 (anti-UBC2 antibody) was a gift from Dr. Simon Wing, McGill University, Montreal, Quebec, Canada. Peroxidase-conjugated goat anti-rabbit and rabbit anti-mouse secondary antibodies were from Dako Ltd., Cambridge, United Kingdom. Incubation was carried out for 2 h at room temperature, and developed by chemiluminescence (ECL; Amersham).

Figure 2A:
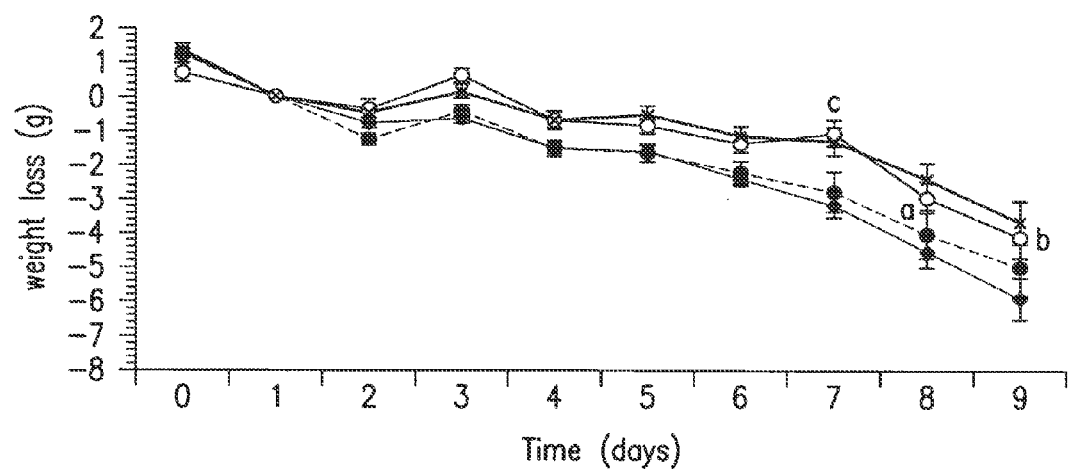
FIG. 2 presents dose-response curves for the effect of HMB on body weight (A) and tumor volume (B) in mice bearing the MAC16 tumor. HMB (in PBS) was administered orally by gavage on a daily regime at a concentration of 0.05 (●), 0.125 (○) and 0.25 g|kg (X). Control mice received PBS alone (◆). The results shown are the mean±SEM, where n=20.
Figure 3:
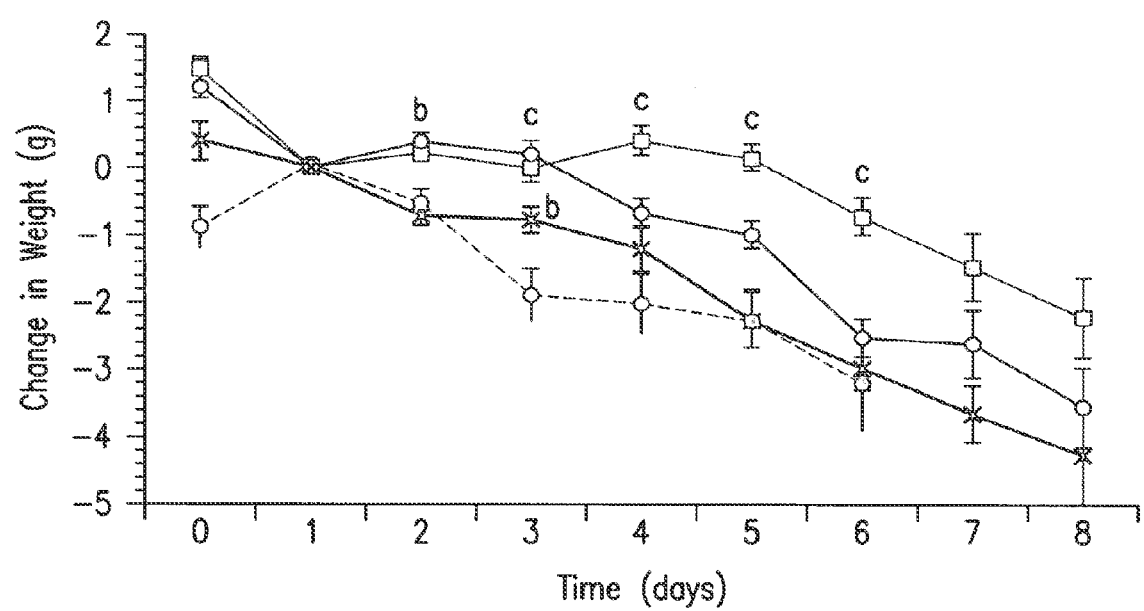
FIG. 3 presents the effect of HMB (0.25 g|kg; ■), EPA (0.6 g|kg; X) and the combination (○) together with PBS controls (●) on body weight of mice bearing the MAC16 tumor. Results shown are mean±SEM, where n=20.
Figure 4A:
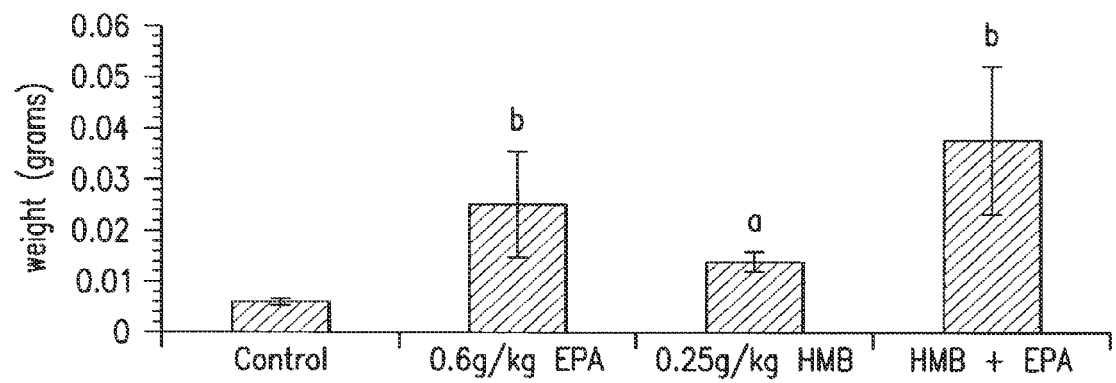
FIG. 4 presents the weight of soleus muscles (A) and rate of protein degradation in soleus muscle (B) of mice bearing the MAC16 tumor and treated with either EPA (0.6 g|kg), HMB (0.25 g|kg) or the combination for 3 days. Values shown are mean±SEM, where n=6.

A dose-response relationship of HMB on weight loss in mice bearing the MAC16 tumor is shown in FIG. 2. Doses of HMB greater than 0.125 g/kg caused a significant reduction in weight loss (FIG. 2A). Differences from the control group are indicated as a, $p<0.05$; b, $p<0.01$ and c, $p<0.005$. Attenuation of weight loss was not accompanied by an alteration in food and water intake. A dose level of 0.25 g/kg was chosen for all subsequent experiments. The effect of HMB, EPA and the combination of HMB and EPA on weight loss in MAC16 cachectic tumour-bearing mice is shown in FIG. 3. Differences from the control group are indicated as a, $p<0.05$; b, $p<0.01$ or c, $p<0.005$. A suboptimal dose of EPA was chosen to investigate interactions with HMB. All treatments caused a significant increase in soleus muscle weight (FIG. 4A), and a significant reduction in tyrosine release (FIG. 4B), indicating a reduction in total protein degradation. Differences from the PBS control group are indicated as a, $p<0.05$, b, $p<0.01$ or c, $p<0.005$. At the doses chosen, HMB was as effective as EPA.

Figure 5:
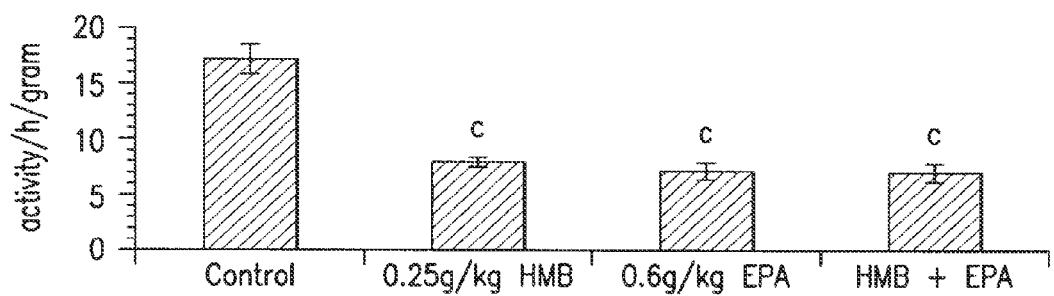
FIG. 5 presents the effect of HMB and EPA on proteasome functional activity, determined as the 'chymotrypsin-like' enzyme activity, in gastrocnemius muscle of mice bearing the MAC16 tumor and treated for 3 days. Results are shown as mean±SEM, where n=6.
Figure 6A:
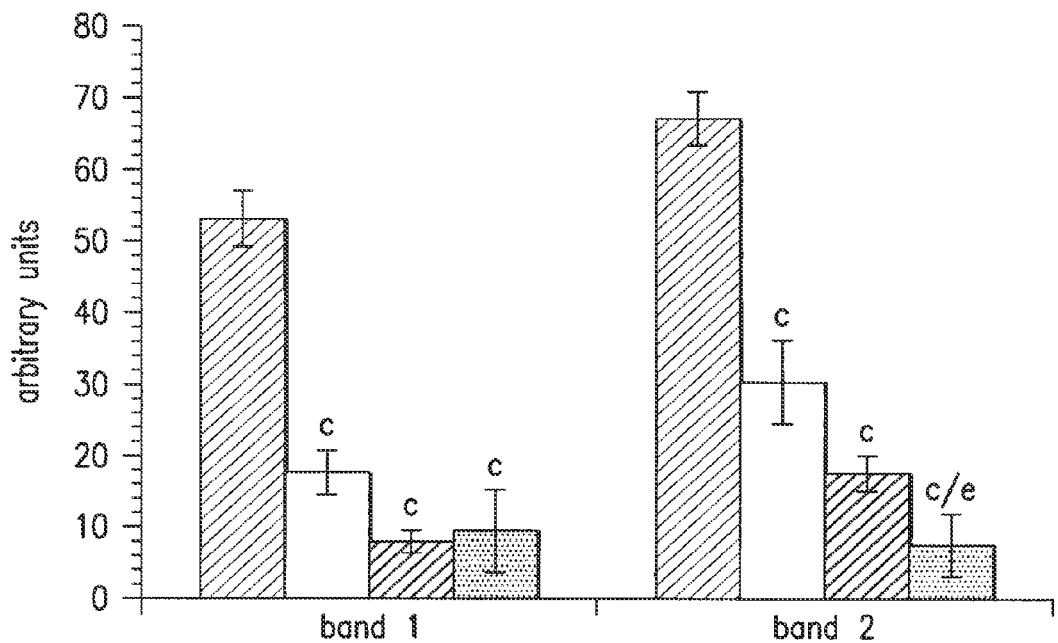
FIG. 6 presents the expression of proteasome 20S α-subunits (A) and β-subunits (B), detected by Western blotting, in gastrocnemius muscle of mice treated for 3 days with PBS (Control), HMB (0.25 g|kg), EPA (0.6 g|kg) or the combination. Densitometric analysis of the blots (n=6) are shown. A. control (closed bars), HMB (open bars), EPA (hashed bars) and combination (dotted bars)
Figure 6B:
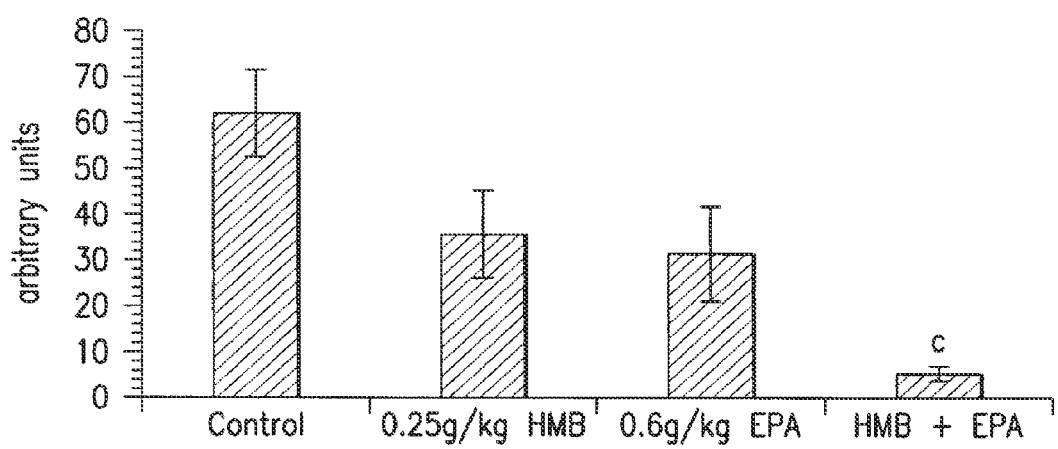

Proteasome expression has been shown to be elevated in gastrocnemius muscles of mice bearing the MAC16 tumor and this increased gene expression has been shown to be attenuated by EPA. The results in FIG. 5 show that functional proteasome activity, as determined by 'chymotrypsin-like' enzyme activity, was attenuated by HMB to the same extent as EPA at the doses chosen, and that the combination of HMB and EPA did not produce a further depression in activity. Differences from control are indicated as c, $p<0.005$. Protein expression of proteasome subunits was analysed by Western blotting of supernatants from sonicated muscle tissues. Expression of 20S proteasome α-subunits, the structural units of the proteasome was attenuated by both HMB and EPA, and there was some indication of a further decrease of band 2 for the combination (FIG. 6A). Differences from control are shown as c, $p<0.001$, while differences from HMB are shown as e, $p<0.01$. Expression of the 20S proteasome β-subunits, the catalytic subunits of the proteasome, were also attenuated by HMB and EPA, but the combination was more effective than either agent alone (FIG. 6B). Differences from control are shown as c, $p<0.001$.

Figure 7A:
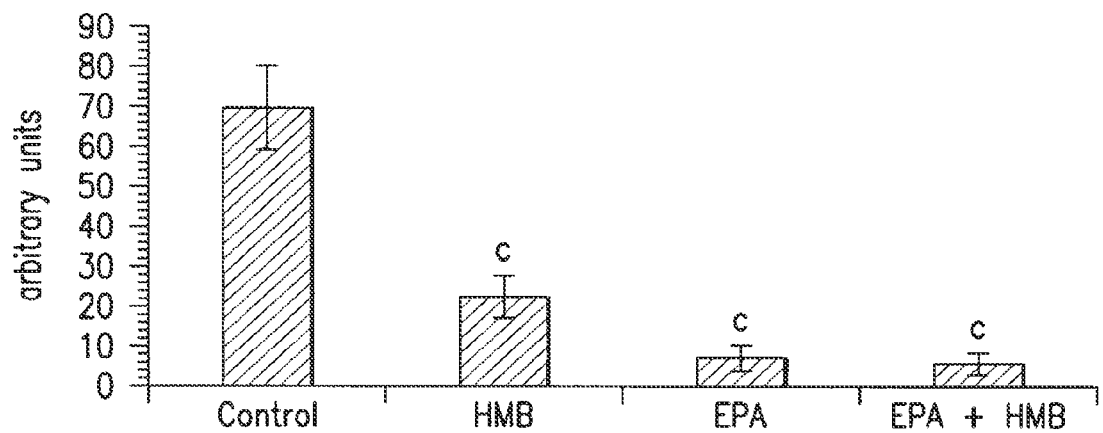
FIG. 7 presents the expression of proteasome 19S subunits, MSS1 (A) and p42 (B), detected by Western blotting, in gastrocnemius muscle of mice treated for 3 days with PBS (Control), HMB (0.25 g|kg), EPA (0.6 g|kg) or the combination (HMB+EPA). Densitometric analysis of the blots (n=6) are shown.
Figure 7B:
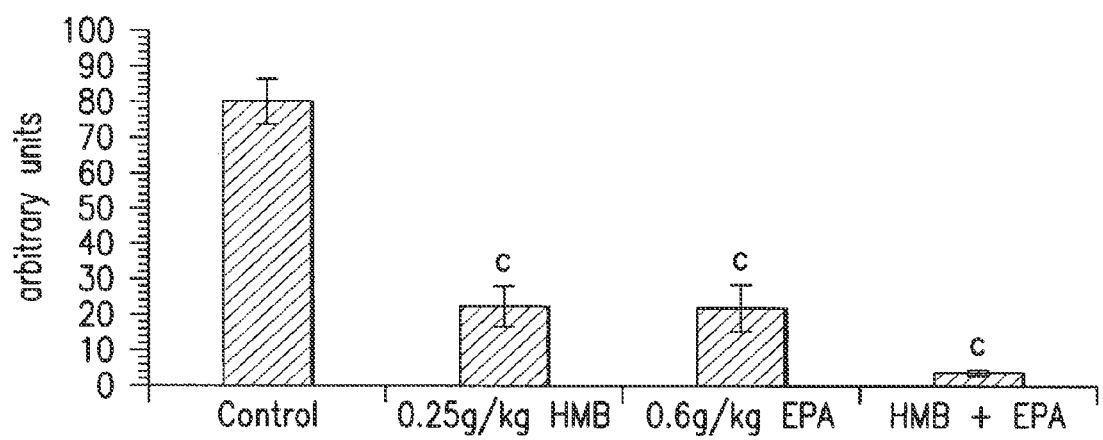
Figure 8:
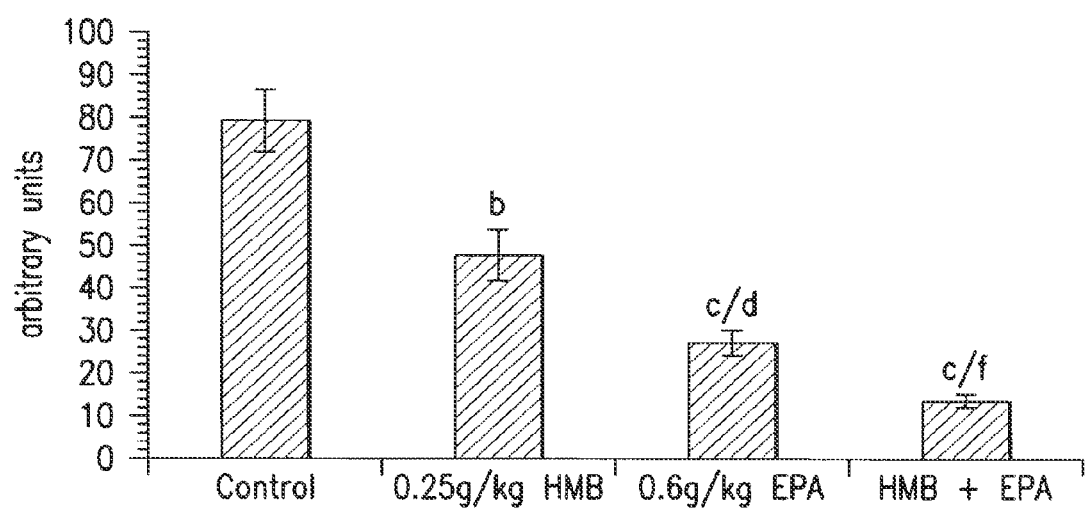
FIG. 8 presents the expression of $E2_{14k}$, detected by Western blotting, in gastrocnemius muscle of mice treated for 3 days with PBS (Control), HMB (0.25 g|kg), EPA (0.6 g|kg) or the combination (HMB+EPA). Densitometric analysis of the blots (n=6) are shown.

Expression of MSS1, an ATPase subunit of the 19S proteasome regulatory complex is shown in FIG. 7A. Both HMB and EPA attenuated MSS1 expression, but the combination did not appear to produce a further reduction. Similar results were obtained with p42, another ATPase subunit of the 19S regulator, that promotes ATP dependent association of the 20S proteasome with the 19S regulator to form the 26S proteasome (FIG. 7B). Differences from control are shown as c, $p<0.001$. Again both HMB and EPA appeared to be equally effective, while the combination did appear to reduce p42 expression further. Expression of the ubiquitin-conjugating enzyme, $E2_{14k}$, was also reduced by both HMB and EPA, while the combination caused a further reduction in expression (FIG. 8). Differences from control are shown as b, $p<0.01$ and c, $p<0.001$, while differences from HMB alone are shown as d, $p<0.05$ and f, $p<0.001$. These results confirm HMB to be as effective as EPA in attenuating loss of muscle mass, protein degradation and down-regulation of the ubiquitin-proteasome proteolytic pathway, and this mechanism appears to be responsible for the preservation of muscle mass in cachectic mice bearing the MAC16 tumor.

This study has shown that HMB is effective in attenuating the development of cachexia or involuntary weight loss in mice bearing the MAC16 tumor and produced a reduction in protein degradation in skeletal muscle by down regulating the increased expression of the ubiquitin-proteasome pathway. Thus HMB is as effective as EPA in reducing protein expression of the 20S proteasome α and β subunits, as well as two subunits of the 19S regulator MSS1 and p42, expression of $E2_{14k}$ and proteasome proteolytic activity.

Example II

Attenuation of Tumor Growth in Animals

The animal study described in Example I above also evaluated the effect of HMB on tumor growth rate in MAC16 cachectic tumor-bearing mice. The experiment was conducted as described in Example I.

Figure 2B:
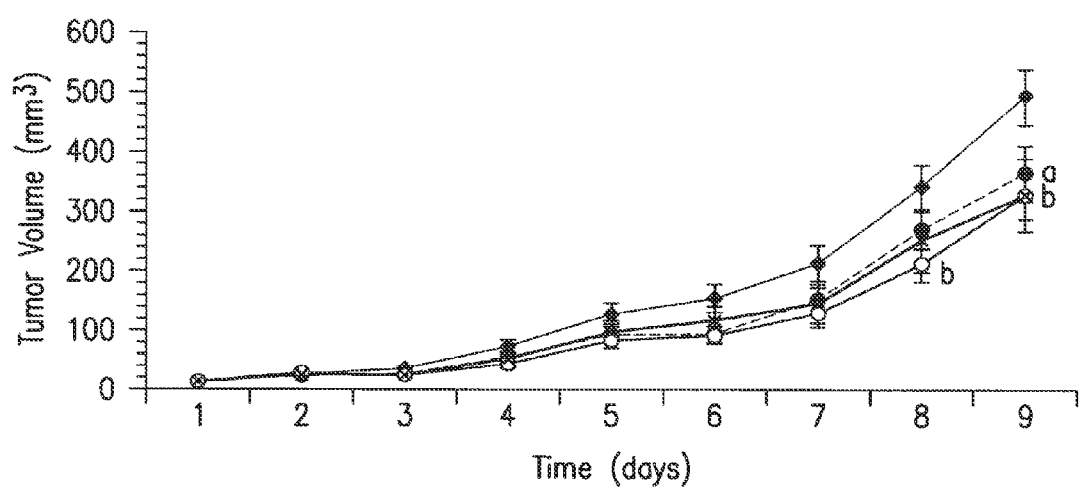

A dose-response relationship of HMB alone on tumor growth rate in mice bearing the MAC16 tumor is shown in FIG. 2B. Differences from the control group are indicated as a, $p<0.05$; b, $p<0.01$ and c, $p<0.005$. Doses of HMB greater than 0.125 g/kg caused a significant reduction in tumor growth rate. Attenuation of tumor growth was not accompanied by an alteration in food and water intake.

Example III

Attenuation of Protein Depredation in Murine Myotubes

This study examines the effect of HMB on PIF-induced protein degradation and signalling pathways in murine myotubes to determine the mechanism of the attenuation of the increased expression of the ubiquitin-proteasome proteolytic pathway.

$C_2C_{12}$ myotubes were routinely passaged in DMEM supplemented with 10% FCS, glutamine and 1% penicillin-streptomycin under an atmosphere of 10% $CO_2$ in air at 37° C. Myotubes were formed by allowing confluent cultures to differentiate in DMEM containing 2% HS, with medium changes every 2 days.

PIF was purified from solid MAC16 tumors (Todorov, P. et al. Characterization of a cancer cachectic factor. Nature, 379: 739-742, 1996.) excised from mice with a weight loss of 20 to 25%. Tumors were homogenised in 10 mM Tris-HCl, pH 8.0, containing 0.5 mM phenylmethylsulfonyl fluoride, 0.5 mM EGTA and 1 mM dithiothreitol at a concentration of 5 ml/g tumor. Solid ammonium sulfate was added to 40% w/v and the supernatant, after removal of the ammonium sulfate, was subjected to affinity chromatography using anti-PIF monoclonal antibody coupled to a solid matrix as described in Todorov, P. et al Induction of muscle protein degradation and weight loss by a tumor product. Cancer Res., 56: 1256-1261, 1996. The immunogenic fractions were concentrated and used for further studies.

Myotubes in six-well multidishes were labeled with L-[2, 6-$^3$H] phenylalanine (0.67 mCi/mmole) for 24 h in 2 ml DMEM containing 2% HS. They were then washed three times in PBS followed by a 2 h incubation at 37° C. in DMEM without phenol red until no more radioactivity appeared in the supernatant. These myotubes were then further incubated for 24 h in the presence of PIF, with and without EPA or HMB, in fresh DMEM without phenol red, to prevent quenching of counts, and in the presence of 2 mM cold phenylalanine to prevent reincorporation of radioactivity. The amount of radioactivity released into the medium was expressed as a percentage of control cultures not exposed to PIF to determine total protein degradation.

For measurement of arachidonic acid release, myotubes in six-well multi dishes containing 2 ml DMEM with 2% HS were labeled for 24 h with 10 μM arachidonic acid (containing 1 μCi of [$^3$H] arachidonate/ml) (Smith, H. et al. Effect of a cancer cachectic factor on protein synthesis/degradation in murine $C_2C_{12}$ myoblasts: Modulation by eicosapentaenoic acid. Cancer Res., 59: 5507-5513, 1999). Cells were then washed extensively with PBS to remove traces of unincorporated [³H] arachidonate and either EPA or HMB was added 2 h prior to PIF. After a further 24 h 1 ml of medium was removed to determine the radioactivity released.

The functional activity of the β subunits of the proteasome was determined as the 'chymotrypsin-like' enzyme activity obtained fluorimetrically according to the method of Orino, E. et al. ATP-dependent reversible association of proteasomes with multiple protein components to form 26S complexes that degrade ubiquitinated proteins in human HL-60 cells. FEBS Lett., 284: 206-210, 1991. Myotubes were exposed to PIF for 24 h with or without EPA or HMB added 2 h prior to PIF and enzyme activity was determined in a supernatant fraction (Whitehouse, A. S. et al. Increased expression of the ubiquitin-proteasome pathway in murine myotubes by proteolysis-inducing factor (PIF) is associated with activation of the transcription factor NF-κB. Br. J. Cancer, 89: 1116-1122, 2003) by the release of aminomethyl coumarin (AMC) from succinyl-LLVY-AMC (0.1 mM) in the presence or absence of the specific proteasome inhibitor lactacystin (10 μM) (Fenteany, G. et al. Lactacystin, proteasome function and cell fate. J. Biol. Chem., 273: 8545-8548, 1998). Only lactacystin suppressible activity was considered to be proteasome specific. Activity was adjusted for the protein concentration of the sample, determined using the Bradford assay (Sigma Chemical Co., Dorset, United Kingdom) using bovine serum albumin as standard.

For Western blot analysis, cytosolic protein (2 to 5 μg) obtained for the above assay were resolved on 10% SDS-PAGE and transferred to 0.45 μm nitrocellulose membrane, which had been blocked with 5% Marvel in PBS, at 4° C. overnight. The primary antibodies were used at a dilution of 1:100 (anti-actin and $PKC_\alpha$); 1:500 (anti-ERK1 and 2); 1:1000 (anti-20S proteasome β-subunit and I-κBα); 1:1500 (anti-20S proteasome α-subunit) or 1:5000 (anti-p42), while the secondary antibodies were used at a dilution of 1:2000. Incubation was carried out for 2 h at room temperature and development was by ECL. Loading was quantitated by actin concentration.

DNA binding proteins were extracted from myotubes by the method of Andrews, N. C. et al. A rapid micropreparation technique for extraction of DNA-binding proteins from limiting numbers of mammalian cells. Nucleic Acids Res., 19: 2499, 1991, which utilizes hypotonic lysis followed by high salt extraction of nuclei. The EMSA (electrophoretic mobility shift assay) binding assay was carried out according to the manufacturer's instructions.

Figure 9A:
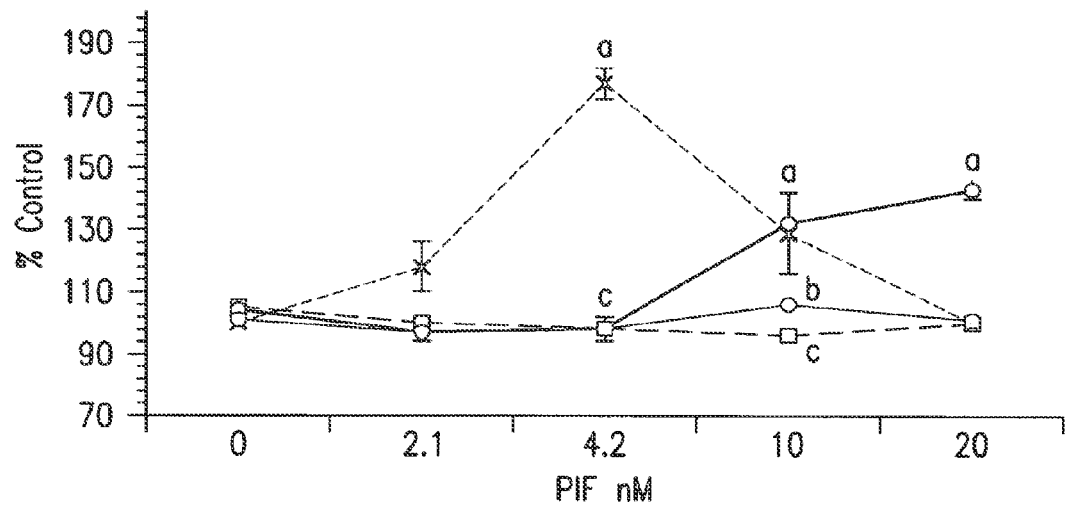
FIG. 9 (A) presents the effect of PIF on total protein degradation in $C_2C_{12}$ myotubes in the absence (X) or presence of either 50 μM EPA (□), or 25 μM (○) or 50 μM (●) HMB. Measurements were made 24 h after the addition of PIF and are shown as mean±SEM, where n=9. 1(B) presents the chymotryptic activity of soluble extracts of murine myotubes treated with PIF in the absence or presence of EPA (50 μM) or HMB (25 or 50 μM). The symbols are the same as in (A). The results are shown as mean±SEM, where n=9.

Since protein degradation and activation of the ubiquitin-proteasome proteolytic pathway in mice bearing the MAC16 tumor is thought to be mediated by PIF, mechanistic studies on the effect of HMB on protein degradation were carried out in murine myotubes treated with PIF. PIF-induced total protein breakdown with a typical bell-shaped dose-response curve, as previously reported by Gomes-Marcondes, et al Development of an in-vitro model system to investigate the mechanism of muscle protein catabolism induced by proteolysis-inducing factor. Br. J. Cancer, 86: 1628-1633, 2002 with a maximal effect at 4 nM. The effect of EPA has been previously shown (Smith, H. J. et al. Effect of a cancer cachectic factor on protein synthesis/degradation in murine $C_2C_{12}$ myoblasts: Modulation by eicosapentaenoic acid. Cancer Res., 59: 5507-5513, 1999; Whitehouse, A. S. et al. Induction of protein catabolism in myotubes by 15(S)-hydroxyeicosatetraenoic acid through increased expression of the ubiquitin-proteasome pathway. Br. J. Cancer, 89: 737-745, 2003; and Whitehouse, A. S. et al. Increased expression of the ubiquitin-proteasome pathway in murine myotubes by proteolysis-inducing factor (PIF) is associated with activation of the transcription factor NF-κB. Br. J. Cancer, 89: 1116-1122, 2003) to be effective at 50 μM, and the data in FIG. 9A shows that at a concentration of 50 μM both HMB and EPA were equally effective in attenuating PIF induced protein degradation. There was also some attenuation at 25 μM HMB at low, but not at high concentrations of PIF. Differences from control in the absence of PIF are indicated as a, p<0.005, while differences form control with PIF (for groups with additions of HMV or EPA) are indicated as b, p<0.01 and c, p<0.005.

PIF-induced protein degradation has previously been shown to be due to an increased expression of the regulatory components of the ubiquitin-proteasome proteolytic pathway by Lorite, M. J., Smith, H. J., Arnold, J. A., Morris, A., Thompson, M. G. and Tisdale, M. J. Activation of ATP-ubiquitin-dependent proteolysis in skeletal muscle in vivo and murine myoblasts in vitro by a proteolysis-inducing factor (PIF). Br. J. Cancer, 85: 297-302, 2001 and Gomes-Marcondes, M. C. C., Smith, H. J., Cooper, J. C. and Tisdale, M. J. Development of an in-vitro model system to investigate the mechanism of muscle protein catabolism induced by proteolysis-inducing factor. Br. J. Cancer, 86: 1628-1633, 2002.

Figure 9B:
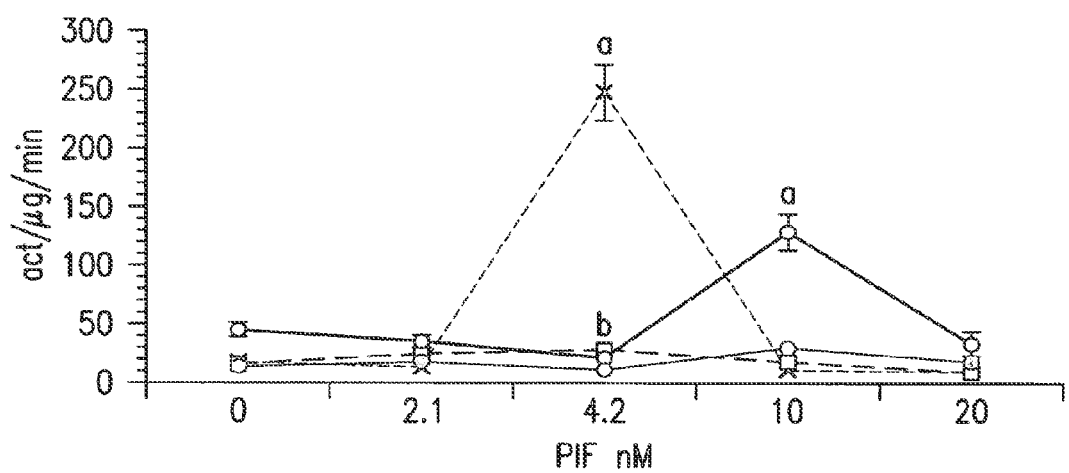
Figure 10A:
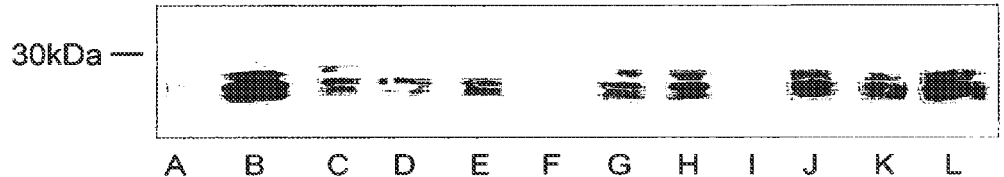
FIG. 10 presents the effect of EPA and HMB on PIF-induction of 20S proteasome α-subunit (A), β-subunit (B) and p42 (C). The actin loading control is shown in (D). Western blots of soluble extracts of $C_2C_{12}$ myotubes 24 h after treatment with PIF alone (lanes A-C) or with PIF in the presence of 50 μM EPA (lanes D-F), 50 μM HMB (lanes G-I) or 25 μM HMB (lanes J-L) at a concentration of PIF of 4.2 nM (lanes B, E, H and K) or 10 nM (lanes C, F, I and L). Control cultures received PBS (lane A), 50 μM EPA (lane D), 50 μM HMB (lane G) or 25 μM HMB (lane J). The blots shown are representative of three separate experiments.
Figure 10B:
Figure 10C:
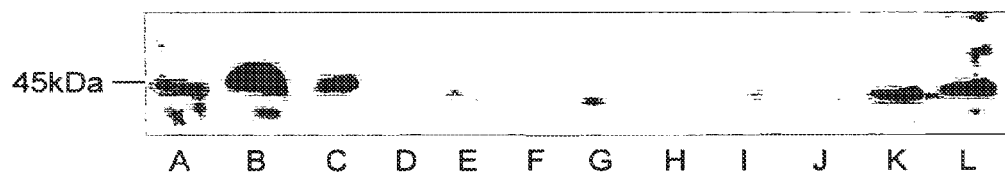
Figure 10D:

The functional activity of this pathway is measured by the 'chymotrypsin-like' enzyme activity, the predominant proteolytic activity of the β-subunits of the proteasome. PIF induced an increase in 'chymotrypsin-like' enzyme activity, which was maximal at 4.2 nM. The effect of PIF was completely attenuated by 50 μM EPA and both 25 and 50 μM HMB. (FIG. 9B, differences from control are shown as a, p<0.001, while differences in the presence of EPA or HMB are shown as b, p<0.001). A similar effect was observed on expression of proteasome 20S α subunits, β subunits and p42, an ATPase subunit of the 19S regulator that promotes ATP-dependent association of the 20S proteasome with the 19S regulator to form the 26S proteasome (FIG. 10). In all cases expression was increased by PIF at 4.2 and 10 nM and this was attenuated by EPA and HMB at 50 μM, but not at 25 μM. These results confirm that HMB attenuates protein degradation through an effect on PIF induction of the ubiquitin-proteasome pathway.

Example IV

Effect on Activity of Mediator of Signaling in Inflammation and Proteolysis

The in vitro study described in Example III above also evaluated the effect of HMB on molecules that are key mediators in the pathway of inflammation. This experiment was conducted as described in Example III.

Figure 12A:
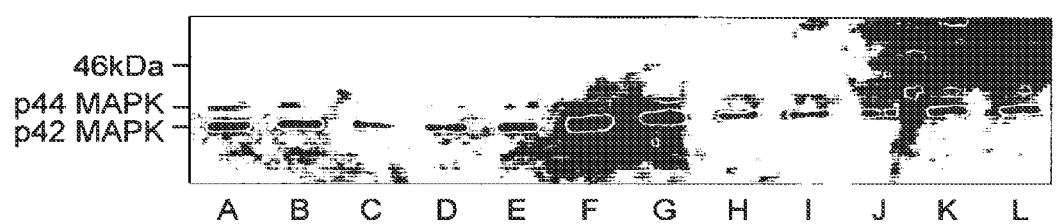
FIG. 12 presents Western blots of total ERK 1/2 (p44 and p42) (A) and active (phosphorylated) ERK 1/2 (B) in soluble extracts of murine myotubes treated with PIF alone (lanes A-C) or with PIF in the presence of 50 μM EPA (lanes D-F), 50 μM HMB (lanes G-I) or 25 μM HMB (lanes J-L) at a PIF concentration of 4.2 nM (lanes B, E, H and K) or 10 nM (lanes C, F, I and L). Control cells received either PBS (lane A), 50 μM EPA (lane D), 50 μM HMB (lane G) or 25 μM HMB (lane J). The blots shown are representative of three separate experiments.
Figure 12B:
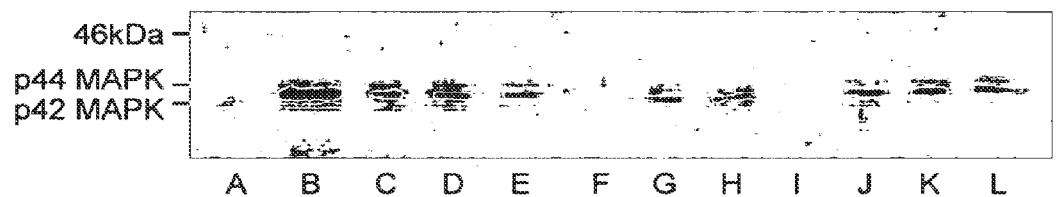

Activation of PKC has been shown to activate extracellular signal-regulated kinase (ERK) cascade of MAPK signalling pathways (Toker, A. Signalling through protein kinase C. Front. Biosci., 3: 1134-1147, 1998; Wolf, I. and Seger, R. The mitogen-activated protein kinase signalling cascade: from bench to bedside. IMAJ., 4: 641-647). The activated ERKs, e.g., ERK1 (or p44 MAPK) and ERK2 (or p42 MAPK), are able to phosphorylate and consequently activate cytosolic phospholipase A2, the rate-limiting enzyme in pathways involving arachidonic acid release in inflammation. In addition, PIF has been shown to induce phosphorylation of p42/44 MAPK, while the total MAPK remained unchanged and to be involved in PIF-induced proteasome expression (Smith, H. J. et al. Signal transduction pathways involved in proteolysis-inducing factor induced proteasome expression in murine myotubes. Br. J. Cancer, 89: 1783-1788, 2003). The effect of EPA and HMB on this process is shown in FIG. 12. PIE induced an increased phosphorylation of p42/44 that was maximal at 4.2 nM and this effect was completely attenuated by both EPA and HMB at 50 µM, but not HMB at 25 µM. The ability of HMB to attenuate ERK 1/2 phosphorylation may be important in inhibition of PIF-induced proteasome expression by HMB.

Figure 11A:
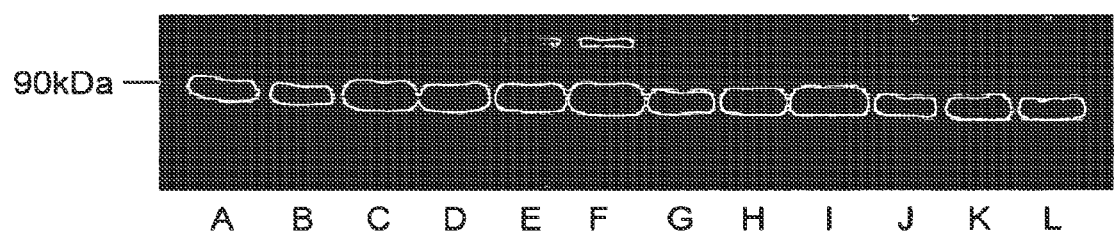
FIG. 11 presents the Western blot of the effect of PIF on cytoplasmic (A) and membrane-bound (B) $PKC_\alpha$ in murine myotubes. Cells were treated with PIF alone (lanes A-C) or with PIF in the presence of 50 μM EPA (lanes D-F), 50 μM HMB (lanes G-I) or 25 μM HMB (lanes J-L) at 4.2 nM (lanes B, E, H and K) or 10 nM PIF (lanes C, F, I and L). Control cells received PBS (lane A), 50 μM EPA (lane D), 50 μM HMB (lane G) or 25 μM HMB (lane J). The blots shown are representative of three separate experiments.
Figure 11B:
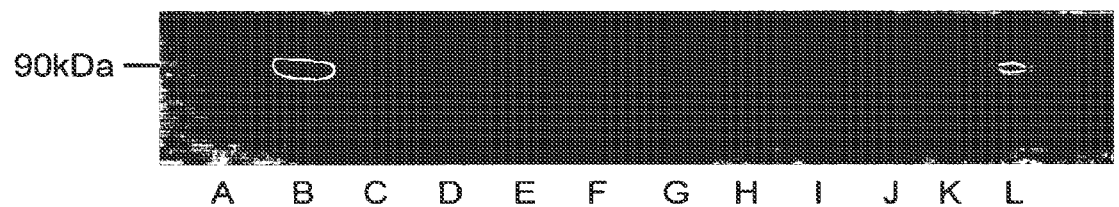

Experiments using mutants of PKC as well as inhibitors of this enzyme show that this forms a central mediator of intracellular signalling by PIE. PKC is likely to be involved in phosphorylation (and degradation) of I-κBα leading to nuclear accumulation of NF-κB and increased gene transcription. PIF stimulates translocation of $PKC_\alpha$ from the cytoplasm to the plasma membrane (FIG. 11) resulting in activation with a maximum effect at 4.2 nM PIF as with protein degradation (FIG. 9). This process was effectively attenuated by both EPA and HMB at 50 µM; while HMB was less effective at 25 µM (FIG. 11). This suggests that PIF-induced stimulation of PKC is attenuated by HMB through inhibition of PKC.

Figure 13A:
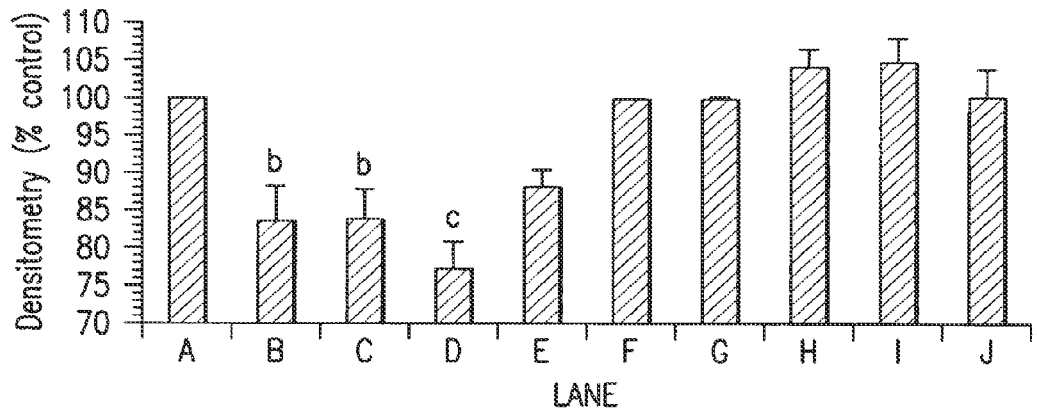
FIG. 13 presents the effect of exposure of $C_2C_{12}$ myotubes for 30 min on cytosolic levels of IκBα (A), determined by Western blotting, and activation of NF-κB binding to DNA, as determined by EMSA (B and C). The densitometric analysis is an average of 3 replicate blots or EMSAs. (A) Myotubes were treated with PIF alone (lanes A-E) or with PIF in the presence of 50 μM HMB at a concentration of 0 (lanes A and F), 2.1 (lanes B and G), 4.2 (lanes C and H), 10.5 (lanes D and I) or 16.8 nM PIF (lanes E and J). In (B) and (C) myotubes were treated with 0, 2.1, 4.2, 10.5 or 16.8 nM PIF, in the absence (dark bars) or presence (open bars) of 25 μM HMB (B) or 50 μM HMB (C).
Figure 13B:
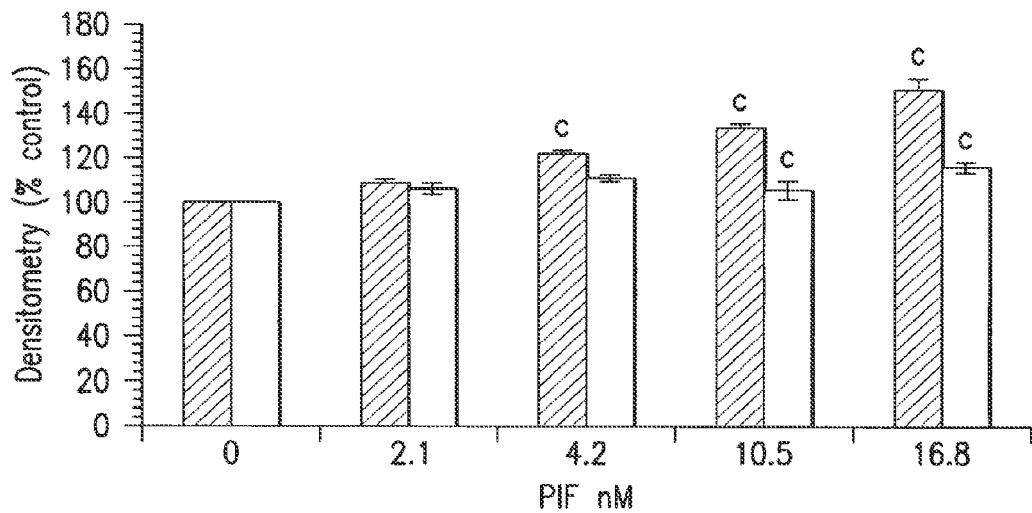
Figure 13C:
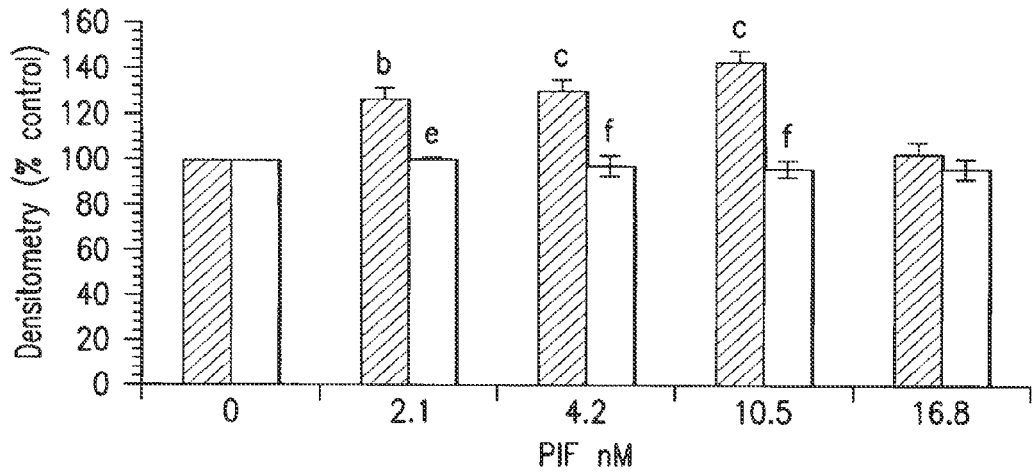

As previously discussed PIF induces degradation of I-κBα and stimulates nuclear accumulation of NF-κB and this process has been shown to be attenuated by 50 µM EPA (Whitehouse, A. S. et al. Increased expression of the ubiquitin-proteasome pathway in murine myotubes by proteolysis-inducing factor (PIF) is associated with activation of the transcription factor NF-κB. Br. J. Cancer, 89: 1116-1122, 2003). The results in FIG. 13A show HMB at 50 µM to effectively attenuate I-κBα degradation in the presence of PIF in murine myotubes, and prevent nuclear accumulation of NF-κB (FIG. 13C). Differences from 0 nM PIF are shown as b, $p<0.01$ and c, $p<0.001$. Only partial inhibition of binding of NF-κB to DNA was observed when HMB was used at a concentration of 25 µM (FIG. 13B). Differences from 0 nM PIF b=$p<0.01$ and c=$p<0.001$. Differences between 50 uM HMB and PIF treated against PIF alone at the same concentration e=$p<0.01$ and f=$p<0.001$. These results suggest that the overall effect of HMB is comparable to that of EPA in preventing movement of NF-κB into the nucleus with concomitant activation of gene expression.

Thus HMB appears to be an effective agent in the treatment of cytokine induced inflammation and muscle wasting in cancer cachexia. HMB appears to exert its effect by inhibition of PKC activity, and resultant stabilization of the cytoplasmic IκB/NF-κB complex. Since these molecules are key mediators in the pathway of inflammation, HMB appears to be an anti-inflammatory compound.

Example V

Composition of a Nutritional Product to Prevent Involuntary Weight Loss

The specific list of materials for manufacturing the nutritional product of this Example is presented in Table 1. Of course, various changes in specific ingredients and quantities may be made without departing from the scope of the invention.

TABLE 1

LIST OF MATERIALS

| INGREDIENT | AMOUNT (KG) |
|---|---|
| WATER | 316 |
| ULTRATRACE/TRACE MINERAL PREMIX | 0.06 |
| ZINC SULFATE | 0.033 |
| MANGANESE SULFATE | 0.0082 |
| SODIUM MOLYBDATE | 0.00023 |
| CHROMIUM CHLORIDE | 0.00029 |
| SODIUM SELENITE | 0.000098 |
| POTASSIUM CHLORIDE | 0.072 |
| SODIUM CITRATE | 2.89 |
| POTASSIUM IODIDE | 0.00009 |
| POTASSIUM CITRATE | 1.5 |
| CORN SYRUP | 7.68 |
| MALTODEXTRIN | 53.6 |
| MAGNESIUM PHOSPHATE DIBASIC | 0.26 |
| CALCIUM PHOSPHATE TRIBASIC | 0.99 |
| MAGNESIUM CHLORIDE | 1.2 |
| SUCROSE | 11.9 |
| FRUCTOOLIGOSACCHARIDE | 5.9 |
| MEDIUM CHAIN TRIGLYCERIDE | 2.6 |
| CANOLA OIL | 1.5 |
| SOY OIL | 0.87 |
| 57% VITAMIN A PALMITATE | 0.007 |
| VITAMIN DEK PREMIX | 0.04 |
| VITAMIN D | 0.0000088 |
| D-ALPHA-TOCOPHEROL ACETATE | 0.036 |
| PHYLLOQUINONE | 0.00006 |
| CARRAGEENAN | 0.03 |
| SOY LECITHIN | 0.6 |
| SODIUM CASEINATE | 15.5 |
| CALCIUM CASEINATE | 4.2 |
| CALCIUM HMB MONOHYDRATE | 2.6 |
| MILK PROTEIN ISOLATE | 14 |
| REFINED DEODORIZED SARDINE OIL | 6.9 |
| ASCORBIC ACID | 0.12 |
| 45% POTASSIUM HYDROXIDE | 0.13 |
| TAURINE | 0.12 |
| WATER SOLUBLE VITAMIN PREMIX | 0.11 |
| NIACINAMIDE | 0.017 |
| CALCIUM PANTOTHENATE | 0.01 |
| THIAMINE CHLORIDE HYDROCHLORIDE | 0.003 |
| PYRIDOXINE HYDROCHLORIDE | 0.003 |
| RIBOFLAVIN | 0.002 |
| FOLIC ACID | 0.0004 |
| BIOTIN | 0.00034 |
| CYANOCOBALAMIN | 0.000038 |
| ASCORBYL PALMITATE | 0.03 |
| CHOLINE CHLORIDE | 0.25 |
| L-CARNITINE | 0.0681 |
| N&A MARSHMALLOW VANILLA | 1.6 |
| N&A DULCE DE LECHE | 0.27 |

The liquid nutritional product of the present invention was manufactured by preparing three slurries which are blended together, combined with refined deodorized sardine oil, heat treated, standardized, packaged and sterilized. The process for manufacturing 454 kg (1,000 pounds) of the liquid nutritional product, using the List of Materials from Table 7, is described in detail below.

A carbohydrate/mineral slurry is prepared by first heating about 62.6 kg of water to a temperature in the range of about 71° C. to 77° C. with agitation. The HMB is added to the water and dissolved by agitating the resultant solution for at least five minutes. The required amount of potassium citrate and ultratrace/trace mineral premix is added to the water and dissolved by agitating the resultant solution for at least 10 minutes. The following minerals are then added, in the order listed, with high agitation: magnesium chloride, potassium chloride, sodium citrate, potassium iodide, magnesium phosphate and tricalcium phosphate. The slurry is allowed to mix under moderate agitation until completely dissolved or dispersed. The corn syrup, sucrose and maltodextrin are then added to the slurry with agitation. Add the required amount of FOS and allow to mix. The completed carbohydrate/mineral slurry is held with high agitation at a temperature in the range of about 60-66° C. for not longer than 8 hours until it is blended with the other slurries.

An oil slurry is prepared by combining and heating the medium chain triglycerides (fractionated coconut oil), canola oil and soy oil to a temperature in the range of about 32-43° C. with agitation. The vitamin DEK premise is added and allowed to mix until completely dispersed. The required amounts of following ingredients are added: sly lecithin, vitamin A, ascorbyl plamitate, and vitamin E. The carrageen is added and allowed to mix until completely dispersed. The completed oil slurry is held under moderate agitation at a temperature in the range of about 32-43° C. for not longer than 8 hours until it is blended with the other slurries.

A protein slurry is prepared by first heating about 196.78 kg of water to a temperature in the range of about 60-63° C. with agitation. The calcium caseinate and sodium caseinate and milk protein isolate are blended into the slurry using a mixing apparatus. The completed protein slurry is held under agitation at a temperature in the range of about 54-60° C. for not longer than 2 hours before being blended with the other slurries.

The oil and the protein slurry are blended together with agitation and the resultant blended slurry is maintained at a temperature in the range of about 54-66° C. After waiting for at least five minutes the carbohydrate/mineral slurry is added to the blended slurry from the preceding step with agitation and the resultant blended slurry is maintained at a temperature in the range of about 54-66° C. The refined deodorized sardine oil is then added to the slurry with agitation. (In a most preferred method of manufacture the sardine oil would be slowly metered into the product as the blend passes through a conduit at a constant rate.) Preferably after at least 5 minutes the pH of the blended slurry is determined. If the pH of the blended slurry is below 6.55, it is adjusted with dilute potassium hydroxide to a pH of 6.5 to 6.8.

After waiting a period of not less than one minute nor greater than two hours the blended slurry is subjected to deaeration, Ultra-High-Temperature (UHT) treatment, and homogenization, as described as follows: use a positive pump for supplying the blended slurry for this procedure; heat the blended slurry to a temperature in the range of about 66-71° C.; deaerate the blended slurry to 25.4-38.1 cm of Hg; emulsify the blended slurry at 61-75 Atmospheres; heat the blended slurry to a temperature in the range of about 120-122° C. by passing it through a plate/coil heat exchanger with a hold time of approximately 10 seconds; UHT heat the blended slurry to a temperature in the range of about 144-147° C. with a hold time of approximately 5 seconds; reduce the temperature of the blended slurry to be in the range of about 120-122° C. by passing it through a flash cooler; reduce the temperature of the blended slurry to be in the range of about 71-82° C. by passing it through a plate/coil heat exchanger; homogenize the blended slurry at about 265 to 266 Atmospheres; pass the blended slurry through a hold tube for at least 16 seconds at a temperature in the range of about 74-85° C.; and cool the blended slurry to a temperature in the range of about 1-70° C. by passing it through a large heat exchanger.

Store the blended slurry at a temperature in the range of about 1-7° C., preferably with agitation.

Preferably at this time appropriate analytical testing for quality control is conducted. Based on the test results an appropriate amount of dilution water (10-38° C.) is added to the blended slurry with agitation.

A vitamin solution and flavor solution are prepared separately and then added to the blended slurry.

The vitamin solution is prepared by heating about 3.94 kg of water to a temperature in the range of about 43-66° C. with agitation, and thereafter adding the following ingredients, in the order listed: Ascorbic Acid, 45% Potassium Hydroxide, Taurine, Water Soluble Vitamin Premix, Choline Chloride, and L-Carnitine. The vitamin solution is then added to the blended slurry with agitation.

The flavor solution is prepared by adding the marshmallow and dulce de leche flavor to about 7.94 kg of water with agitation. A nutritional product according to the present invention has been manufactured using an artificial marshmallow flavor distributed by Firmenich Inc., Princeton, N.J., U.S.A. and a natural & artificial dulce de leche flavor distributed by Firmenich Inc. The flavor solution is then added to the blended slurry with agitation.

If necessary, diluted potassium hydroxide is added to the blended slurry such that the product will have a pH in the range of 6.4 to 7.0 after sterilization. The completed product is then placed in suitable containers and subjected to sterilization. Of course, if desired aseptic processing could be employed.

Example VI

Composition of a Nutritional Product to Control Glycemic Response

Table 2 presents a bill of materials for manufacturing 1,000 kg of a liquid nutritional product, which provides nutrients to a person but limits resulting insulin response. A detailed description of its manufacture follows.

TABLE 2

Bill of Materials for a Liquid Nutritional

| Ingredient | Quantity per 1,000 kg |
| --- | --- |
| Water | QS |
| Maltodextrin | 56 kg |
| Acidc casein | 41.093 kg |
| Fructose | 28 kg |
| High oleic safflower oil | 27.2 kg |
| Maltitol syrup | 16 kg |
| Maltitol | 12.632 kg |
| Fibersol ® 2(E) | 8.421 kg |
| Caseinate | 6.043 kg |
| Fructooligosaccharide | 4.607 kg |
| Soy polysaccharide | 4.3 kg |
| Canola oil | 3.2 kg |
| Tricalcium phosphate | 2.8 kg |
| Magnesium chloride | 2.4 kg |
| Lecithin | 1.6 kg |
| Sodium citrate | 1.18 kg |
| Potassium citrate | 1.146 kg |
| Sodium hydroxide | 1.134 kg |
| Magnesium phosphate | 1.028 kg |
| Calcium HMB monohydrate | 5.7 kg |
| m-inositol | 914.5 gm |
| Vitamin C | 584 gm |
| Potassium chloride | 530 gm |
| Choline chloride | 472.1 gm |
| 45% Potassium hydroxide | 402.5 gm |
| UTM/TM premix | 369.3 gm |
| Potassium phosphate | 333 gm |
| Carnitine | 230.5 gm |
| Gellan gum | 125 gm |
| Ttaurine | 100.1 gm |
| Vitamin E | 99 gm |
| Lutein Esters (5%) | 92 gm |
| WSV premix | 75.4 gm |
| Vitamin DEK premix | 65.34 gm |
| 30% Beta carotene | 8.9 gm |
| Vitamin A | 8.04 gm |

TABLE 2-continued

Bill of Materials for a Liquid Nutritional

| Ingredient | Quantity per 1,000 kg |
|---|---|
| Pyridoxine hydrochloride | 3.7 gm |
| Chromium chloride | 1.22 gm |
| Folic acid | 0.64 gm |
| Potassium iodide | 0.20 gm |
| Cyanocobalamin | 0.013 gm |

WSV premix (per g premix): 375 mg/g niacinamide, 242 mg/g calcium pantothenate, 8.4 gm/g folic acid, 62 mg/g thiamine chloride hydrochloride, 48.4 gm/g riboflavin, 59.6 mg/g pyridoxine hydrochloride, 165 mcg/g cyanocobalamin and 7305 mcg/g biotin
Vitamin DEK premix (per g premix): 8130 IU/g vitamin $D_3$, 838 IU/g vitamin E, 1.42 mg/g vitamin $K_1$
UTM/TM premix (per g premix): 45.6 mg/g zinc, 54 mg/g iron, 15.7 manganese, 6.39 mg/g copper, 222 mcg/g selenium, 301 mcg/g chromium and 480 mcg/g molybdenum The diabetic liquid nutritional products of the present invention are manufactured by preparing four slurries that are blended together, heat treated, standardized, packaged and sterilized.

A carbohydrate/mineral slurry is prepared by first heating about 82 kg of water to a temperature of from about 65° C. to about 71° C. with agitation. With agitation, the required mount of calcium HMB is added and agitated for 5 minutes. The required amount of sodium citrate and gellen gum distributed by the Kelco, Division of Merck and Company Incorporated, San Diego, Calif., U.S.A. is added and agitated for 5 minutes. The required amount of the ultra trace mineral/trace mineral (UTM/TM) premix (distributed by Fortitech, Schnectady, N.Y.) is added. The slurry is greenish yellow in color. Agitation is maintained until the minerals are completely dispersed. With agitation, the required amounts of the following minerals are then added: potassium citrate, potassium chloride, chromium chloride, magnesium chloride and potassium iodide. Next, the first maltodextrin distributed by Grain Processing Corporation, Muscataine, Iowa, U.S.A. and fructose are added to slurry under high agitation, and are allowed to dissolve. With agitation, the required amounts of maltitol powder distributed by Roquette America, Inc., Keokuk, Iowa, maltitol syrup distributed by AlGroup Lonza, Fair Lawn, N.J., fructooligosaccharides distributed by Golden Technologies Company, Golden, Colo., U.S.A. and a second maltodextrin distributed by Matsutani Chemical Industry Co., Hyogo, Japan under the product name Fibersol® 2(E) are added and agitated well until completely dissolved. The required amount of tricalcium phosphate and magnesium phosphate are added to the slurry under agitation. The completed carbohydrate/mineral slurry is held with agitation at a temperature from about 65° C. to about 71° C. for not longer than twelve hours until it is blended with the other slurries.

A fiber in oil slurry is prepared by combining and heating the required amounts of high oleic safflower oil and canola oil to a temperature from about 40.5° C. to about 49° C. with agitation. With agitation, the required amounts of lutein esters from Cognis of LaGrange, Ill. is added. Agitate for a minimum of 15 minutes. With agitation, the required amounts of the following ingredients are added to the heated oil: lecithin (distributed by Central Soya Company, Fort Wayne, Ind.), Vitamin D, E, K premix (distributed by Vitamins Inc., Chicago, Ill.), vitamin A, vitamin E and beta-carotene. The required amounts of soy polysaccharide distributed by Protein Technology International, St. Louis, Mo. is slowly dispersed into the heated oil. The completed oil/fiber slurry is held under moderate agitation at a temperature from about 55° C. to about 65° C. for a period of no longer than twelve hours until it is blended with the other slurries.

A first protein in water slurry is prepared by heating 293 kg of water to 60° C. to 65° C. With agitation, the required amount of 20% potassium citrate solution is added and held for one minute. The required amount of acid casein is added under high agitation followed immediately by the required amount of 20% sodium hydroxide. The agitation is maintained at high until the casein is dissolved. The slurry is held from about 60° C. to 65° C. with moderate agitation.

A second protein in water slurry is prepared by first heating about 77 kg of water to a temperature of about 40° C. with agitation. The caseinate is added and the slurry is agitated well until the caseinate is completely dispersed. With continued agitation, the slurry is slowly warmed to 60° C. to 65° C. The slurry is held for no longer than twelve hours until it is blended with the other slurries.

The batch is assembled by blending 344 kg of protein slurry one with 84 kg of protein slurry two. With agitation, the 37 kg of the oil/fiber slurry is added. After waiting for at least one minute, 216 kg of the carbohydrate/mineral slurry is added to the blended slurry from the preceding step with agitation and the resultant blended slurry is maintained at a temperature from about 55° C. to about 60° C. The pH of the blended batch is adjusted to a pH of 6.45 to 6.75 with 1N potassium hydroxide.

After waiting for a period of not less than one minute nor greater than two hours, the blend slurry is subjected to deaeration, ultra-high-temperature treatment, and homogenization. The blended slurry is heated to a temperature from about 71° C. to about 82° C. and deaerated under vacuum. The heated slurry is then emulsified through a single stage homogenizer at 900 to 1100 psig. After emulsification, the slurry is heated from about 99° C. to about 110° C. and then heated to a temperature of about 146° C. for about 5 seconds. The slurry is passed through a flash cooler to reduce the temperature to from about 99° C. to about 110° C. and then through a plate cooler to reduce the temperature to from about 71° C. to about 76° C. The slurry is then homogenized at 3900 to 4100/400 to 600 psig. The slurry is held at about 74° C. to about 80° C. for 16 seconds and then cooled to 1° C. to about 7° C. At this point, samples are taken for microbiological and analytical testing. The mixture is held under agitation.

A water soluble vitamin (WSV) solution is prepared separately and added to the processed blended slurry.

The vitamin solution is prepared by adding the following ingredients to 9.4 kg of water with agitation: WSV premix (distributed by J.B. Laboratories, Holland, Mich.), vitamin C, choline chloride, L-carnitine, taurine, inositiol, folic acid, pyridoxine hydrochloride and cyanocobalamin. The required amount of 45% potassium hydroxide slurry is added to bring the pH to between 7 and 10.

Based on the analytical results of the quality control tests, an appropriate amount of water is added to the batch with agitation to achieve desired total solids. Additionally, 8.8 kg of vitamin solution is added to the diluted batch under agitation. The product pH may be adjusted to achieve optimal product stability. The completed product is then placed in suitable containers and subjected to terminal sterilization.

Example VII

Composition of a Pediatric Nutritional Product

Table 3 presents a bill of materials for manufacturing 771 kg of a pediatric enteral nutritional of the instant invention. A detailed description of its manufacture follows.

TABLE 3

Bill of materials for vanilla pediatric nutritional

| Ingredient | Quantity per 771 kg |
|---|---|
| Stock PIF Slurry | |
| High oleic safflower oil | 40.7 kg |
| Soy oil | 24.4 kg |
| MCT oil | 16.3 kg |
| Lecithin | 840.2 g |
| Monoglycerides | 840.2 g |
| Carrageenan | 508.9 g |
| Caseinate | 32.8 kg |
| Stock OSV blend | |
| DEK premix | 83.3 g |
| Vitamin A | 7.1 g |
| Lutein esters (5%) | 92 g |
| Stock PIW slurry | |
| Water | 530 kg |
| Caseinate | 11.3 kg |
| Whey protein | 11.9 kg |
| Stock MIN slurry | |
| Water | 18 kg |
| Cellulose gum | 1696 g |
| Calcium HMB monohydrate | 4.4 kg |
| Magnesium chloride | 2.7 kg |
| Potassium chloride | 1.0 kg |
| Potassium citrate | 2.7 kg |
| Potassium iodide | 0.25 g |
| Dipotassium phosphate | 1.45 kg |
| Final blend | |
| PIW slurry | 251 kg |
| PIF slurry | 53 kg |
| MIN slurry | 12.6 kg |
| Sodium chloride | 127.4 g |
| Sucrose | 77.6 kg |
| Tricalcium phosphate | 2.5 kg |
| Water | 167 kg |
| Stock WSV solution | |
| Water | 31.7 kg |
| Potassium citrate | 3.74 g |
| UTM/TM premix | 172.2 g |
| WSV premix | 134.1 g |
| m-inositol | 176.7 g |
| Ttaurine | 145.5 g |
| L-carnitine | 34.92 g |
| Choline chloride | 638.7 g |
| Stock ascorbic acid solution | |
| Water | 18.6 kg |
| Ascorbic acid | 550.0 g |
| 45% KOH | 341 g |
| Stock vanilla solution | |
| Water | 38.5 kg |
| Vanilla flavor | 4.3 kg |

DEK premix: (per gm premix) 12,100 IU vitamin $D_3$, 523 IU vitamin E, 0.962 mg vitamin $K_1$
UTM/TM premix: (per gm premix) 132 mg zinc, 147 mg iron, 10.8 mg manganese, 12.5 mg copper, 0.328 mg selenium, 0.284 mg molybdenum
WSV premix: (per gm premix) 375 mg niacinamide, 242 mg d-calcium pantothenate, 8.4 mg folic acid, 62 mg thiamine chloride hydrochloride, 48.4 mg riboflavin, 59.6 mg pyridoxine hydrochloride, 165.5 mcg cyanocobalamin, 7305 mcg biotin The stock oil soluble vitamin blend (OSV blend) is prepared by weighing out the specified amount of DEK premix into a screw cap, light protected container large enough to hold 54 g of oil soluble vitamins. Using a plastic pipette, the required amount of vitamin A is added to the DEK aliquot. The container is flushed with nitrogen prior to applying the lid.

The stock protein in fat slurry (PIF) was prepared by adding the required amounts of high oleic safflower oil, soy oil and MCT oil to the blend tank. The mixture is heated to 40.5° C. to 49° C. with agitation. With agitation, the required amounts of lutein esters from American River Nutrition of Hadley, Mass. is added. Agitate for a minimum of 15 minutes. The emulsifiers, lecithin (distributed by Central Soya of Decatur, Ind.) and monoglycerides (distributed by Quest of Owings Mills, Md.), are added and mixed well to dissolve. All of the OSV blend is then added. The containers are rinsed out 4 to 5 times with the oil blend to assure complete transfer of the vitamins. The carrageenan (distributed by FMC of Rockland, Me.) and the caseinate are added. The slurry is mixed well to disperse the protein. The PIF slurry is held up to six hours at 60-65° C. under moderate agitation until used.

The stock protein in water slurry (PIW) is prepared by adding the required amount of water to a blend tank. The water is held under moderate agitation and brought up to 76-82° C. The required amount of caseinate is added to the water under high agitation and mixed on high until the protein is fully dispersed. The protein slurry is allowed to cool to 54-60° C. before proceeding. Once cooled the required amount of whey protein is added and mixed well until fully dispersed/dissolved. The PIW slurry is held up to two hours at 54-60° C. until used.

The stock mineral solution (MIN) is prepared by adding the required amount of water to a blend tank and heated to 60-68° C. The cellulose gum blend (distributed by FMC of Newark, Del.) is added to the water and held under moderate agitation for a minimum of five minutes before proceeding. The calcium HMB is added and agitated for a minimum of five minutes before proceeding. The mineral salts magnesium chloride, potassium chloride, potassium citrate, potassium iodide and dipotassium phosphate are added one at a time with mixing between each addition to ensure the minerals dissolved. The completed MIN solution is held at 54-65° C. under low to moderate agitation until used.

The final blend is prepared by adding the specified amount of PIW slurry to a blend tank and heated under agitation to 54-60° C. The specified amount of PIF slurry is added to the tank and mixed well. The specified amount of MIN solution is added to the blend and mixed well. The specified amount of sodium chloride is added to the blend and mixed well. The specified amount of sucrose is added to the blend and mixed well to dissolve. The tricalcium phosphate is added to the blend and mixed well to disperse. The specified amount of additional water is added to the blend and mixed well. The completed final blend is held under continuous agitation at 54-60° C. If necessary, the pH is adjusted to 6.45-6.8 with 1N KOH.

After waiting for a period of not less than one minute nor greater than two hours, the blend slurry is subjected to deaeration, ultra-high-temperature treatment, and homogenization. The blended slurry is heated to a temperature from about 68° C. to about 74° C. and deaerated under vacuum. The heated slurry is then emulsified at 900 to 1100 psig. After emulsification, the slurry is heated from about 120° C. to about 122° C. and then heated to a temperature of about 149° C. to about 150° C. The slurry is passed through a flash cooler to reduce the temperature to from about 120° C. to about 122° C. and then through a plate cooler to reduce the temperature to from about 74° C. to about 79° C. The slurry is then homogenized at 3900 to 4100/400 to 600 psig. The slurry is held at about 74° C. to about 85° C. for 16 seconds and then cooled to 1° C. to about 6° C. At this point, samples are taken for microbiological and analytical testing. The mixture is held under agitation.

Standardization proceeds as follows. The stock vitamin solution (WSV) is prepared by heating the specified amount of water to 48-60° C. in a blend tank. Potassium citrate, UTM/TM premix (distributed by Fortitech of Schenectady, N.Y.), WSV premix, m-inositol, taurine, L-carnitine and choline chloride are each added to the solution in the order listed and allowed to mix well to dissolve or disperse each ingredient. 14.2 kg of the vitamin solution is added to the processed mix tank.

The stock vanilla solution is prepared by adding the specified amount of water to a blend tank. The specified amount of vanilla (distributed by Givaudan Roure of Cincinnati, Ohio) is added to the water and mixed well. 18.5 kg of vanilla solution is added to the processed mix tank and mixed well.

The stock ascorbic acid solution is prepared by adding the required amount of water to a blend tank. The specified amount of ascorbic acid is added and mixed well to dissolve. The specified amount of 45% KOH is added and mixed well. 8.4 kg of ascorbic acid solution is added to the mix tank and mixed well.

The final mix is diluted to the final total solids by adding 92.5 kg of water and mixed well. Product is filed into suitable containers prior to terminal (retort) sterilization.

Example VIII

Composition of a Complete Nutritional Supplement

Table 4 presents a bill of materials for manufacturing 1,000 kg of a typical vanilla flavored meal replacement liquid. A detailed description of its manufacture follows.

TABLE 4

Bill of Materials for *Vanilla* Liquid Nutritional

| Ingredient | Quantity per 1,000 kg |
|---|---|
| Water | QS |
| Corn Syrup | 33 kg |
| Maltodextrin | 28 kg |
| Sucrose | 19.4 kg |
| Caseinate | 8.7 kg |
| Calcium HMB monohydrate | 5.7 kg |
| High Oleic Safflower Oil | 4.1 kg |
| Canola Oil | 4.1 kg |
| Soy Protein | 3.7 kg |
| Whey Protein | 3.2 kg |
| Caseinate | 2.9 kg |
| Corn Oil | 2.0 kg |
| Tricalcium Phosphate | 1.4 kg |
| Potassium Citrate | 1.3 kg |
| Magnesium Phosphate | 952 gm |
| Lecithin | 658 gm |
| Magnesium chloride | 558 gm |
| Vanilla Flavor | 544 gm |
| Sodium Chloride | 272 gm |
| Carrageenan | 227 gm |
| Choline chloride | 218 gm |
| UTM/TM Premix | 165 gm |
| Potassium Chloride | 146 gm |
| Ascorbic Acid | 145 gm |
| Sodium Citrate | 119 gm |
| Potassium Hydroxide | 104 gm |
| Lutein (5%) | 46 gm |
| WSV Premix | 33 gm |
| Vit DEK Premix | 29 gm |
| Vitamin A | 3.7 gm |
| Potassium Iodide | 86 mcg |

WSV premix (per g premix): 375 mg/g niacinamide, 242 mg/g calcium pantothenate, 8.4 gm/g folic acid, 62 mg/g thiamine chloride hydrochloride, 48.4 gm/g riboflavin, 59.6 mg/g pyridoxine hydrochloride, 165 mcg/g cyanocobalamin and 7305 mcg/g biotin
Vitamin DEK premix (per g premix): 8130 IU/g vitamin $D_3$, 838 IU/g vitamin E, 1.42 mg/g vitamin $K_1$
UTM/TM premix (per g premix): 45.6 mg/g zinc, 54 mg/g iron, 15.7 manganese, 6.39 mg/g copper, 222 mcg/g selenium, 301 mcg/g chromium and 480 mcg/g molybdenium The liquid meal replacement products of the present invention are manufactured by preparing three slurries that are blended together, heat treated, standardized, packaged and sterilized.

A carbohydrate/mineral slurry is prepared by first heating the required amount of water to a temperature of from about 65° C. to about 71° C. with agitation. The required amount of calcium HMB is added and agitated for a minimum of 5 minutes. With agitation, the required amount of potassium citrate and ultra trace mineral/trace mineral (UTM/TM) premix (distributed by Fortitech, Schnectady, N.Y.) is added. The slurry is greenish yellow in color. Agitation is maintained until the minerals are completely dispersed. With agitation, the required amounts of the following minerals are then added: magnesium chloride, potassium chloride, sodium chloride, sodium citrate, potassium iodide, magnesium phosphate and tricalcium phosphate. Next, the maltodextrin distributed by Grain Processing Corporation, Muscataine, Iowa, U.S.A., sucrose and corn syrup are added to slurry under high agitation, and are allowed to dissolve. The completed carbohydrate/mineral slurry is held with agitation at a temperature from about 65° C. to about 71° C. for not longer than eight hours until it is blended with the other slurries.

A protein in fat slurry (PIF) is prepared by combining and heating the required amounts of high oleic safflower oil and canola oil to a temperature from about 40.5° C. to about 49° C. with agitation. With agitation, the required amounts of free lutein from Kemin Foods of Des Moines, Iowa is added. Agitate for a minimum of 15 minutes. Add the following ingredients are added to the heated oil: lecithin (distributed by Central Soya Company, Fort Wayne, Ind.), vitamin A, and Vitamin D, E, K premix (distributed by Vitamins Inc., Chicago, Ill.). The required amount of carrageenan is dry blended with the required amount of whey protein and add to the agitating lipid mixture and allowed to agitate for a minimum of 10 minutes. The required amount of soy protein is added to the blend slowly to assure proper mixing. The completed oil/protein slurry is held under moderate agitation at a temperature from about 40° C. to about 43° C. for a period of no longer than two hours until it is blended with the other slurries.

A protein in water slurry is prepared by first heating about required amount of water to a temperature of about 40° C. with agitation. The caseinate is added and the slurry is agitated well until the caseinate is completely dispersed. With continued agitation, the slurry is slowly warmed to 60° C. to 65° C. The slurry is held for no longer than twelve hours until it is blended with the other slurries.

The batch is assembled by blending required amount of protein slurry with required amount of the carbohydrate/mineral slurry and allowed to agitate for 10 minutes. With agitation, the required amount of the oil/protein slurry is added and agitate for at least 10 minutes. The pH of the blended batch is adjusted to a pH of 6.66 to 6.75 with 1N potassium hydroxide.

After waiting for a period of not less than one minute nor greater than two hours, the blend slurry is subjected to deaeration, ultra-high-temperature treatment, and homogenization. The blended slurry is heated to a temperature from about 71° C. to about 82° C. and deaerated under vacuum. The heated slurry is then emulsified through a single stage homogenizer at 900 to 1100 psig. After emulsification, the slurry is heated from about 99° C. to about 110° C. and then heated to a temperature of about 146° C. for about 5 seconds. The slurry is passed through a flash cooler to reduce the temperature to from about 99° C. to about 110° C. and then through a plate cooler to reduce the temperature to from about 71° C. to about 76° C. The slurry is then homogenized at 3900 to 4100/400 to 600 psig. The slurry is held at about 74° C. to about 80° C. for 16 seconds and then cooled to 1° C. to about 7° C. At this point, samples are taken for microbiological and analytical testing. The mixture is held under agitation.

A water soluble vitamin (WSV) solution is prepared separately and added to the processed blended slurry.

The vitamin solution is prepared by adding the following ingredients to 9.4 kg of water with agitation: WSV premix (distributed by J.B. Laboratories, Holland, Mich.), vitamin C, choline chloride, L-carnitine, taurine, inositiol, folic acid, pyridoxine hydrochloride and cyanocobalamin. The required amount of 45% potassium hydroxide slurry is added to bring the pH to between 7 and 10.

Based on the analytical results of the quality control tests, an appropriate amount of water is added to the batch with agitation to achieve the desired total solids. Additionally, 8.8 kg of vitamin solution is added to the diluted batch under agitation.

The product pH may be adjusted to achieve optimal product stability. The completed product is then placed in suitable containers and subjected to terminal sterilization.

Example IX

Composition of a Beverage

To produce a 1000 kg batch of ready-to-drink beverage, 987.31 kg of water is placed in a vessel fitted with an agitator. At ambient temperature, the required amount of potassium benzoate is added and allowed to completely dissolve. The required amount of calcium HMB is added and allowed to completely dissolve. The following ingredients are then added in the order listed. Each ingredient is completely dissolved before the next ingredient is added.

TABLE 5

Ready-to-drink beverage

| Ingredient | Quantity |
|---|---|
| Potassium benzoate | 0.30 kg |
| Calcium HMB monohydrate | 5.7 kg |
| Potassium Citrate | 0.15 kg |
| Citric Acid | 2.89 kg |
| Lactic Acid | 1.41 kg |
| Aspartame | 0.55 kg |
| Calcium Glycerophosphate | 6.06 kg |
| Coloring Agents | 0.0019 kg |
| Natural and artificial flavors | 1.00 kg |
| Ascorbic acid | 0.33 kg |

The ascorbic acid was added just before filling into 12-oz. aluminum cans. The beverages may be carbonated prior to filling into aluminum cans. The solution is deaerated and then transferred to a "carbo-cooler" where it is cooled and carbonated to approximately 2.5 volumes of carbon dioxide.

Example X

Composition of an Electrolyte Replacement Product

The following example explains how to manufacture a ready-to-drink rehydration solution. The ORS had the composition outlined in Table 6.

TABLE 6

Ready-to-drink Rehydration Solution

| Ingredient | Quantity per 454 kg |
|---|---|
| Water | 437 kg |
| Dextrose, Monohydrate | 10 kg |
| Fructose | 2.4 kg |
| Citric Acid | 1.2 kg |

TABLE 6-continued

Ready-to-drink Rehydration Solution

| Ingredient | Quantity per 454 kg |
|---|---|
| Sodium Chloride | 0.937 kg |
| Potassium Citrate | 1 kg |
| Sodium Citrate | 492.0 g |
| Calcium HMB monohydrate | 5.7 kg |
| Fruit Flavor | 226.8 g |
| Zinc Gluconate | 80.62 g |
| Sucralose | 179.2 g |
| Acesulfame Potassium | 38.1 g |
| Yellow #6 | 7.2 g |

Weigh out the required amount of filtered water and add to blend tank. Heat the water to 43-54° C., with moderate agitation. While maintaining moderate agitation, the calcium HMB is added and allowed to mix for a minimum of 5 minutes. With continued moderate agitation add the required amount of dextrose. Agitate until dissolved. Add the required amount of fructose. Agitate until dissolved. Add the required amount of the following ingredients, in the order listed, to the dextrose/fructose blend and agitate until dissolved: zinc gluconate, sodium citrate, sodium chloride, potassium citrate, and citric acid. Add the required amount of sucralose (distributed by McNeil Specialty Products Company of New Brunswick, N.J.) and acesulfame potassium (distributed as Sunsett® by Hoechst Food Ingredients of Somerset, N.J.) and agitate until dissolved. Add the yellow #6 and the fruit punch flavor to the batch until dissolved. Cool the blend to 1.1-7.2° C. and hold with low agitation. Fill the required number of one liter plastic bottles, apply the foil heat seal to the bottle opening, and retort to food grade sterility standards.

Alternatively, the cooled blend is encapsulated within a sealable freezable packaging material and sealed such as by heat sealing. A single dose of rehydration solution is packaged in a hermetically sealed freezable pouch. Various types of packaging materials which can be used to practice the invention, such as that used in traditional freezer pops, would be readily apparent to the skilled artisan. The wrapping material is preferably a type which will allow markings, such as product identification, ingredients, etc., to be placed on the exterior surface thereof. The rehydration formulation is shipped and stored, preferably in multiple units thereof, in this condition. It is contemplated that multiple units or freezer pops will be packaged together for purposes of commercialization.

Prior to administration, a package of liquid rehydration solution is frozen. Following freezing, the package is opened and the contents thereof eaten. Since the frozen rehydration formulation will normally be administered at ambient temperatures, the amount of rehydration liquid contained in each package is preferably an amount which can be consumed in its entirely while still in the frozen state. Preferably 20-35 ounces, more preferably 2.0 to 2.5 ounces per package. In a particularly preferred embodiment, 2.1 ounces of sterile rehydration solution is encapsulated within an rectangular, e.g., 1".times.8," freezable wrapper material. Clear plastic wrapper material is preferred.

Example XI

Effect of HMB on Protein Synthesis (vs. Degradation) in Skeletal Muscle

Materials.

Materials and animals were obtained as per Example 1.

Methodologies.

Protein synthesis was measured by the incorporation of L-[4-3H]phenylalanine during a 2-hour period in which isolated gastrocnemius muscles were incubated at 37° C. in RPMI 1640 without phenol red and saturated with O2/CO2 (19:1). After incubation muscles were rinsed in nonradioactive medium, blotted dry, and homogenized in 4 mL 2% perchloric acid. The rate of protein synthesis was calculated by dividing the protein-bound radioactivity by the acid-soluble (unbound) material.

For protein degradation assays animals from the same group as used to measure protein synthesis were given i.p. 0.4 mmol/L L-[4-3H]phenylalanine in PBS (100 µl) 24 hours prior to the assay. Isolated gastrocnemius muscles were extensively washed with PBS and RPMI 1640 before measuring the release of radioactivity into RPMI 1640 over a 2-hour period. The protein-bound activity was determined by homogenizing the muscles in 2% perchloric acid and determining the non-acid-soluble radioactivity (radioactivity in the precipitate). The rate of protein degradation was calculated by dividing the amount of [$^3$H]phenylalanine radioactivity released into the incubation medium during the 2-hour incubation period by the specific activity of protein-bound [$^3$H] phenylalanine.

Western Blot analysis and statistical treatments were as described in Example 1.

Results.

Figure 4B:
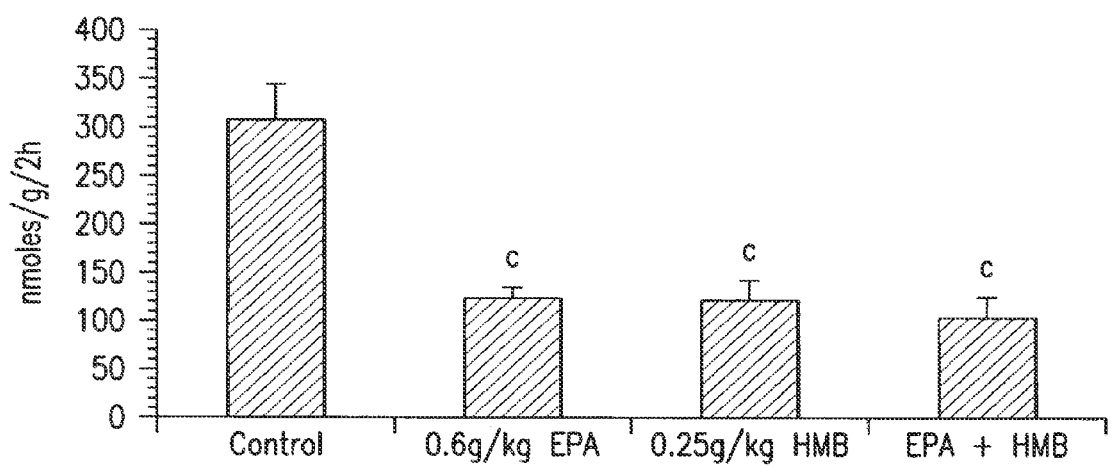

The protein degradation in these muscles was measured by tyrosine released per gram of muscle over 2 hours, taking into consideration the variation in muscle sizes (FIG. 4B). At the doses chosen HMB was as effective as EPA and there did not seem to be a synergistic effect of the combination, however, the combination of HMB with EPA may permit lower doses of each ingredient without loss of efficacy. Body composition analysis (Table 1) indicated that HMB caused a significant increase in the nonfat carcass mass without an effect on adipose tissue.

TABLE 1

Body composition analysis of mice bearing the MAC16 tumor treated with HMB for 5 days

| HMB (g/kg) | Water (%) | Fat (%) | Nonfat (%) |
|---|---|---|---|
| 0 | 70.8 ± 2.7 | 3.8 ± 1.3 | 25.4 ± 1.9 |
| 0.125 | 65.5 ± 0.9 | 3.3 ± 1.6 | 31.2 ± 1.5* |
| 0.25 | 66.5 ± 2.2 | 4.4 ± 1.3 | 29.2 ± 1.9* |
| 0.5 | 67.2 ± 2.3 | 3.8 ± 1.2 | 29.0 ± 1.4* |

*P < 0.01 from control group receiving 0 g/kg HMB.

Figure 14A:
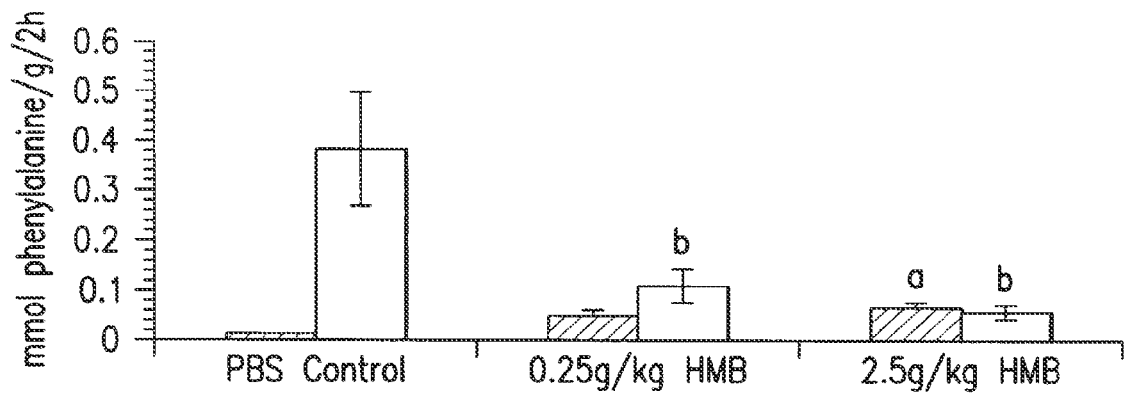
FIG. 14 presents the effects of HMB on protein synthesis (stimulated) and degradation (inhibited) in the gastrocnemius muscles of MAC16 tumor-bearing animals. Panel 14 A shows the effect of daily p.o. administration of 0.25 g/kg and 2.5 g/kg HMB on the rate of protein synthesis (dark-shaded columns) and degradation (unshaded columns), expressed as millimoles of phenylalanine incorporated or released per gram of muscle per 2 hours. Treatment was terminated after 3 days. Columns, mean (n=6); bars, SE. Differences from PBS control: a, $P<0.05$; b, $P<0.001$. Panel 14 B shows the ratio of the rate of protein synthesis to the rate of protein degradation in gastrocnemius muscles of mice treated in A.
Figure 14B:
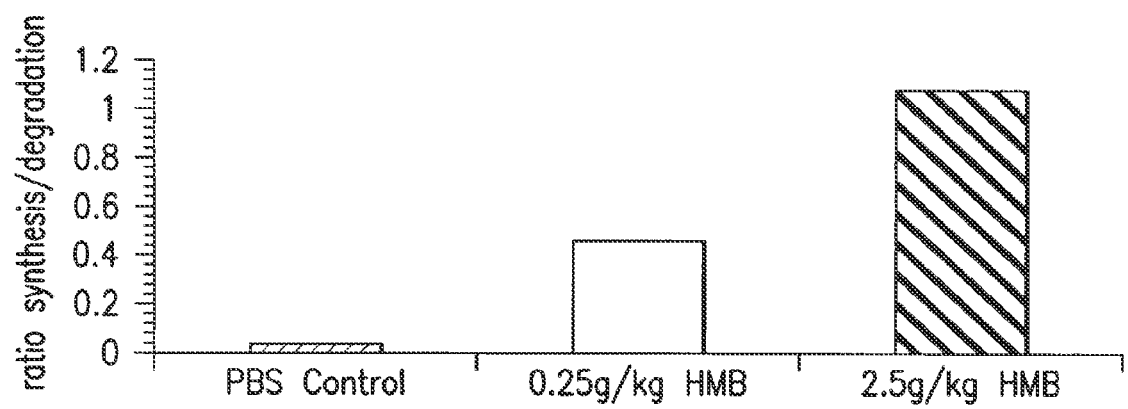

EPA has been shown to attenuate the increase in protein degradation in skeletal muscle of mice bearing the MAC16 tumor but has no effect on the depression of protein synthesis (Beck, et al. Cancer Res. 1991; 284:206-10). In contrast, HMB, when evaluated at two dose levels (0.25 and 2.5 g/kg) in the present experiment not only attenuated protein degradation but also significantly increased protein synthesis in gastrocnemius muscle of mice bearing the MAC16 tumor when compared with control animals receiving PBS. This is shown in FIG. 14A, where synthesis (dark-shaded columns) increases compared to control and degradation (unshaded columns) decreases compared to control. This opposite effect resulted in an increase in the ratio of protein synthesis to protein degradation in muscle (FIG. 14B) by 14-fold with HMB at 0.25 g/kg and by 32-fold at 2.5 g/kg.

Lean muscle status is always a dynamic system of synthesis and degradation. This study shows that HMB can affect both processes favorably in wasting patients to increase overall lean mass. HMB is capable not only of attenuating protein degradation in skeletal muscle, but also stimulates protein synthesis resulting in an increase in the nonfat carcass mass. This is particularly important in wasting disease states like cachexia and AIDS that manifest themselves as loss of lean muscle loss.

We claim:

1. A method of treating disease-associated wasting of a patient comprising administering to the patient a composition comprising:
    a. beta-hydroxy-beta-methylbutyrate, its salts, metabolites or derivatives thereof;
    b. carnitine; and
    c. an amino nitrogen source enriched with large neutral amino acids;
    wherein the composition is substantially lacking in free amino acids; and
    wherein the disease-associated wasting is associated with a disease selected from the group consisting of cachexia, cancer, age-associated wasting, wasting associated with long-term hospital stay, HIV/AIDS, arthritis, trauma, liver disease, Crohn's disease, inflammatory bowel diseases, renal insufficiency, and chronic obstructive pulmonary disease.

2. The method according to claim 1, wherein the beta-hydroxy-beta-methylbutyrate is selected from the group consisting of sodium beta-hydroxy-beta-methylbutyrate, potassium beta-hydroxy-beta-methylbutyrate, magnesium beta-hydroxy-beta-methylbutyrate, chromium beta-hydroxy-beta-methylbutyrate, calcium beta-hydroxy-beta-methylbutyrate, alkali metal beta-hydroxy-beta-methylbutyrate, alkaline earth metal beta-hydroxy-beta-methylbutyrate and beta-hydroxy-beta-methylbutyrate lactone.

3. The method according to claim 2, wherein the beta-hydroxy-beta-methylbutyrate is calcium beta-hydroxy-beta-methylbutyrate.

4. The method according to claim 1, wherein the composition comprises at least 2 grams beta-hydroxy-beta-methylbutyrate in a daily serving.

5. The method according to claim 1, wherein the composition further comprises omega-3 fatty acids.

6. The method according to claim 5, wherein the omega-3 fatty acids are selected from the group consisting of alpha-linolenic acid, stearidonic acid, eicosapentaenoic acid, docosapentaenoic acid and docosahexaenoic acid.

7. The method according to claim 6, wherein the omega-3 fatty acids are eicosapentaenoic acid.

8. The method according to claim 7, wherein the composition comprises at least 0.5 grams eicosapentaenoic acid in a daily serving.

9. The method according to claim 8, wherein the composition comprises at least 1.0 grams eicosapentaenoic acid in a daily serving.

10. The method according to claim 1, wherein the large neutral amino acids comprise at least 10% of the amino nitrogen source.

11. The method according to claim 1, wherein the free amino acids comprise less than 0.4 grams per serving of the composition.

12. The method according to claim 1, wherein the composition comprises less than 2 grams of carnitine in a daily serving.

13. The method according to claim 1, wherein the composition further comprises an indigestible oligosaccharide.

14. The method according to claim 13, wherein the indigestible oligosaccharide is fructooligosaccharide.

15. The method according to claim 14, wherein the composition comprises at least 1 gram of fructooligosaccharide in a daily serving.

16. The method according to claim 15, wherein the composition comprises from about 2 grams to about 4 grams of fructooligosaccharide in a daily serving.

17. The method according to claim 1, wherein the composition further comprises a nutrient selected from the group consisting of vitamins, minerals, and trace minerals.

18. The method according to claim 1, wherein the composition further comprises at least one antioxidant selected from the group consisting of beta-carotene, vitamin E, vitamin C, and selenium.

19. The method according to claim 1, wherein the composition is administered to a human.

20. The method according to claim 1, wherein the composition is selected from the group consisting of a dietary supplement, meal replacement, nutritional bar, chew or bite and beverage.

* * * * *